(12) United States Patent
Aldaz et al.

(10) Patent No.: US 10,774,156 B2
(45) Date of Patent: Sep. 15, 2020

(54) IGG BISPECIFIC ANTIBODIES AND PROCESSES FOR PREPARATION

(71) Applicants: Eli Lilly and Company, Indianapolis, IN (US); The University of North Carolina at Chapel Hill, Chapel Hill, NC (US)

(72) Inventors: Hector Aldaz, San Marcos, CA (US); Shane Krummen Atwell, Carlsbad, CA (US); Stephen John Demarest, San Diego, CA (US); Karen Jean Froning, San Diego, CA (US); Brian Arthur Kuhlman, Chapel Hill, NC (US); Andrew Philip Leaver-Fay, Carrboro, NC (US)

(73) Assignees: Eli Lilly and Company, Indianapolis, IN (US); The University of North Carolina at Chapel Hill, Chapel Hill, NC (US)

( * ) Notice: Subject to any disclaimer, the term of this patent is extended or adjusted under 35 U.S.C. 154(b) by 71 days.

(21) Appl. No.: 15/545,047

(22) PCT Filed: Jan. 21, 2016

(86) PCT No.: PCT/US2016/014313
§ 371 (c)(1),
(2) Date: Jul. 20, 2017

(87) PCT Pub. No.: WO2016/118742
PCT Pub. Date: Jul. 28, 2016

(65) Prior Publication Data
US 2018/0009908 A1   Jan. 11, 2018

Related U.S. Application Data

(60) Provisional application No. 62/106,494, filed on Jan. 22, 2015.

(51) Int. Cl.
| | | |
|---|---|---|
| *C07K 16/40* | (2006.01) | |
| *C07K 16/00* | (2006.01) | |
| *C07K 16/30* | (2006.01) | |
| *C07K 16/46* | (2006.01) | |
| C07K 16/32 | (2006.01) | |
| C07K 16/28 | (2006.01) | |

(52) U.S. Cl.
CPC ......... *C07K 16/468* (2013.01); *C07K 16/00* (2013.01); *C07K 16/2863* (2013.01); *C07K 16/2878* (2013.01); *C07K 16/32* (2013.01); *C07K 2317/31* (2013.01); *C07K 2317/52* (2013.01); *C07K 2317/522* (2013.01); *C07K 2317/526* (2013.01); *C07K 2317/56* (2013.01); *C07K 2317/94* (2013.01)

(58) Field of Classification Search
CPC .............. C07K 16/468; C07K 16/2863; C07K 16/2878

USPC ..................... 530/387.3; 424/133.1
See application file for complete search history.

(56) References Cited

U.S. PATENT DOCUMENTS

| | | | |
|---|---|---|---|
| 573,168 A | 3/1998 | Carter et al. | |
| 2007/0237779 A1 | 10/2007 | Ledbetter et al. | |
| 2009/0182127 A1 | 7/2009 | Kjaergaard et al. | |
| 2010/0015133 A1 | 1/2010 | Igawa et al. | |
| 2010/0105874 A1 | 4/2010 | Schuurman et al. | |
| 2011/0038869 A1* | 2/2011 | Van Den Brink ... | C07K 16/283 424/135.1 |
| 2013/0209355 A1* | 8/2013 | De Weers .......... | C07K 16/2896 424/1.49 |
| 2014/0010809 A1 | 1/2014 | Ledbetter et al. | |
| 2014/0154254 A1 | 6/2014 | Kannan et al. | |
| 2014/0200331 A1 | 7/2014 | Corper et al. | |
| 2017/0129962 A1* | 5/2017 | Regula ............ | C07K 16/22 |
| 2017/0349669 A1* | 12/2017 | Imhof-Jung ........ | C07K 16/00 |
| 2019/0040156 A1* | 2/2019 | Demarest .......... | A61P 37/06 |
| 2019/0382475 A1* | 12/2019 | Cebe ............... | C07K 16/28 |

FOREIGN PATENT DOCUMENTS

| | | |
|---|---|---|
| WO | 2007109254 A2 | 9/2007 |
| WO | 2009089004 A1 | 7/2009 |
| WO | 2011028952 A1 | 3/2011 |
| WO | 2012058768 A1 | 5/2012 |
| WO | 2012131555 A2 | 10/2012 |
| WO | 2013063702 A2 | 5/2013 |
| WO | 2013033008 A2 | 7/2013 |
| WO | 2014150973 A1 | 9/2014 |

OTHER PUBLICATIONS

Choi et al. (Mol Cancer Ther; 12(12): 2748-2759 (Dec. 2013)).*
Elliott et al. (J. Mol. Biol. 426: 1947-1957 (2014)).*
Choi et al. (Molec. Immunol. 65(2): 377-383 (Jun. 2015)).*
Choi et al. (PLoS One. Dec. 16, 2015;10(12):e0145349. doi: 10.1371/journal.pone.0145349. eCollection 2015).*
Ha et al. (Front Immunol. Oct. 6, 2016;7:394. eCollection 2016).*
Skegro et al. ( J Biol Chem. Jun. 9, 2017;292(23):9745-9759; Epub Apr. 27, 2017).*
Yu et al. ( J Biol Chem. Oct. 27, 2017;292(43):17885-17896. doi: 10.1074/jbc.M116.771188. Epub Sep. 6, 2017).*
Wei et al. (Oncotarget, 2017, vol. 8, (No. 31), pp: 51037-51049).*
Jordan, J., et al., "Structural understanding of stabilization patterns in engineered bispecific Ig-like antibody molecules", Proteins: Structure, Function, and Bioinformatic, vol. 77, No. 4, Dec. 1, 2009, pp. 832-841, XP055002049, ISSN: 0887-3585, DOI: 10,1002/PROT. 22502.

(Continued)

*Primary Examiner* — Lynn A Bristol
(74) *Attorney, Agent, or Firm* — Robert L Sharp

(57) ABSTRACT

The present invention provides fully IgG bi-specific antibodies comprising designed residues in the interface of the heavy chain-heavy chain ($C_H3/C_H3$) domains, processes for preparing said fully IgG bi-specific antibodies, and nucleic acids, vectors and host cells encoding the same.

10 Claims, 1 Drawing Sheet
Specification includes a Sequence Listing.

(56) References Cited

OTHER PUBLICATIONS

Schaefer, W., et al., "Immunoglobulin domain crossover as a generic approach for the production of bispecific IgG antibodies", Proceedings of the National Academy of Sciences, vol. 108, No. 27. Jul. 5, 2011, pp. 11187-11192, X9055003817, ISSN: 0027-8424, DOI: 10.1073/pnas. 1019002108.

Gunasekaran, K et al., "Enchancing Antibody Fc Heterodimer Formation through Electrostatic Steering Effects: Applications to Bispecific Molecules and Monovalent IgG", Journal of Biological Chemistry, vol. 285, No. 25, Jun. 18, 2010, pp. 19637-19646, XP055001947, ISSN: 0021-9258, DOI: 10.1074/ ibc.M110.117382.

Spasevska, I., "An outlook on bispecific antibodies: Methods of production and therapeutic benefits", Bio Sciences Master Reviews, Jan. 21, 2013, Xp055122817, Retrieved from the internet: URL:http://biologie.ens-Iyon.fr/biologie/ressources/bibliographoes/pdf/m1-12-13-biosci-reviews-spasevska-i-2c-m.pdf?lang=en [retrieved on Jun. 11, 2014].

Lewis, S., et al., "Generation of bispecific IgG antibodies by structure-based design of an orthogonal Fab interface", Nature Biotechnology, vol. 32, No. 2, Feb. 1, 2014, pp. 191-198, XP055122831, ISSN: 1087-0156, DOI 10.1038/nbt.2797PLOS ONE, vol. 6, No. 6, Jun. 17, 2011, p. e20872, XP055122659. ISSN: 1932-6203, DOI: 10.1371/ journal.pone. 0020872.

Labrijn, A.F., et al., "Efficient generation of stable bispecific IgG1 by controlled Fab-arm exchange-Supporting Information", Proceedings of the National Academy of Sciences, vol. 110, No. 13, Mar. 11, 2013 (Mar. 11, 2013), XP055201661, ISSN: 0027-8484, DOI: 10.1073/pnas.1220145110 abstract.

Carter, Paul E et al., "Bispecific human IgG by design", Journal of Immunological Methods, Elsevier Science Publishers B.V., Amsterdam, NL, vol. 248, No. 1-2, Jan. 1, 2001 (Jan. 1, 2001), pp. 7-15, XP002974199, ISSN: 0022-1759, DOI: 10.1016/S0022-1759(00)00339-2 abstract.

Leaver-Fay A., et al., "Computationally Designed Bispecific Antibodies using Negative State Repertoires", Structure, vol. 24, No. 4, Apr. 1, 2016 (Apr. 1, 2016), pp. 641-651, XP055263232, US ISSN: 0969-2126, DOI: 10.1016/j.str.2016.02.013 the whole document.

Rudikoff, S., et al., "Single Amino Acid Substitution Altering Antigen-Binding Specificity", Proceedings of the National Academy of Sciences, National Academy of Sciences, US, vol. 79, Mar. 1982 (Mar. 1, 1982), pp. 1979-1983, XP007901436, ISSN: 0027-8424, DOI: 10.1073/PNAS.79.6.1979.

Zhenping Zhu, et al., "Remodeling Domain Interfaces to Enhance Heterodimer Formation", Protein Science (1997), vol. 6, No. 4, Apr. 1, 1997 (Apr. 1, 1997), pp. 781-788, XP055345091, US, ISSN: 0961-8368, DOI: 10.1002/pro.5560060404.

Salfeld, Jochen G., "Isotype Selection in Antibody Engineering", Nature Biotechnology, Nature Publishing Group, United States, vol. 25, No. 12, Dec. 1, 2007 (Dec. 1, 2007), pp. 1369-1372, XP002668461, ISSN: 1546-1696, DOI: 10.1038/NBT1207-1369.

Klein, C., et al., "Progress in overcoming the chain association issue in bispecific heterodimeric IgG antibodies", Landes Bioscience, vol. 4, Aug. 27, 2012, pp. 653-663, ISSN: 1942-0862.

Igawa, "VH/VL interface engineering to promote selective expression and inhibit conformational isomerization of thrombopoietin receptor agonist single-chain diabody", Protein Engineering, Design & Selection, vol. 23 No. 8 pp. 667-677, 2010, Jun. 24, 2010 doi:10.1093/protein/gzq034.

Davis, J.H., et al., "SEEDbodies: fusion proteins based on strand-exchange engineered domain (SEED) CH3 heterodimers in an Fc analogue platform for asymmetric binders or immunofusions and bispecific antibodies", Protein Engineering, Design & Selection vol. 23 No. 4 pp. 195-202, 2010, Feb. 4, 2010 doi:10.1093/protein/gzp094.

\* cited by examiner

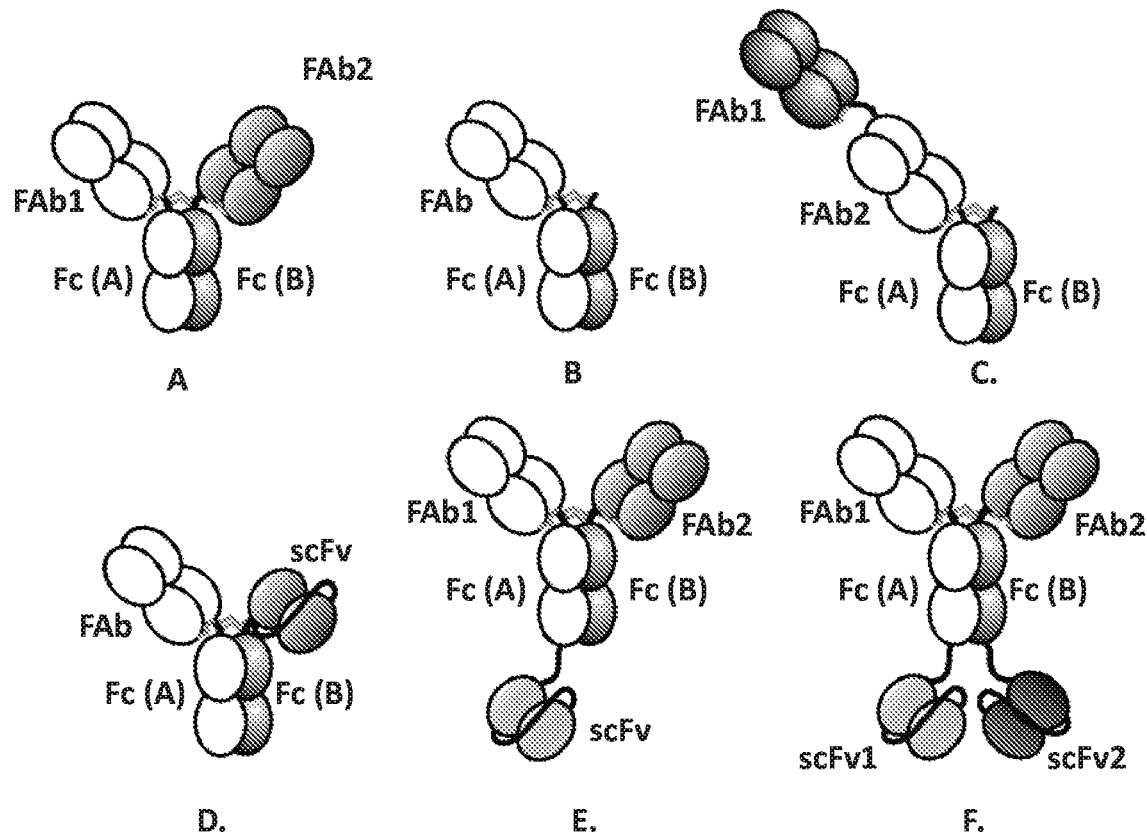

Legend:

A. Fully IgG BsAb comprising two Fabs (1 and 2) to separate targets and an Fc.
B. One-arm antibody comprising one Fab and one Fc.
C. Tandem Fab-Fc comprising two Fabs (1 and 2) to separate targets linked head-to-tail, and one Fc.
D. IgG-scFv-Fc comprising one Fab (to a first target) and an scFv (to a second target) and one Fc.
E. IgG-scFv comprising two Fabs (1 and 2) to separate targets, a scFv to a third target, and an Fc.
F. IgG-scFv comprising two Fabs (1 and 2) to separate targets, two scFvs (1 and 2) to separate targets, and an Fc.

"Fc(A)" and "Fc(B)" represent distinct CH2-CH3 segments containing CH3 designs and which form the Fc heterodimer

SEQUENCE LISTING

<160> NUMBER OF SEQ ID NOS: 69

<210> SEQ ID NO 1
<211> LENGTH: 449
<212> TYPE: PRT
<213> ORGANISM: Artificial Sequence
<220> FEATURE:

-continued

<223> OTHER INFORMATION: Synthetic Construct

<400> SEQUENCE: 1

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Gln Ala Pro Gly Lys Gly Leu Glu Trp Val
        35                  40                  45

Gly Met Ile Asp Pro Ser Asn Ser Asp Thr Arg Phe Asn Pro Asn Phe
50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400
```

```
Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
        435                 440                 445

Lys

<210> SEQ ID NO 2
<211> LENGTH: 241
<212> TYPE: PRT
<213> ORGANISM: Artificial Sequence
<220> FEATURE:
<223> OTHER INFORMATION: Synthetic Construct

<400> SEQUENCE: 2

Tyr Pro Tyr Asp Val Pro Asp Tyr Ala Ser Gly Ser Gly Ser Asp Lys
1               5                   10                  15

Thr His Thr Cys Pro Pro Cys Pro Ala Pro Glu Leu Leu Gly Gly Pro
            20                  25                  30

Ser Val Phe Leu Phe Pro Pro Lys Pro Lys Asp Thr Leu Met Ile Ser
        35                  40                  45

Arg Thr Pro Glu Val Thr Cys Val Val Val Asp Val Ser His Glu Asp
50                  55                  60

Pro Glu Val Lys Phe Asn Trp Tyr Val Asp Gly Val Glu Val His Asn
65                  70                  75                  80

Ala Lys Thr Lys Pro Arg Glu Glu Gln Tyr Asn Ser Thr Tyr Arg Val
                85                  90                  95

Val Ser Val Leu Thr Val Leu His Gln Asp Trp Leu Asn Gly Lys Glu
            100                 105                 110

Tyr Lys Cys Lys Val Ser Asn Lys Ala Leu Pro Ala Pro Ile Glu Lys
        115                 120                 125

Thr Ile Ser Lys Ala Lys Gly Gln Pro Arg Glu Pro Gln Val Tyr Thr
    130                 135                 140

Leu Pro Pro Ser Arg Glu Glu Met Thr Lys Asn Gln Val Ser Leu Thr
145                 150                 155                 160

Cys Leu Val Lys Gly Phe Tyr Pro Ser Asp Ile Ala Val Glu Trp Glu
                165                 170                 175

Ser Asn Gly Gln Pro Glu Asn Asn Tyr Lys Thr Thr Pro Pro Val Leu
            180                 185                 190

Asp Ser Asp Gly Ser Phe Phe Leu Tyr Ser Lys Leu Thr Val Asp Lys
        195                 200                 205

Ser Arg Trp Gln Gln Gly Asn Val Phe Ser Cys Ser Val Met His Glu
    210                 215                 220

Ala Leu His Asn His Tyr Thr Gln Lys Ser Leu Ser Leu Ser Pro Gly
225                 230                 235                 240

Lys

<210> SEQ ID NO 3
<211> LENGTH: 220
<212> TYPE: PRT
<213> ORGANISM: Artificial Sequence
<220> FEATURE:
<223> OTHER INFORMATION: Synthetic Construct

<400> SEQUENCE: 3

Asp Ile Gln Met Thr Gln Ser Pro Ser Ser Leu Ser Ala Ser Val Gly
```

```
            1               5                  10                 15
Asp Arg Val Thr Ile Thr Cys Lys Ser Ser Gln Ser Leu Leu Tyr Thr
                20                  25                  30
Ser Ser Gln Lys Asn Tyr Leu Ala Trp Tyr Gln Gln Lys Pro Gly Lys
                35                  40                  45
Ala Pro Lys Leu Leu Ile Tyr Trp Ala Ser Thr Arg Glu Ser Gly Val
                50                  55                  60
Pro Ser Arg Phe Ser Gly Ser Gly Ser Gly Thr Asp Phe Thr Leu Thr
65                  70                  75                  80
Ile Ser Ser Leu Gln Pro Glu Asp Phe Ala Thr Tyr Tyr Cys Gln Gln
                85                  90                  95
Tyr Tyr Ala Tyr Pro Trp Thr Phe Gly Gln Gly Thr Lys Val Glu Ile
                100                 105                 110
Lys Arg Thr Val Ala Ala Pro Ser Val Phe Ile Phe Pro Pro Ser Asp
                115                 120                 125
Glu Gln Leu Lys Ser Gly Thr Ala Ser Val Val Cys Leu Leu Asn Asn
                130                 135                 140
Phe Tyr Pro Arg Glu Ala Lys Val Gln Trp Lys Val Asp Asn Ala Leu
145                 150                 155                 160
Gln Ser Gly Asn Ser Gln Glu Ser Val Thr Glu Gln Asp Ser Lys Asp
                165                 170                 175
Ser Thr Tyr Ser Leu Ser Ser Thr Leu Thr Leu Ser Lys Ala Asp Tyr
                180                 185                 190
Glu Lys His Lys Val Tyr Ala Cys Glu Val Thr His Gln Gly Leu Ser
                195                 200                 205
Ser Pro Val Thr Lys Ser Phe Asn Arg Gly Glu Cys
                210                 215                 220

<210> SEQ ID NO 4
<211> LENGTH: 449
<212> TYPE: PRT
<213> ORGANISM: Artificial Sequence
<220> FEATURE:
<223> OTHER INFORMATION: Synthetic Construct

<400> SEQUENCE: 4

Glu Gln Lys Leu Ile Ser Glu Glu Asp Leu Ser Gly Ser Glu Glu Arg
1               5                   10                  15
Lys Val Cys Asn Gly Ile Gly Ile Gly Glu Phe Lys Asp Ser Leu Ser
                20                  25                  30
Ile Asn Ala Thr Asn Ile Lys His Phe Lys Asn Cys Thr Ser Ile Ser
                35                  40                  45
Gly Asp Leu His Ile Leu Pro Val Ala Phe Arg Gly Asp Ser Phe Thr
                50                  55                  60
His Thr Pro Pro Leu Asp Pro Gln Glu Leu Asp Ile Leu Lys Thr Val
65                  70                  75                  80
Lys Glu Ile Thr Gly Phe Leu Leu Ile Gln Ala Trp Pro Glu Asn Arg
                85                  90                  95
Thr Asp Leu His Ala Phe Glu Asn Leu Glu Ile Ile Arg Gly Arg Thr
                100                 105                 110
Lys Gln His Gly Gln Phe Ser Leu Ala Val Val Ser Leu Asn Ile Thr
                115                 120                 125
Ser Leu Gly Leu Arg Ser Leu Lys Glu Ile Ser Asp Gly Asp Val Ile
                130                 135                 140
Ile Ser Gly Asn Lys Asn Leu Cys Tyr Ala Asn Thr Ile Asn Trp Lys
```

```
            145                 150                 155                 160
Lys Leu Phe Gly Thr Ser Gly Gln Lys Thr Lys Ile Ile Ser Asn Arg
                165                 170                 175

Gly Glu Asn Ser Cys Lys Ala Thr Gly Gln Val Cys His Ala Leu Cys
                180                 185                 190

Ser Pro Glu Gly Cys Trp Gly Pro Glu Pro Arg Asp Cys Val Ser Cys
                195                 200                 205

Arg Asn Val Ser Arg Gly Arg Glu Cys Val Asp Lys Gly Ser Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 5
<211> LENGTH: 345
<212> TYPE: PRT
<213> ORGANISM: Artificial Sequence
<220> FEATURE:
<223> OTHER INFORMATION: Synthetic Construct

<400> SEQUENCE: 5

Glu Gln Lys Leu Ile Ser Glu Glu Asp Leu Ser Gly Ser Gln Thr Asn
1               5                   10                  15

Thr Ile Leu Asp Val Gln Ile Arg Pro Pro Ser Pro Val Arg Leu Leu
                20                  25                  30

His Gly Gln Thr Leu Val Leu Asn Cys Thr Ala Thr Thr Glu Leu Asn
            35                  40                  45

Thr Arg Val Gln Met Ser Trp Asn Tyr Pro Gly Lys Ala Thr Lys Arg
        50                  55                  60
```

```
Ala Ser Ile Arg Gln Arg Ile Asp Arg Ser His Ser His Asn Asn Val
 65                  70                  75                  80

Phe His Ser Val Leu Lys Ile Asn Asn Val Glu Ser Arg Asp Lys Gly
                 85                  90                  95

Leu Tyr Thr Cys Arg Val Lys Ser Gly Ser Ser Phe Gln Ser Phe Asn
            100                 105                 110

Thr Ser Val His Gly Ser Asp Lys Thr His Thr Cys Pro Pro Cys Pro
        115                 120                 125

Ala Pro Glu Leu Leu Gly Gly Pro Ser Val Phe Leu Phe Pro Pro Lys
130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Gln Tyr Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Glu Glu Met
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
        275                 280                 285

Tyr Lys Thr Thr Pro Pro Val Leu Asp Ser Asp Gly Ser Phe Phe Leu
290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
            340                 345

<210> SEQ ID NO 6
<211> LENGTH: 227
<212> TYPE: PRT
<213> ORGANISM: Artificial Sequence
<220> FEATURE:
<223> OTHER INFORMATION: Synthetic Construct

<400> SEQUENCE: 6

Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
                 20                  25                  30

Ile Ser Arg Thr Pro Glu Val Thr Cys Val Val Val Asp Val Ser His
             35                  40                  45

Glu Asp Pro Glu Val Lys Phe Asn Trp Tyr Val Asp Gly Val Glu Val
         50                  55                  60

His Asn Ala Lys Thr Lys Pro Arg Glu Glu Gln Tyr Asn Ser Thr Tyr
 65                  70                  75                  80
```

-continued

```
Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 7
<211> LENGTH: 217
<212> TYPE: PRT
<213> ORGANISM: Artificial Sequence
<220> FEATURE:
<223> OTHER INFORMATION: Synthetic Construct

<400> SEQUENCE: 7

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Ala Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205
```

```
Lys Ser Leu Ser Leu Ser Pro Gly Lys
    210                 215

<210> SEQ ID NO 8
<211> LENGTH: 217
<212> TYPE: PRT
<213> ORGANISM: Artificial Sequence
<220> FEATURE:
<223> OTHER INFORMATION: Synthetic Construct

<400> SEQUENCE: 8

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Met Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Val Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 9
<211> LENGTH: 449
<212> TYPE: PRT
<213> ORGANISM: Artificial Sequence
<220> FEATURE:
<223> OTHER INFORMATION: Synthetic Construct

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Lys Ala Pro Gly Lys Gly Leu Glu Trp Val
        35                  40                  45

Ala Asp Val Asn Pro Asn Ser Gly Gly Ser Ile Tyr Asn Gln Glu Phe
    50                  55                  60

Lys Gly Arg Phe Thr Leu Ser Val Asp Arg Ser Lys Asn Thr Leu Tyr
```

```
            65                  70                  75                  80
Leu Gln Met Asn Ser Leu Arg Ala Glu Asp Thr Ala Val Tyr Tyr Cys
                    85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 10
<211> LENGTH: 449
<212> TYPE: PRT
<213> ORGANISM: Artificial Sequence
<220> FEATURE:
```

<223> OTHER INFORMATION: Synthetic Construct

<400> SEQUENCE: 10

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
             20                  25                  30

Thr Met Asp Trp Val Arg Lys Ala Pro Gly Lys Gly Leu Glu Trp Val
         35                  40                  45

Ala Asp Val Asn Pro Asn Ser Gly Gly Ser Ile Tyr Asn Gln Glu Phe
     50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
             100                 105                 110

Thr Leu Val Thr Val Ser Ser Ala Ser Thr Lys Gly Pro Ser Val Phe
         115                 120                 125

Pro Leu Ala Pro Ser Ser Lys Ser Thr Ser Gly Gly Thr Ala Ala Leu
     130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val Ala Thr Gly Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

-continued

```
Met Ser Asp Gly Ser Phe Phe Leu Ala Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 11
<211> LENGTH: 449
<212> TYPE: PRT
<213> ORGANISM: Artificial Sequence
<220> FEATURE:
<223> OTHER INFORMATION: Synthetic Construct

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Lys Ala Pro Gly Lys Gly Leu Glu Trp Val
        35                  40                  45

Ala Asp Val Asn Pro Asn Ser Gly Gly Ser Ile Tyr Asn Gln Glu Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```
(Note: "His Thr Phe" above — re-check)

```
Asn Ser Gly Ala Leu Thr Ser Gly Val Ala Thr Gly Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
    290                 295                 300

Val Ser Val Leu Thr Val Leu His Gln Asp Trp Leu Asn Gly Lys Glu
```

```
                305                 310                 315                 320
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Asp Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Met Ser Asp Gly Ser Phe Phe Leu Ala Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 12
<211> LENGTH: 449
<212> TYPE: PRT
<213> ORGANISM: Artificial Sequence
<220> FEATURE:
<223> OTHER INFORMATION: Synthetic Construct

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
                20                  25                  30

Thr Met Asp Trp Val Arg Lys Ala Pro Gly Lys Gly Leu Glu Trp Val
            35                  40                  45

Ala Asp Val Asn Pro Asn Ser Gly Gly Ser Ile Tyr Asn Gln Glu Phe
        50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val Ala Thr Gly Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220
```

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Gln Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Ser Thr
            340                 345                 350

Leu Pro Pro Ser Arg Glu Glu Met Thr Lys Asn Gln Val Ser Leu Val
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Val Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 13
<211> LENGTH: 449
<212> TYPE: PRT
<213> ORGANISM: Artificial Sequence
<220> FEATURE:
<223> OTHER INFORMATION: Synthetic Construct

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Lys Ala Pro Gly Lys Gly Leu Glu Trp Val
        35                  40                  45

Ala Asp Val Asn Pro Asn Ser Gly Gly Ser Ile Tyr Asn Gln Glu Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125
```

```
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val Ala Thr Gly Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Ser Thr
            340                 345                 350

Leu Pro Pro Ser Arg Glu Glu Met Thr Lys Asn Gln Val Ser Leu Met
        355                 360                 365

Cys Leu Val Tyr Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Val Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 14
<211> LENGTH: 212
<212> TYPE: PRT
<213> ORGANISM: Artificial Sequence
<220> FEATURE:
<223> OTHER INFORMATION: Synthetic Construct

<400> SEQUENCE: 14

Arg Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Asp Lys Pro Gly Lys Ala Pro Lys Leu Leu Ile
```

```
                35                  40                  45
Tyr Ser Ala Ser Tyr Arg Tyr Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ile Tyr Pro Tyr
                 85                  90                  95

Thr Phe Gly Gln Gly Thr Lys Val Glu Ile Lys Gly Gln Pro Lys Ala
                100                 105                 110

Ala Pro Ser Val Thr Leu Phe Pro Pro Ser Ser Glu Glu Leu Gln Ala
            115                 120                 125

Asn Lys Ala Thr Leu Val Cys Tyr Ile Ser Asp Phe Tyr Pro Gly Ala
130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Trp
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys
        210

<210> SEQ ID NO 15
<211> LENGTH: 449
<212> TYPE: PRT
<213> ORGANISM: Artificial Sequence
<220> FEATURE:
<223> OTHER INFORMATION: Synthetic Construct

<400> SEQUENCE: 15

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Thr Phe Thr Ser Tyr
             20                  25                  30

Trp Leu His Trp Val Arg Lys Ala Pro Gly Lys Gly Leu Glu Trp Val
         35                  40                  45

Gly Met Ile Asp Pro Ser Asn Ser Asp Thr Arg Phe Asn Pro Glu Phe
 50                  55                  60

Lys Asp Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Thr Tyr Arg Ser Tyr Val Thr Pro Leu Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val Ala Thr Gly Pro Ala Val Leu
                165                 170                 175

Gln Ser Ser Gly Leu Tyr Ser Leu Ser Ser Val Val Thr Val Pro Ser
```

```
                180                 185                 190
Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Gln Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys
```

<210> SEQ ID NO 16
<211> LENGTH: 449
<212> TYPE: PRT
<213> ORGANISM: Artificial Sequence
<220> FEATURE:
<223> OTHER INFORMATION: Synthetic Construct

<400> SEQUENCE: 16

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Lys Ala Pro Gly Lys Gly Leu Glu Trp Val
            35                  40                  45

Gly Met Ile Asp Pro Ser Asn Ser Asp Thr Arg Phe Asn Pro Glu Phe
        50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95
```

Ala Thr Tyr Arg Ser Tyr Val Thr Pro Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Val
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Val Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 17
<211> LENGTH: 449
<212> TYPE: PRT
<213> ORGANISM: Artificial Sequence
<220> FEATURE:
<223> OTHER INFORMATION: Synthetic Construct

<400> SEQUENCE: 17

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Lys Ala Pro Gly Lys Gly Leu Glu Trp Val
            35                  40                  45

Gly Met Ile Asp Pro Ser Asn Ser Asp Thr Arg Phe Asn Pro Glu Phe
50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Thr Tyr Arg Ser Tyr Val Thr Pro Leu Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Gln Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Arg Pro Arg Val Tyr Thr
            340                 345                 350

Leu Pro Pro Ser Arg Glu Glu Met Thr Lys Asn Gln Val Ser Leu Val
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Val Leu Thr Val Asp Lys
            405                 410                 415

Ser Arg Trp Gln Gln Gly Asn Val Phe Ser Cys Ser Val Met His Glu
```

```
                     420                 425                 430
Ala Leu His Asn His Tyr Thr Gln Lys Ser Leu Ser Leu Ser Pro Gly
            435                 440                 445
Lys

<210> SEQ ID NO 18
<211> LENGTH: 449
<212> TYPE: PRT
<213> ORGANISM: Artificial Sequence
<220> FEATURE:
<223> OTHER INFORMATION: Synthetic Construct

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Lys Ala Pro Gly Lys Gly Leu Glu Trp Val
        35                  40                  45

Gly Met Ile Asp Pro Ser Asn Ser Asp Thr Arg Phe Asn Pro Glu Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val Ala Thr Gly Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335
```

```
Thr Ile Ser Lys Ala Lys Gly Gln Pro Arg Glu Pro Gln Val Ser Thr
            340                 345                 350

Leu Pro Pro Ser Arg Glu Glu Met Thr Lys Asn Gln Val Ser Leu Val
            355                 360                 365

Cys Leu Val Tyr Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Val Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 19
<211> LENGTH: 449
<212> TYPE: PRT
<213> ORGANISM: Artificial Sequence
<220> FEATURE:
<223> OTHER INFORMATION: Synthetic Construct

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Lys Ala Pro Gly Lys Gly Leu Glu Trp Val
        35                  40                  45

Gly Met Ile Asp Pro Ser Asn Ser Asp Thr Arg Phe Asn Pro Glu Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val Ala Thr Gly Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240
```

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Ser Thr
            340                 345                 350

Leu Pro Pro Ser Arg Glu Glu Met Thr Lys Asn Gln Val Ser Leu Met
        355                 360                 365

Cys Leu Val Tyr Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Val Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 20
<211> LENGTH: 218
<212> TYPE: PRT
<213> ORGANISM: Artificial Sequence
<220> FEATURE:
<223> OTHER INFORMATION: Synthetic Construct

<400> SEQUENCE: 20

Arg Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Thr
                20                  25                  30

Ser Ser Gln Lys Asn Tyr Leu Ala Trp Tyr Gln Asp Lys Pro Gly Lys
            35                  40                  45

Ala Pro Lys Leu Leu Ile Tyr Trp Ala Ser Thr Arg Glu Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys Gly Gln Pro Lys Ala Ala Pro Ser Val Thr Leu Phe Pro Pro Ser
        115                 120                 125

Ser Glu Glu Leu Gln Ala Asn Lys Ala Thr Leu Val Cys Tyr Ile Ser
    130                 135                 140

Asp Phe Tyr Pro Gly Ala Val Thr Val Ala Trp Lys Ala Asp Ser Ser

```
145                 150                 155                 160
Pro Val Lys Ala Gly Val Glu Thr Thr Thr Pro Ser Lys Gln Ser Asn
                165                 170                 175
Asn Lys Tyr Ala Ala Trp Ser Tyr Leu Ser Leu Thr Pro Glu Gln Trp
                180                 185                 190
Lys Ser His Arg Ser Tyr Ser Cys Gln Val Thr His Glu Gly Ser Thr
                195                 200                 205
Val Glu Lys Thr Val Ala Pro Thr Glu Cys
                210                 215

<210> SEQ ID NO 21
<211> LENGTH: 446
<212> TYPE: PRT
<213> ORGANISM: Artificial Sequence
<220> FEATURE:
<223> OTHER INFORMATION: Synthetic Construct

<400> SEQUENCE: 21

Gln Val Gln Leu Val Gln Ser Gly Ala Glu Val Lys Lys Pro Gly Ser
1               5                   10                  15
Ser Val Lys Val Ser Cys Lys Ala Ser Gly Tyr Thr Phe Thr Thr Tyr
                20                  25                  30
Tyr Leu His Trp Val Arg Tyr Ala Pro Gly Gln Gly Leu Glu Trp Met
            35                  40                  45
Gly Trp Ile Tyr Pro Gly Asn Val His Ala Gln Tyr Asn Glu Lys Phe
        50                  55                  60
Lys Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Trp Glu Gly Phe Pro Tyr Trp Gly Arg Gly Thr Thr Val
                100                 105                 110
Thr Val Ser Ser Ala Ser Thr Lys Gly Pro Ser Val Phe Pro Leu Ala
            115                 120                 125
Pro Cys Ser Lys Ser Thr Ser Gly Gly Thr Ala Ala Leu Gly Cys Leu
        130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
                180                 185                 190
Gly Thr Gln Thr Tyr Ile Cys Asn Val Asn His Lys Pro Ser Asn Thr
            195                 200                 205
Lys Val Asp Lys Lys Val Glu Pro Asp Ser Gly Asp Lys Thr His Thr
        210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
                260                 265                 270
Lys Phe Asn Trp Tyr Val Asp Gly Val Glu Val His Asn Ala Lys Thr
            275                 280                 285
Lys Pro Arg Glu Glu Gln Tyr Asn Ser Thr Tyr Arg Val Val Ser Val
```

```
                    290                 295                 300
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 22
<211> LENGTH: 446
<212> TYPE: PRT
<213> ORGANISM: Artificial Sequence
<220> FEATURE:
<223> OTHER INFORMATION: Synthetic Construct

<400> SEQUENCE: 22

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
                20                  25                  30

Tyr Leu His Trp Val Arg Tyr Ala Pro Gly Gln Gly Leu Glu Trp Met
                35                  40                  45

Gly Trp Ile Tyr Pro Gly Asn Val His Ala Gln Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Glu Gly Phe Pro Tyr Trp Gly Arg Gly Thr Thr Val
                100                 105                 110

Thr Val Ser Ser Ala Ser Thr Lys Gly Pro Ser Val Phe Pro Leu Ala
                115                 120                 125

Pro Cys Ser Lys Ser Thr Ser Gly Gly Thr Ala Ala Leu Gly Cys Leu
                130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Asp Ser Gly Asp Lys Thr His Thr
```

```
            210                 215                 220
Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Val Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Val Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 23
<211> LENGTH: 446
<212> TYPE: PRT
<213> ORGANISM: Artificial Sequence
<220> FEATURE:
<223> OTHER INFORMATION: Synthetic Construct

<400> SEQUENCE: 23

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Tyr Leu His Trp Val Arg Tyr Ala Pro Gly Gln Gly Leu Glu Trp Met
            35                  40                  45

Gly Trp Ile Tyr Pro Gly Asn Val His Ala Gln Tyr Asn Glu Lys Phe
50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Ser Trp Glu Gly Phe Pro Tyr Trp Gly Arg Gly Thr Thr Val
            100                 105                 110

Thr Val Ser Ser Ala Ser Thr Lys Gly Pro Ser Val Phe Pro Leu Ala
            115                 120                 125

Pro Cys Ser Lys Ser Thr Ser Gly Gly Thr Ala Ala Leu Gly Cys Leu
```

```
            130                 135                 140
Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Asp Ser Gly Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Arg Pro Arg Val Tyr Thr Leu Pro Pro
                340                 345                 350

Ser Arg Glu Glu Met Thr Lys Asn Gln Val Ser Leu Val Cys Leu Val
                355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Val Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 24
<211> LENGTH: 446
<212> TYPE: PRT
<213> ORGANISM: Artificial Sequence
<220> FEATURE:
<223> OTHER INFORMATION: Synthetic Construct

<400> SEQUENCE: 24

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
                20                  25                  30

Tyr Leu His Trp Val Arg Tyr Ala Pro Gly Gln Gly Leu Glu Trp Met
                35                  40                  45

Gly Trp Ile Tyr Pro Gly Asn Val His Ala Gln Tyr Asn Glu Lys Phe
```

```
            50                  55                  60
Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Trp Glu Gly Phe Pro Tyr Trp Gly Arg Gly Thr Thr Val
                100                 105                 110

Thr Val Ser Ser Ala Ser Thr Lys Gly Pro Ser Val Phe Pro Leu Ala
                115                 120                 125

Pro Cys Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Lys Val Glu Pro Asp Ser Gly Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Asp Met Thr Lys Asn Gln Val Gln Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Ala Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 25
<211> LENGTH: 446
<212> TYPE: PRT
<213> ORGANISM: Artificial Sequence
```

<220> FEATURE:
<223> OTHER INFORMATION: Synthetic Construct

<400> SEQUENCE: 25

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Tyr Leu His Trp Val Arg Tyr Ala Pro Gly Gln Gly Leu Glu Trp Met
        35                  40                  45

Gly Trp Ile Tyr Pro Gly Asn Val His Ala Gln Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Glu Gly Phe Pro Tyr Trp Gly Arg Gly Thr Thr Val
            100                 105                 110

Thr Val Ser Ser Ala Ser Thr Lys Gly Pro Ser Val Phe Pro Leu Ala
        115                 120                 125

Pro Cys Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Asp Ser Gly Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Gly Asp Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400
```

```
Gly Ser Phe Phe Leu Ala Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 26
<211> LENGTH: 446
<212> TYPE: PRT
<213> ORGANISM: Artificial Sequence
<220> FEATURE:
<223> OTHER INFORMATION: Synthetic Construct

<400> SEQUENCE: 26

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Tyr Leu His Trp Val Arg Tyr Ala Pro Gly Gln Gly Leu Glu Trp Met
        35                  40                  45

Gly Trp Ile Tyr Pro Gly Asn Val His Ala Gln Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Glu Gly Phe Pro Tyr Trp Gly Arg Gly Thr Thr Val
            100                 105                 110

Thr Val Ser Ser Ala Ser Thr Lys Gly Pro Ser Val Phe Pro Leu Ala
        115                 120                 125

Pro Cys Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Asp Ser Gly Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320
```

```
Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Glu Asp Met Thr Lys Asn Gln Val Arg Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Ala Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 27
<211> LENGTH: 214
<212> TYPE: PRT
<213> ORGANISM: Artificial Sequence
<220> FEATURE:
<223> OTHER INFORMATION: Synthetic Construct

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Ile Asn
            20                  25                  30

Val Ala Trp Tyr Gln Arg Lys Pro Gly Asp Ala Pro Lys Ser Leu Ile
            35                  40                  45

Ser Ser Ala Ser Tyr Arg Tyr Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Asp Thr Tyr Pro Phe
            85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Lys Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 28
```

```
<211> LENGTH: 451
<212> TYPE: PRT
<213> ORGANISM: Artificial Sequence
<220> FEATURE:
<223> OTHER INFORMATION: Synthetic Construct

<400> SEQUENCE: 28
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Tyr Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Cys Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Asp Ser Gly
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

```
Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 29
<211> LENGTH: 451
<212> TYPE: PRT
<213> ORGANISM: Artificial Sequence
<220> FEATURE:
<223> OTHER INFORMATION: Synthetic Construct

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Tyr Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Cys Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Asp Ser Gly
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285
```

```
His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Met Ser Asp Gly Ser Phe Phe Leu Ala Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 30
<211> LENGTH: 451
<212> TYPE: PRT
<213> ORGANISM: Artificial Sequence
<220> FEATURE:
<223> OTHER INFORMATION: Synthetic Construct

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
                20                  25                  30

Trp Met His Trp Val Arg Tyr Ala Pro Gly Gln Gly Leu Glu Trp Ile
            35                  40                  45

Gly Glu Phe Asn Pro Ser Asn Gly Arg Thr Asn Tyr Asn Glu Lys Phe
        50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Cys Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Asp Ser Gly
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Glu Glu Met Thr Lys Asn Gln Val Ser
    355                 360                 365

Leu Val Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Val Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly Lys
    450

<210> SEQ ID NO 31
<211> LENGTH: 451
<212> TYPE: PRT
<213> ORGANISM: Artificial Sequence
<220> FEATURE:
<223> OTHER INFORMATION: Synthetic Construct

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Tyr Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
            85                  90                  95
```

```
Ala Ser Arg Asp Tyr Asp Tyr Asp Gly Arg Tyr Phe Asp Tyr Trp Gly
            100                 105                 110
Arg Gly Thr Leu Val Thr Val Ser Ala Ser Thr Lys Gly Pro Ser
        115                 120                 125
Val Phe Pro Leu Ala Pro Cys Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Val Glu Pro Asp Ser Gly
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Asp Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Met Ser Asp Gly Ser Phe Phe Leu Ala Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 32
<211> LENGTH: 451
<212> TYPE: PRT
<213> ORGANISM: Artificial Sequence
<220> FEATURE:
<223> OTHER INFORMATION: Synthetic Construct

<400> SEQUENCE: 32
```

```
Gln Val Gln Leu Val Gln Ser Gly Ala Glu Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Tyr Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
            85                  90                  95

Ala Ser Arg Asp Tyr Asp Tyr Asp Gly Arg Tyr Phe Asp Tyr Trp Gly
        100                 105                 110

Arg Gly Thr Leu Val Thr Val Ser Ser Ala Ser Thr Lys Gly Pro Ser
        115                 120                 125

Val Phe Pro Leu Ala Pro Cys Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Asp Ser Gly
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Arg Val
        340                 345                 350

Tyr Thr Leu Pro Pro Ser Arg Glu Glu Met Thr Lys Asn Gln Val Ser
        355                 360                 365

Leu Val Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Val Leu Thr Val
            405                 410                 415
```

```
Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 33
<211> LENGTH: 451
<212> TYPE: PRT
<213> ORGANISM: Artificial Sequence
<220> FEATURE:
<223> OTHER INFORMATION: Synthetic Construct

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Tyr Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Cys Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Asp Ser Gly
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320
```

```
Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Asp Met Thr Lys Asn Gln Val Gln
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Ala Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 34
<211> LENGTH: 451
<212> TYPE: PRT
<213> ORGANISM: Artificial Sequence
<220> FEATURE:
<223> OTHER INFORMATION: Synthetic Construct

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Tyr Ala Pro Gly Gln Gly Leu Glu Trp Ile
            35                  40                  45

Gly Glu Phe Asn Pro Ser Asn Gly Arg Thr Asn Tyr Asn Glu Lys Phe
    50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
                100                 105                 110

Arg Gly Thr Leu Val Thr Val Ser Ala Ser Thr Lys Gly Pro Ser
            115                 120                 125

Val Phe Pro Leu Ala Pro Cys Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Asp Ser Gly
    210                 215                 220
```

```
Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Gly Asp Met Thr Lys Asn Gln Val Gln
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Ala Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 35
<211> LENGTH: 451
<212> TYPE: PRT
<213> ORGANISM: Artificial Sequence
<220> FEATURE:
<223> OTHER INFORMATION: Synthetic Construct

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Tyr Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Arg Gly Thr Leu Val Thr Val Ser Ser Ala Ser Thr Lys Gly Pro Ser
        115                 120                 125
```

Val Phe Pro Leu Ala Pro Cys Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Asp Ser Gly
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Asp Met Thr Lys Asn Gln Val Arg
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Ala Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 36
<211> LENGTH: 213
<212> TYPE: PRT
<213> ORGANISM: Artificial Sequence
<220> FEATURE:
<223> OTHER INFORMATION: Synthetic Construct

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Thr Tyr Met
            20                  25                  30

Tyr Trp Tyr Gln Arg Lys Pro Gly Asp Ala Pro Lys Leu Leu Ile Tyr
            35                  40                  45

Asp Thr Ser Asn Leu Ala Ser Gly Val Pro Ser Arg Phe Ser Gly Ser
 50                  55                  60

Gly Ser Gly Thr Asp Tyr Thr Phe Thr Ile Ser Ser Leu Gln Pro Glu
 65                  70                  75                  80

Asp Ile Ala Thr Tyr Tyr Cys Gln Gln Trp Ser Ser His Ile Phe Thr
                 85                  90                  95

Phe Gly Gln Gly Thr Lys Val Glu Ile Lys Arg Thr Val Ala Ala Pro
                100                 105                 110

Ser Val Phe Ile Phe Pro Pro Ser Lys Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
        210

<210> SEQ ID NO 37
<211> LENGTH: 217
<212> TYPE: PRT
<213> ORGANISM: Artificial Sequence
<220> FEATURE:
<223> OTHER INFORMATION: Synthetic Construct

<400> SEQUENCE: 37

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
                180                 185                 190

Phe Ser Cys Ser Val Met His Glu Ala Leu His Asn His Tyr Thr Gln
            195                 200                 205

Lys Ser Leu Ser Leu Ser Pro Gly Lys
        210                 215

<210> SEQ ID NO 38
<211> LENGTH: 217
<212> TYPE: PRT
<213> ORGANISM: Artificial Sequence
<220> FEATURE:
<223> OTHER INFORMATION: Synthetic Construct

<400> SEQUENCE: 38

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Met Ser Asp Gly Ser Phe Phe Leu
                165                 170                 175

Ala Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 39
<211> LENGTH: 217
<212> TYPE: PRT
<213> ORGANISM: Artificial Sequence
<220> FEATURE:
<223> OTHER INFORMATION: Synthetic Construct

<400> SEQUENCE: 39

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

```
Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
            115                 120                 125

Thr Asp Asn Gln Val Ser Leu Thr Cys Leu Val Lys Gly Phe Tyr Pro
            130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Met Ser Asp Gly Ser Phe Phe Leu
                165                 170                 175

Ala Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
            210                 215

<210> SEQ ID NO 40
<211> LENGTH: 217
<212> TYPE: PRT
<213> ORGANISM: Artificial Sequence
<220> FEATURE:
<223> OTHER INFORMATION: Synthetic Construct

<400> SEQUENCE: 40

Ala Pro Glu Leu Leu Gly Gly Pro Ser Val Phe Leu Phe Pro Pro Lys
  1               5                  10                  15

Pro Lys Asp Thr Leu Met Ile Ser Arg Thr Pro Glu Val Thr Cys Val
             20                  25                  30

Val Val Asp Val Ser His Glu Asp Pro Glu Val Lys Phe Asn Trp Tyr
         35                  40                  45

Val Asp Gly Val Glu Val His Asn Ala Lys Thr Lys Pro Arg Glu Glu
     50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Ser Thr Leu Pro Pro Ser Arg Glu Glu Met
            115                 120                 125

Thr Lys Asn Gln Val Ser Leu Val Cys Leu Val Tyr Gly Phe Tyr Pro
            130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Val Leu Thr Val Asp Lys Ser Arg Trp Gln Gln Gly Asn Val
            180                 185                 190
```

```
Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 41
<211> LENGTH: 217
<212> TYPE: PRT
<213> ORGANISM: Artificial Sequence
<220> FEATURE:
<223> OTHER INFORMATION: Synthetic Construct

<400> SEQUENCE: 41

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Ser Thr Leu Pro Pro Ser Arg Glu Glu Met
        115                 120                 125

Thr Lys Asn Gln Val Ser Leu Met Cys Leu Val Tyr Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Val Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 42
<211> LENGTH: 217
<212> TYPE: PRT
<213> ORGANISM: Artificial Sequence
<220> FEATURE:
<223> OTHER INFORMATION: Synthetic Construct

<400> SEQUENCE: 42

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
```

```
                        50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Val Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Val Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 43
<211> LENGTH: 217
<212> TYPE: PRT
<213> ORGANISM: Artificial Sequence
<220> FEATURE:
<223> OTHER INFORMATION: Synthetic Construct

<400> SEQUENCE: 43

Ala Pro Glu Leu Leu Gly Gly Pro Ser Val Phe Leu Phe Pro Pro Lys
  1               5                  10                  15

Pro Lys Asp Thr Leu Met Ile Ser Arg Thr Pro Glu Val Thr Cys Val
             20                  25                  30

Val Val Asp Val Ser His Glu Asp Pro Glu Val Lys Phe Asn Trp Tyr
         35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Arg Pro Arg Val Tyr Thr Leu Pro Pro Ser Arg Glu Glu Met
        115                 120                 125

Thr Lys Asn Gln Val Ser Leu Val Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Val Leu Thr Val Asp Lys Ser Arg Trp Gln Gln Gly Asn Val
            180                 185                 190

Phe Ser Cys Ser Val Met His Glu Ala Leu His Asn His Tyr Thr Gln
```

Lys Ser Leu Ser Leu Ser Pro Gly Lys
    210                 215

<210> SEQ ID NO 44
<211> LENGTH: 217
<212> TYPE: PRT
<213> ORGANISM: Artificial Sequence
<220> FEATURE:
<223> OTHER INFORMATION: Synthetic Construct

<400> SEQUENCE: 44

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Asp Met
        115                 120                 125

Thr Lys Asn Gln Val Gln Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Ala Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 45
<211> LENGTH: 217
<212> TYPE: PRT
<213> ORGANISM: Artificial Sequence
<220> FEATURE:
<223> OTHER INFORMATION: Synthetic Construct

<400> SEQUENCE: 45

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Gly Asp Met
        115                 120                 125

Thr Lys Asn Gln Val Gln Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Ala Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 46
<211> LENGTH: 217
<212> TYPE: PRT
<213> ORGANISM: Artificial Sequence
<220> FEATURE:
<223> OTHER INFORMATION: Synthetic Construct

<400> SEQUENCE: 46

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Asp Met
        115                 120                 125

Thr Lys Asn Gln Val Arg Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Ala Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

```
Lys Ser Leu Ser Leu Ser Pro Gly Lys
    210                 215
```

<210> SEQ ID NO 47
<211> LENGTH: 445
<212> TYPE: PRT
<213> ORGANISM: Artificial Sequence
<220> FEATURE:
<223> OTHER INFORMATION: Synthetic Construct

<400> SEQUENCE: 47

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Lys Ala Pro Gly Lys Gly Leu Glu Trp Val
        35                  40                  45

Ala Asp Val Asn Pro Asn Ser Gly Gly Ser Ile Tyr Asn Gln Glu Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val Ala Thr Gly Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Gln Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350
```

```
Ser Gln Glu Glu Met Thr Asp Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Met Ser Asp
385                 390                 395                 400

Gly Ser Phe Phe Leu Ala Ser Arg Leu Thr Val Asp Lys Ser Arg Trp
            405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
            435                 440                 445

<210> SEQ ID NO 48
<211> LENGTH: 445
<212> TYPE: PRT
<213> ORGANISM: Artificial Sequence
<220> FEATURE:
<223> OTHER INFORMATION: Synthetic Construct

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Lys Ala Pro Gly Lys Gly Leu Glu Trp Val
        35                  40                  45

Ala Asp Val Asn Pro Asn Ser Gly Gly Ser Ile Tyr Asn Gln Glu Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val Ala Thr Gly Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270
```

```
Gln Phe Asn Trp Tyr Val Asp Gly Val Glu Val His Asn Ala Lys Thr
            275                 280                 285

Lys Pro Arg Glu Glu Gln Phe Gln Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Ser Thr Leu Pro Pro
            340                 345                 350

Ser Gln Glu Glu Met Thr Lys Asn Gln Val Ser Leu Met Cys Leu Val
            355                 360                 365

Tyr Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Val Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
            435                 440                 445

<210> SEQ ID NO 49
<211> LENGTH: 212
<212> TYPE: PRT
<213> ORGANISM: Artificial Sequence
<220> FEATURE:
<223> OTHER INFORMATION: Synthetic Construct

<400> SEQUENCE: 49

Arg Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Asp Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Tyr Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Trp
                165                 170                 175

Ser Tyr Leu Ser Leu Thr Pro Glu Gln Trp Lys Ser His Arg Ser Tyr
            180                 185                 190
```

```
Ser Cys Gln Val Thr His Glu Gly Ser Thr Val Glu Lys Thr Val Ala
            195                 200                 205

Pro Thr Glu Cys
    210

<210> SEQ ID NO 50
<211> LENGTH: 445
<212> TYPE: PRT
<213> ORGANISM: Artificial Sequence
<220> FEATURE:
<223> OTHER INFORMATION: Synthetic Construct

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Lys Ala Pro Gly Lys Gly Leu Glu Trp Val
            35                  40                  45

Gly Met Ile Asp Pro Ser Asn Ser Asp Thr Arg Phe Asn Pro Glu Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val Ala Thr Gly Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Gln Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335
```

```
Lys Ala Lys Gly Gln Pro Arg Glu Pro Gln Val Tyr Thr Leu Pro Pro
                340                 345                 350

Ser Gln Glu Glu Met Thr Asp Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Met Ser Asp
385                 390                 395                 400

Gly Ser Phe Phe Leu Ala Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
        435                 440                 445

<210> SEQ ID NO 51
<211> LENGTH: 445
<212> TYPE: PRT
<213> ORGANISM: Artificial Sequence
<220> FEATURE:
<223> OTHER INFORMATION: Synthetic Construct

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Lys Ala Pro Gly Lys Gly Leu Glu Trp Val
        35                  40                  45

Gly Met Ile Asp Pro Ser Asn Ser Asp Thr Arg Phe Asn Pro Glu Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val Ala Thr Gly Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255
```

```
Glu Val Thr Cys Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Gln Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Ser Thr Leu Pro Pro
            340                 345                 350

Ser Gln Glu Glu Met Thr Lys Asn Gln Val Ser Leu Met Cys Leu Val
        355                 360                 365

Tyr Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Val Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
        435                 440                 445

<210> SEQ ID NO 52
<211> LENGTH: 218
<212> TYPE: PRT
<213> ORGANISM: Artificial Sequence
<220> FEATURE:
<223> OTHER INFORMATION: Synthetic Construct

<400> SEQUENCE: 52

Arg Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Thr
            20                  25                  30

Ser Ser Gln Lys Asn Tyr Leu Ala Trp Tyr Gln Asp Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys Gly Gln Pro Lys Ala Ala Pro Ser Val Thr Leu Phe Pro Pro Ser
        115                 120                 125

Ser Glu Glu Leu Gln Ala Asn Lys Ala Thr Leu Val Cys Tyr Ile Ser
    130                 135                 140

Asp Phe Tyr Pro Gly Ala Val Thr Val Ala Trp Lys Ala Asp Ser Ser
145                 150                 155                 160

Pro Val Lys Ala Gly Val Glu Thr Thr Thr Pro Ser Lys Gln Ser Asn
                165                 170                 175
```

-continued

```
Asn Lys Tyr Ala Ala Trp Ser Tyr Leu Ser Leu Thr Pro Glu Gln Trp
            180                 185                 190

Lys Ser His Arg Ser Tyr Ser Cys Gln Val Thr His Glu Gly Ser Thr
        195                 200                 205

Val Glu Lys Thr Val Ala Pro Thr Glu Cys
    210                 215

<210> SEQ ID NO 53
<211> LENGTH: 447
<212> TYPE: PRT
<213> ORGANISM: Artificial Sequence
<220> FEATURE:
<223> OTHER INFORMATION: Synthetic Construct

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Tyr Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Asp Tyr Gly
    210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Gln Ser Thr Tyr Arg Val Val
    290                 295                 300

Ser Val Leu Thr Val Leu His Gln Asp Trp Leu Asn Gly Lys Glu Tyr
305                 310                 315                 320
```

```
Lys Cys Lys Val Ser Asn Lys Gly Leu Pro Ser Ser Ile Glu Lys Thr
                325                 330                 335

Ile Ser Lys Ala Lys Gly Gln Pro Arg Arg Pro Arg Val Tyr Thr Leu
            340                 345                 350

Pro Pro Ser Gln Glu Glu Met Thr Lys Asn Gln Val Ser Leu Val Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Val Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly
        435                 440                 445

<210> SEQ ID NO 54
<211> LENGTH: 447
<212> TYPE: PRT
<213> ORGANISM: Artificial Sequence
<220> FEATURE:
<223> OTHER INFORMATION: Synthetic Construct

<400> SEQUENCE: 54

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Tyr Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Asp Tyr Gly
    210                 215                 220

Pro Pro Cys Pro Pro Cys Pro Ala Pro Glu Ala Ala Gly Gly Pro Ser
225                 230                 235                 240
```

```
Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Gln Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Gly Asp Met Thr Lys Asn Gln Val Gln Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Ala Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly
            435                 440                 445

<210> SEQ ID NO 55
<211> LENGTH: 213
<212> TYPE: PRT
<213> ORGANISM: Artificial Sequence
<220> FEATURE:
<223> OTHER INFORMATION: Synthetic Construct

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Thr Tyr Met
            20                  25                  30

Tyr Trp Tyr Gln Arg Lys Pro Gly Asp Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser His Ile Phe Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Lys Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160
```

-continued

```
Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
        180                 185                 190

Cys Glu Val Thr His Gln Gly Leu Ser Ser Pro Val Thr Lys Ser Phe
        195                 200                 205

Asn Arg Gly Glu Cys
210

<210> SEQ ID NO 56
<211> LENGTH: 442
<212> TYPE: PRT
<213> ORGANISM: Artificial Sequence
<220> FEATURE:
<223> OTHER INFORMATION: Synthetic Construct

<400> SEQUENCE: 56

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Tyr Leu His Trp Val Arg Tyr Ala Pro Gly Gln Gly Leu Glu Trp Met
        35                  40                  45

Gly Trp Ile Tyr Pro Gly Asn Val His Ala Gln Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Glu Gly Phe Pro Tyr Trp Gly Arg Gly Thr Thr Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Asp Tyr Gly Pro Pro Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Gln Ser Thr Tyr Arg Val Val Ser Val Leu Thr Val
    290                 295                 300
```

```
Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
            325                 330                 335

Gly Gln Pro Arg Arg Pro Arg Val Tyr Thr Leu Pro Pro Ser Gln Glu
        340                 345                 350

Glu Met Thr Lys Asn Gln Val Ser Leu Val Cys Leu Val Lys Gly Phe
    355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Val Leu Thr Val Asp Lys Ser Arg Trp Gln Glu Gly
            405                 410                 415

Asn Val Phe Ser Cys Ser Val Met His Glu Ala Leu His Asn His Tyr
            420                 425                 430

Thr Gln Lys Ser Leu Ser Leu Ser Leu Gly
            435                 440
```

<210> SEQ ID NO 57
<211> LENGTH: 442
<212> TYPE: PRT
<213> ORGANISM: Artificial Sequence
<220> FEATURE:
<223> OTHER INFORMATION: Synthetic Construct

<400> SEQUENCE: 57

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Tyr Leu His Trp Val Arg Tyr Ala Pro Gly Gln Gly Leu Glu Trp Met
        35                  40                  45

Gly Trp Ile Tyr Pro Gly Asn Val His Ala Gln Tyr Asn Glu Lys Phe
50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Ser Trp Glu Gly Phe Pro Tyr Trp Gly Arg Gly Thr Thr Val
        100                 105                 110

Thr Val Ser Ser Ala Ser Thr Lys Gly Pro Ser Val Phe Pro Leu Ala
    115                 120                 125

Pro Cys Ser Arg Ser Thr Ser Glu Ser Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Lys Thr Tyr Thr Cys Asn Val Asp His Lys Pro Ser Asn Thr
    195                 200                 205

Lys Val Asp Lys Arg Val Glu Ser Asp Tyr Gly Pro Pro Cys Pro Pro
210                 215                 220
```

```
Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser Gln Glu Asp Pro Glu Val Gln Phe Asn
        260                 265                 270

Trp Tyr Val Asp Gly Val Glu Val His Asn Ala Lys Thr Lys Pro Arg
    275                 280                 285

Glu Glu Gln Phe Gln Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Gly
            340                 345                 350

Asp Met Thr Lys Asn Gln Val Gln Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Ala Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly
        435                 440

<210> SEQ ID NO 58
<211> LENGTH: 214
<212> TYPE: PRT
<213> ORGANISM: Artificial Sequence
<220> FEATURE:
<223> OTHER INFORMATION: Synthetic Construct

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Ile Asn
            20                  25                  30

Val Ala Trp Tyr Gln Arg Lys Pro Gly Asp Ala Pro Lys Ser Leu Ile
        35                  40                  45

Ser Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Phe Cys Gln Gln Tyr Asp Thr Tyr Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Lys Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 59
<211> LENGTH: 217
<212> TYPE: PRT
<213> ORGANISM: Artificial Sequence
<220> FEATURE:
<223> OTHER INFORMATION: Synthetic Construct

<400> SEQUENCE: 59

```
Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Lys
    210                 215
```

<210> SEQ ID NO 60
<211> LENGTH: 217
<212> TYPE: PRT
<213> ORGANISM: Artificial Sequence
<220> FEATURE:
<223> OTHER INFORMATION: Synthetic Construct

<400> SEQUENCE: 60

```
Ala Pro Glu Phe Leu Gly Gly Pro Ser Val Phe Leu Phe Pro Pro Lys
1               5                   10                  15
```

```
Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Ala Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Lys
    210                 215

<210> SEQ ID NO 61
<211> LENGTH: 217
<212> TYPE: PRT
<213> ORGANISM: Artificial Sequence
<220> FEATURE:
<223> OTHER INFORMATION: Synthetic Construct

<400> SEQUENCE: 61

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160
```

Tyr Lys Thr Thr Pro Pro Val Leu Met Ser Asp Gly Ser Phe Phe Leu
            165                 170                 175

Ala Ser Arg Leu Thr Val Asp Lys Ser Arg Trp Gln Glu Gly Asn Val
        180                 185                 190

Phe Ser Cys Ser Val Met His Glu Ala Leu His Asn His Tyr Thr Gln
        195                 200                 205

Lys Ser Leu Ser Leu Ser Leu Gly Lys
    210                 215

<210> SEQ ID NO 62
<211> LENGTH: 217
<212> TYPE: PRT
<213> ORGANISM: Artificial Sequence
<220> FEATURE:
<223> OTHER INFORMATION: Synthetic Construct

<400> SEQUENCE: 62

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
            85                  90                  95

Gly Leu Pro Ser Ser Ile Glu Lys Thr Ile Ser Lys Ala Lys Gly Gln
        100                 105                 110

Pro Arg Glu Pro Gln Val Tyr Thr Leu Pro Pro Ser Gln Glu Glu Met
    115                 120                 125

Thr Asp Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Met Ser Asp Gly Ser Phe Phe Leu
            165                 170                 175

Ala Ser Arg Leu Thr Val Asp Lys Ser Arg Trp Gln Glu Gly Asn Val
        180                 185                 190

Phe Ser Cys Ser Val Met His Glu Ala Leu His Asn His Tyr Thr Gln
        195                 200                 205

Lys Ser Leu Ser Leu Ser Leu Gly Lys
    210                 215

<210> SEQ ID NO 63
<211> LENGTH: 217
<212> TYPE: PRT
<213> ORGANISM: Artificial Sequence
<220> FEATURE:
<223> OTHER INFORMATION: Synthetic Construct

<400> SEQUENCE: 63

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val

-continued

```
                    20                  25                  30
Val Val Asp Val Ser Gln Glu Asp Pro Glu Val Gln Phe Asn Trp Tyr
                35                  40                  45
Val Asp Gly Val Glu Val His Asn Ala Lys Thr Lys Pro Arg Glu Glu
         50                  55                  60
Gln Phe Asn Ser Thr Tyr Arg Val Val Ser Val Leu Thr Val Leu His
 65                  70                  75                  80
Gln Asp Trp Leu Asn Gly Lys Glu Tyr Lys Cys Lys Val Ser Asn Lys
                 85                  90                  95
Gly Leu Pro Ser Ser Ile Glu Lys Thr Ile Ser Lys Ala Lys Gly Gln
            100                 105                 110
Pro Arg Glu Pro Gln Val Ser Thr Leu Pro Pro Ser Gln Glu Glu Met
        115                 120                 125
Thr Lys Asn Gln Val Ser Leu Val Cys Leu Val Tyr Gly Phe Tyr Pro
    130                 135                 140
Ser Asp Ile Ala Val Glu Trp Glu Ser Asn Gly Gln Pro Glu Asn Asn
145                 150                 155                 160
Tyr Lys Thr Thr Pro Pro Val Leu Asp Ser Asp Gly Ser Phe Phe Leu
                165                 170                 175
Tyr Ser Val Leu Thr Val Asp Lys Ser Arg Trp Gln Glu Gly Asn Val
            180                 185                 190
Phe Ser Cys Ser Val Met His Glu Ala Leu His Asn His Tyr Thr Gln
        195                 200                 205
Lys Ser Leu Ser Leu Ser Leu Gly Lys
    210                 215

<210> SEQ ID NO 64
<211> LENGTH: 217
<212> TYPE: PRT
<213> ORGANISM: Artificial Sequence
<220> FEATURE:
<223> OTHER INFORMATION: Synthetic Construct

<400> SEQUENCE: 64

Ala Pro Glu Phe Leu Gly Gly Pro Ser Val Phe Leu Phe Pro Pro Lys
 1               5                  10                  15
Pro Lys Asp Thr Leu Met Ile Ser Arg Thr Pro Glu Val Thr Cys Val
                20                  25                  30
Val Val Asp Val Ser Gln Glu Asp Pro Glu Val Gln Phe Asn Trp Tyr
            35                  40                  45
Val Asp Gly Val Glu Val His Asn Ala Lys Thr Lys Pro Arg Glu Glu
         50                  55                  60
Gln Phe Asn Ser Thr Tyr Arg Val Val Ser Val Leu Thr Val Leu His
 65                  70                  75                  80
Gln Asp Trp Leu Asn Gly Lys Glu Tyr Lys Cys Lys Val Ser Asn Lys
                 85                  90                  95
Gly Leu Pro Ser Ser Ile Glu Lys Thr Ile Ser Lys Ala Lys Gly Gln
            100                 105                 110
Pro Arg Glu Pro Gln Val Ser Thr Leu Pro Pro Ser Gln Glu Glu Met
        115                 120                 125
Thr Lys Asn Gln Val Ser Leu Met Cys Leu Val Tyr Gly Phe Tyr Pro
    130                 135                 140
Ser Asp Ile Ala Val Glu Trp Glu Ser Asn Gly Gln Pro Glu Asn Asn
145                 150                 155                 160
Tyr Lys Thr Thr Pro Pro Val Leu Asp Ser Asp Gly Ser Phe Phe Leu
```

```
                165                 170                 175
Tyr Ser Val Leu Thr Val Asp Lys Ser Arg Trp Gln Glu Gly Asn Val
            180                 185                 190

Phe Ser Cys Ser Val Met His Glu Ala Leu His Asn His Tyr Thr Gln
            195                 200                 205

Lys Ser Leu Ser Leu Ser Leu Gly Lys
        210                 215

<210> SEQ ID NO 65
<211> LENGTH: 217
<212> TYPE: PRT
<213> ORGANISM: Artificial Sequence
<220> FEATURE:
<223> OTHER INFORMATION: Synthetic Construct

<400> SEQUENCE: 65

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Val Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Val Leu Thr Val Asp Lys Ser Arg Trp Gln Glu Gly Asn Val
            180                 185                 190

Phe Ser Cys Ser Val Met His Glu Ala Leu His Asn His Tyr Thr Gln
            195                 200                 205

Lys Ser Leu Ser Leu Ser Leu Gly Lys
        210                 215

<210> SEQ ID NO 66
<211> LENGTH: 217
<212> TYPE: PRT
<213> ORGANISM: Artificial Sequence
<220> FEATURE:
<223> OTHER INFORMATION: Synthetic Construct

<400> SEQUENCE: 66

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30
```

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
 50                  55                  60

Gln Phe Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Gly Leu Pro Ser Ser Ile Glu Lys Thr Ile Ser Lys Ala Lys Gly Gln
            100                 105                 110

Pro Arg Arg Pro Arg Val Tyr Thr Leu Pro Pro Ser Gln Glu Glu Met
        115                 120                 125

Thr Lys Asn Gln Val Ser Leu Val Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Val Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Lys
    210                 215

<210> SEQ ID NO 67
<211> LENGTH: 217
<212> TYPE: PRT
<213> ORGANISM: Artificial Sequence
<220> FEATURE:
<223> OTHER INFORMATION: Synthetic Construct

<400> SEQUENCE: 67

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
 50                  55                  60

Gln Phe Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Asp Met
        115                 120                 125

Thr Lys Asn Gln Val Gln Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

```
Ala Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
            195                 200                 205

Lys Ser Leu Ser Leu Ser Leu Gly Lys
            210                 215

<210> SEQ ID NO 68
<211> LENGTH: 217
<212> TYPE: PRT
<213> ORGANISM: Artificial Sequence
<220> FEATURE:
<223> OTHER INFORMATION: Synthetic Construct

<400> SEQUENCE: 68

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Gly Asp Met
        115                 120                 125

Thr Lys Asn Gln Val Gln Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Ala Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
            195                 200                 205

Lys Ser Leu Ser Leu Ser Leu Gly Lys
            210                 215

<210> SEQ ID NO 69
<211> LENGTH: 217
<212> TYPE: PRT
<213> ORGANISM: Artificial Sequence
<220> FEATURE:
<223> OTHER INFORMATION: Synthetic Construct

<400> SEQUENCE: 69

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45
```

```
Val Asp Gly Val Glu Val His Asn Ala Lys Thr Lys Pro Arg Glu Glu
    50              55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Asp Met
        115                 120                 125

Thr Lys Asn Gln Val Arg Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Ala Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Lys
    210                 215
```

IGG BISPECIFIC ANTIBODIES AND PROCESSES FOR PREPARATION

CROSS-REFERENCE OF RELATED APPLICATIONS

This application is a national stage entry of the PCT Patent Application PCT/US2016/014313 filed on Jan. 21, 2016, which claims priority to and the benefit under 35 U.S.C. 119(e) to U.S. Provisional Patent Application No. 62/106,494, filed on Jan. 22, 2015.

BACKGROUND OF THE INVENTION

Antibody therapies represent an ever increasing segment of the global pharmaceutical market. Approved antibody-based products include treatments for cancer, autoimmune disorders (e.g. rheumatoid arthritis), infectious diseases, cardiovascular disease and many other disorders. However, to improve patient outcomes, perturbation of multiple therapeutic targets or biochemical pathways is often desired. In this context, antibody therapy has limitations.

Co-administration of two or more antibody therapies requires multiple injections or, alternatively, a single injection of a co-formulation of two different antibody compositions. While multiple injections permit flexibility in dose and timing of administration, the inconvenience and discomfort associated with multiple injections may reduce patient compliance. While a co-formulation of multiple antibody agents would permit fewer injections, the difficulty and/or expense associated with designing a suitable pharmaceutical formulation that provides the necessary stability and bioavailability, for each antibody ingredient, may be prohibitive. Further, any treatment regime which entails administration of separate antibody agents will incur added manufacturing and regulatory costs associated with the development of each individual agent.

Bispecific antibodies (BsAbs)—single agents capable of binding to two distinct antigens or epitopes—have been proposed as a means for addressing the limitations attendant with co-administration or co-formulation of separate antibody agents. BsAbs integrate the binding activities of two separate antibody therapeutics into a single agent, thus providing a potential cost and convenience benefit to the patient. In some circumstances, BsAbs may also elicit synergistic or novel activities beyond what an antibody combination can achieve.

Recombinant DNA technologies have enabled the generation of multiple BsAb formats. For example, single chain Fv (scFv) fragments composed of antigen recognition domains (i.e., heavy chain variable ($V_H$) and light chain variable ($V_L$) domains) tethered by flexible or structured linkers, taken from existing monoclonal antibody (MAb) therapeutics or discovered by in vitro screening methodologies, have been used as building blocks for BsAb generation. In this context, an scFv fragment(s) which binds a particular antigen can be linked to another moiety, for example a separate scFv or an IgG MAb which binds a separate antigen, to form multi-valent BsAb. However, a limitation with the use of scFvs is that they lack the archetypical Fab architecture which provides stabilizing interactions of the heavy chain (HC) and light chain (LC) constant domains (i.e., $C_H1$ and $C_L$, respectively) which can improve thermal stability or solubility, or reduce the potential for aggregation.

The ability to generate bispecific antibodies retaining the full IgG antibody architecture has long been a challenge in the field of antibody engineering. One approach for generating fully IgG bispecific antibodies entails co-expression of nucleic acids encoding two distinct HC-LC pairs which, when expressed, assemble to form a single antibody comprising two distinct Fabs. However, to achieve efficiency in manufacturing, each of the expressed polypeptides of the distinct HC-LC pairs must assemble with its cognate polypeptide with good specificity to reduce generation of mismatched Fab by-products. In addition, the two distinct HCs must heterodimerize in assembly to reduce generation of mono-specific antibody by-products. Fab interface designs which promote assembly of particular HC-LC pairs have recently been described. (See Lewis, et al. (2014), *Nat. Biotechnol.*, 32; 191-198; and Published PCT Applications WO2014/150973 and WO2014/0154254) in addition, procedures for directing assembly of particular HC-HC pairs by introducing modifications into regions of the HC-HC interface have also been disclosed in the art. (See Klein et al., *mAbs;* 4(6); 1-11 (2012); Carter et al., *J. Immunol. Methods;* 248; 7-15 (2001); Gunasekaran, et al, *J. Biol. Chem.;* 285; 19637-19646 (2010); Zhu et al., *Protein Sci.;* 6: 781-788 (1997); and Igawa et al., *Protein Eng. Des. Sel.;* 23; 667-677 (2010)). However, there remains a need for alternative methods for generating fully IgG BsAbs.

DETAILED DESCRIPTION

In accordance with the present invention, HC-HC interface designs and processes have been identified for improving assembly of fully IgG bispecific antibodies. The designs and processes of the present invention achieve improved heterodimerization of distinct heavy chains by introducing specific mutations in the $C_H3$ domain of IgG1, IgG2 or IgG4 constant regions, and may be combined with known methods for improving HC-LC specific assembly, thus facilitating assembly of fully IgG BsAbs. In particular, the present invention provides an IgG bispecific antibody comprising: (a) a first heavy chain, wherein said first heavy chain comprises a first variable domain ($V_H$) and a first human IgG1 or IgG4 constant region, wherein said first human IgG1 or IgG4 constant region comprises an alanine substituted at residue 407 (or an alanine at residue 407) of the $C_H3$ domain; (b) a first light chain, wherein said first light chain comprises a first variable domain ($V_L$) and a first constant domain ($C_L$); (c) a second heavy chain, wherein said second heavy chain comprises a second variable domain ($V_H$) and a second human IgG1 or IgG4 constant region, wherein said second human IgG1 or IgG4 constant region comprises a valine or methionine substituted at residue 366 (or a valine or methionine at residue 366) and a valine substituted at residue 409 (or a valine at residue 409) of the $C_H3$ domain; and (d) a second light chain, wherein said second light chain comprises a second variable domain ($V_L$) and a second constant domain ($C_L$).

More particularly, the present invention provides an IgG bispecific antibody comprising: (a) a first heavy chain, wherein said first heavy chain comprises a first variable domain ($V_H$) and a first human IgG1 or IgG4 constant region, wherein said first human IgG1 or IgG4 constant region comprises an alanine substituted at residue 407 (or an alanine at residue 407) of the $C_H3$ domain; (h) a first light chain, wherein said first light chain comprises a first variable domain ($V_L$) and a first constant domain ($C_L$); (c) a second heavy chain, wherein said second heavy chain comprises a second variable domain ($V_H$) and a second human IgG1 or IgG4 constant region, wherein said second human IgG1 or IgG4 constant region comprises a valine substituted at residue 366 (or a valine at residue 366) and a valine substituted at residue 409 (or a valine at residue 409) of the $C_H3$ domain; and (d) a second light chain, wherein said second light chain comprises a second variable domain ($V_L$) and a second constant domain ($C_L$).

More particularly, the present invention provides an IgG bispecific antibody comprising: (a) a first heavy chain, wherein said first heavy chain comprises a first variable domain ($V_H$) and a first human IgG1 constant region, wherein said first human IgG1 or IgG4 constant region comprises an alanine substituted at residue 407 (or an alanine at residue 407) and a methionine substituted at residue 399 (or a methionine at residue 399) of the $C_H3$ domain; (b) a first light chain, wherein said first light chain comprises a first variable domain ($V_L$) and a first constant domain ($C_L$); (c) a second heavy chain, wherein said second heavy chain comprises a second variable domain ($V_H$) and a second human IgG1 or IgG4 constant region, wherein said second human IgG1 or IgG4 constant region comprises a valine substituted at residue 366 (or a valine at residue 366) and a valine substituted at residue 409 (or a valine at residue 409) of the $C_H3$ domain; and (d) a second light chain, wherein said second light chain comprises a second variable domain ($V_L$) and a second constant domain ($C_L$).

More particularly, the present invention provides an IgG bispecific antibody comprising: (a) a first heavy chain, wherein said first heavy chain comprises a first variable domain ($V_H$) and a first human IgG1 or IgG4 constant region, wherein said first human IgG1 or IgG4 constant region comprises an alanine substituted at residue 407 (or an alanine at residue 407), a methionine substituted at residue 399 (or a methionine at residue 399) and an aspartic acid substituted at residue 360 (or an aspartic acid at residue 360) of the $C_H3$ domain; (b) a first light chain, wherein said first light chain comprises a first variable domain ($V_L$) and a first constant domain ($C_L$); (c) a second heavy chain, wherein said second heavy chain comprises a second variable domain ($V_H$) and a second human IgG1 or IgG4 constant region, wherein said second human IgG1 or IgG4 constant region comprises a valine substituted at residue 366 (or a valine at residue 366), a valine substituted at residue 409 (or a valine at residue 409), and an arginine substituted at residues 345 and 347 (or an arginine at residues 345 and 347) of the $C_H3$ domain; and (d) a second light chain, wherein said second light chain comprises a second variable domain ($V_L$) and a second constant domain ($C_L$).

As another particular embodiment, the present invention provides an IgG bispecific antibody comprising: (a) a first heavy chain, wherein said first heavy chain comprises a first variable domain ($V_H$) and a first human IgG1 or IgG4 constant region, wherein said first human IgG1 or IgG4 constant region comprises an aspartic acid substituted at residue 357 (or an aspartic acid at residue 357), a glutamine substituted at residue 364 (or a glutamine at residue 364) and an alanine substituted at residue 407 (or an alanine at residue 407) of the $C_H3$ domain; (b) a first light chain, wherein said first light chain comprises a first variable domain ($V_L$) and a first constant domain ($C_L$); (c) a second heavy chain, wherein said second heavy chain comprises a second variable domain ($V_H$) and a second human IgG1 or IgG4 constant region, wherein said second human IgG1 or IgG4 constant region comprises a serine substituted at residue 349 (or a serine at residue 349), a valine substituted at residue 366 (or a valine at residue 366), a tyrosine substituted at residue 370 (or a tyrosine at residue 370) and a valine substituted at residue 409 (or a valine at residue 409) of the $C_H3$ domain; and (d) a second light chain, wherein said second light chain comprises a second variable domain ($V_L$) and a second constant domain ($C_L$).

Another particular embodiment of the present invention provides an IgG bispecific antibody comprising: (a) a first heavy chain, wherein said first heavy chain comprises a first variable domain ($V_H$) and a first human IgG1 or IgG4 constant region, wherein said first human IgG1 or IgG4 constant region comprises an aspartic acid substituted at residue 357 (or an aspartic acid at residue 357), a glutamine substituted at residue 364 (or a glutamine at residue 364) and an alanine substituted at residue 407 (or an alanine at residue 407) of the $C_H3$ domain; (b) a first light chain, wherein said first light chain comprises a first variable domain ($V_L$) and a first constant domain ($C_L$); (c) a second heavy chain, wherein said second heavy chain comprises a second variable domain ($V_H$) and a second human IgG1 or IgG4 constant region, wherein said second human IgG1 or IgG4 constant region comprises a serine substituted at residue 349 (or a serine at residue 349), a methionine substituted at residue 366 (or a methionine at residue 366), a tyrosine substituted at residue 370 (or a tyrosine at residue 370) and a valine substituted at residue 409 (or a valine at residue 409) of the $C_H3$ domain; and (d) a second light chain, wherein said second light chain comprises a second variable domain ($V_L$) and a second constant domain ($C_L$).

The present invention further provides an IgG bispecific antibody comprising: (a) a first heavy chain, wherein said first heavy chain comprises a first variable domain ($V_H$) and a first human IgG1 or IgG4 constant region, wherein said first human IgG1 or IgG4 constant region comprises an aspartic acid substituted at residue 357 (or an aspartic acid at residue 357), an arginine substituted at residue 364 (or an arginine at residue 364) and an alanine substituted at residue 407 (or an alanine at residue 407) of the $C_H3$ domain; (b) a first light chain, wherein said first light chain comprises a first variable domain ($V_L$) and a first constant domain ($C_L$); (c) a second heavy chain, wherein said second heavy chain comprises a second variable domain ($V_H$) and a second human IgG1 or IgG4 constant region, wherein said second human IgG1 or IgG4 constant region comprises a serine substituted at residue 349 (or a serine at residue 349), a valine substituted at residue 366 (or a valine at residue 366), a tyrosine substituted at residue 370 (or a tyrosine at residue 370) and a valine substituted at residue 409 (or a valine at residue 409) of the $C_H3$ domain; and (d) a second light chain, wherein said second light chain comprises a second variable domain ($V_L$) and a second constant domain ($C_L$).

Yet another particular embodiment provides an IgG bispecific antibody comprising: (a) a first heavy chain, wherein said first heavy chain comprises a first variable domain ($V_H$) and a first human IgG1 or IgG4 constant region, wherein said first human IgG1 or IgG4 constant region comprises a glycine substituted at residue 356 (or a glycine at residue 356), an aspartic acid substituted at residue 357 (or an aspartic acid at residue 357), a glutamine substituted at residue 364 (or a glutamine at residue 364) and an alanine substituted at residue 407 (or an alanine at residue 407) of the $C_H3$ domain; (b) a first light chain, wherein said first light chain comprises a first variable domain ($V_L$) and a first constant domain ($C_L$); (c) a second heavy chain, wherein said second heavy chain comprises a second variable domain ($V_H$) and a second human IgG1 or IgG4 constant region, wherein said second human IgG1 or IgG4 constant region comprises a serine substituted at residue 349 (or a serine at residue 349), a valine substituted at residue 366 (or a valine at residue 366), a tyrosine substituted at residue 370 (or a tyrosine at residue 370) and a valine substituted at residue 409 (or a valine at residue 409) of the $C_H3$ domain; and (d) a second light chain, wherein said second light chain comprises a second variable domain ($V_L$) and a second constant domain ($C_L$).

The present invention further provides an IgG bispecific antibody comprising: (a) a first heavy chain, wherein said first heavy chain comprises a first variable domain ($V_H$) and a first human IgG1 or IgG4 constant region, wherein said first human IgG1 or IgG4 constant region comprises a glycine substituted at residue 356 (or a glycine at residue 356), an aspartic acid substituted at residue 357 (or an aspartic acid at residue 357), a glutamine substituted at residue 364 (or a glutamine at residue 364) and an alanine substituted at residue 407 (or an alanine at residue 407) of the $C_H3$ domain; (b) a first light chain, wherein said first light chain comprises a first variable domain ($V_L$) and a first constant domain ($C_L$); (c) a second heavy chain, wherein said second heavy chain comprises a second variable domain ($V_H$) and a second human IgG1 or IgG4 constant region, wherein said second human IgG1 or IgG4 constant region comprises a serine substituted at residue 349 (or a serine at residue 349), a methionine substituted at residue 366 (or a methionine at residue 366), a tyrosine substituted at residue 370 (or a tyrosine at residue 370) and a valine substituted at residue 409 (or a valine at residue 409) of the $C_H3$ domain; and (d) a second light chain, wherein said second light chain comprises a second variable domain ($V_L$) and a second constant domain ($C_L$).

As another particular embodiment, the present invention provides an IgG bispecific antibody comprising: (a) a first heavy chain, wherein said first heavy chain comprises a first variable domain ($V_H$) and a first human IgG1 or IgG4 constant region, wherein said first human IgG1 or IgG4 constant region comprises an aspartic acid substituted at residue 357 (or an aspartic acid at residue 357), an arginine substituted at residue 364 (or an arginine at residue 364) and an alanine substituted at residue 407 (or an alanine at residue 407) of the $C_H3$ domain; (b) a first light chain, wherein said first light chain comprises a first variable domain ($V_L$) and a first constant domain ($C_L$); (c) a second heavy chain, wherein said second heavy chain comprises a second variable domain ($V_H$) and a second human IgG1 or IgG4 constant region, wherein said second human IgG1 or IgG4 constant region comprises a serine substituted at residue 349 (or a serine at residue 349), a methionine substituted at residue 366 (or a methionine at residue 366), a tyrosine substituted at residue 370 (or a tyrosine at residue 370) and a valine substituted at residue 409 (or a valine at residue 409) of the $C_H3$ domain; and (d) a second light chain, wherein said second light chain comprises a second variable domain ($V_L$) and a second constant domain ($C_L$).

As additional particular embodiments of the present invention, IgG BsAbs are provided which comprise first and second heavy chains comprising human IgG1 or human IgG4 constant regions, wherein each of said human IgG1 or human IgG4 constant regions comprise $C_H2$-$C_H3$ segments of a particular amino acid sequence. Thus, the present invention provides an IgG bispecific antibody comprising: (a) a first heavy chain, wherein said first heavy chain comprises a first variable domain ($V_H$) and a first human IgG1 constant region, wherein said first human IgG1 constant region comprises an amino acid sequence as given by SEQ ID NO:7; (b) a first light chain, wherein said first light chain comprises a first variable domain ($V_L$) and a first constant domain ($C_L$); (c) a second heavy chain, wherein said second heavy chain comprises a second variable domain ($V_H$) and a second human IgG1 constant region, wherein said second human IgG1 constant region comprises an amino acid sequence as given by SEQ ID NO:42; and (d) a second light chain, wherein said second light chain comprises a second variable domain ($V_L$) and a second constant domain ($C_L$).

As another particular embodiment, the present invention provides an IgG bispecific antibody comprising: (a) a first heavy chain, wherein said first heavy chain comprises a first variable domain ($V_H$) and a first human IgG1 constant region, wherein said first human IgG1 constant region comprises an amino acid sequence as given by SEQ ID NO:38; (b) a first light chain, wherein said first light chain comprises a first variable domain ($V_L$) and a first constant domain ($C_L$); (c) a second heavy chain, wherein said second heavy chain comprises a second variable domain ($V_H$) and a second human IgG1 constant region, wherein said second human IgG1 constant region comprises an amino acid sequence as given by SEQ ID NO:42; and (d) a second light chain, wherein said second light chain comprises a second variable domain ($V_L$) and a second constant domain ($C_L$).

The present invention also provides an IgG bispecific antibody comprising: (a) a first heavy chain, wherein said first heavy chain comprises a first variable domain ($V_H$) and a first human IgG1 constant region, wherein said first human IgG1 constant region comprises an amino acid sequence as given by SEQ ID NO:39; (b) a first light chain, wherein said first light chain comprises a first variable domain ($V_L$) and a first constant domain ($C_L$); (c) a second heavy chain, wherein said second heavy chain comprises a second variable domain ($V_H$) and a second human IgG1 constant region, wherein said second human IgG1 constant region comprises an amino acid sequence as given by SEQ ID NO:43; and (d) a second light chain, wherein said second light chain comprises a second variable domain ($V_L$) and a second constant domain ($C_L$).

As another particular embodiment, the present invention provides an IgG bispecific antibody comprising: (a) a first heavy chain, wherein said first heavy chain comprises a first variable domain ($V_H$) and a first human IgG1 constant region, wherein said first human IgG1 constant region comprises an amino acid sequence as given by SEQ ID NO:40; (b) a first light chain, wherein said first light chain comprises a first variable domain ($V_L$) and a first constant domain ($C_L$); (c) a second heavy chain, wherein said second heavy chain comprises a second variable domain ($V_H$) and a second human IgG1 constant region, wherein said second human IgG1 constant region comprises an amino acid sequence as given by SEQ ID NO:44; and (d) a second light chain, wherein said second light chain comprises a second variable domain ($V_L$), and a second constant domain ($C_L$).

As another particular embodiment, the present invention provides an IgG bispecific antibody comprising: (a) a first heavy chain, wherein said first heavy chain comprises a first variable domain ($V_H$) and a first human IgG1 constant region, wherein said first human IgG1 constant region comprises an amino acid sequence as given by SEQ ID NO:41; (b) a first light chain, wherein said first light chain comprises a first variable domain ($V_L$), and a first constant domain ($C_L$); (c) a second heavy chain, wherein said second heavy chain comprises a second variable domain ($V_H$) and a second human IgG1 constant region, wherein said second human IgG1 constant region comprises an amino acid sequence as given by SEQ ID NO:44; and (d) a second light chain, wherein said second light chain comprises a second variable domain ($V_L$), and a second constant domain ($C_L$).

Yet another particular embodiment provides an IgG bispecific antibody comprising: (a) a first heavy chain, wherein said first heavy chain comprises a first variable domain ($V_H$) and a first human IgG1 constant region, wherein said first human IgG1 constant region comprises an amino acid sequence as given by SEQ ID NO:40; (b) a first light chain, wherein said first light chain comprises a first variable domain ($V_L$) and a first constant domain ($C_L$); (c) a second heavy chain, wherein said second heavy chain comprises a second variable domain ($V_H$) and a second human IgG1 constant region, wherein said second human IgG1 constant region comprises an amino acid sequence as given by SEQ ID NO:46; and (d) a second light chain, wherein said second light chain comprises a second variable domain ($V_L$) and a second constant domain ($C_L$).

The present invention also provides an IgG bispecific antibody comprising: (a) a first heavy chain, wherein said first heavy chain comprises a first variable domain ($V_H$) and a first human IgG1 constant region, wherein said first human IgG1 constant region comprises an amino acid sequence as given by SEQ NO:40; (b) a first light chain, wherein said first light chain comprises a first variable domain ($V_L$) and a first constant domain ($C_L$); (c) a second heavy chain, wherein said second heavy chain comprises a second variable domain ($V_H$) and a second human IgG1 constant region, wherein said second human IgG1 constant region comprises an amino acid sequence as given by SEQ ID NO:45; and (d) a second light chain, wherein said second light chain comprises a second variable domain ($V_L$) and a second constant domain ($C_L$).

Another embodiment provides an IgG bispecific antibody comprising: (a) a first heavy chain, wherein said first heavy chain comprises a first variable domain ($V_H$) and a first human IgG1 constant region, wherein said first human IgG1 constant region comprises an amino acid sequence as given by SEQ ID NO:41; (b) a first light chain, wherein said first light chain comprises a first variable domain ($V_L$) and a first constant domain ($C_L$); (c) a second heavy chain, wherein said second heavy chain comprises a second variable domain ($V_H$) and a second human IgG1 constant region, wherein said second human IgG1 constant region comprises an amino acid sequence as given by SEQ ID NO:45; and (d) a second light chain, wherein said second light chain comprises a second variable domain ($V_L$) and a second constant domain ($C_L$).

Further, the present invention also provides an IgG bispecific antibody comprising: (a) a first heavy chain, wherein said first heavy chain comprises a first variable domain ($V_H$) and a first human IgG1 constant region, wherein said first human IgG1 constant region comprises an amino acid sequence as given by SEQ ID NO:41; (b) a first light chain, wherein said first light chain comprises a first variable domain ($V_L$) and a first constant domain ($C_L$); (c) a second heavy chain, wherein said second heavy chain comprises a second variable domain ($V_H$) and a second human IgG1 constant region, wherein said second human IgG1 constant region comprises an amino acid sequence as given by SEQ ID NO:46; and (d) a second light chain, wherein said second light chain comprises a second variable domain ($V_L$) and a second constant domain ($C_L$).

Further, the present invention also provides an IgG bispecific antibody comprising: (a) a first heavy chain, wherein said first heavy chain comprises a first variable domain ($V_H$) and a first human IgG4 constant region, wherein said first human IgG4 constant region comprises an amino acid sequence as given by SEQ NO:60; (b) a first light chain, wherein said first light chain comprises a first variable domain ($V_L$) and a first constant domain ($C_L$); (c) a second heavy chain, wherein said second heavy chain comprises a second variable domain ($V_H$) and a second human IgG4 constant region, wherein said second human IgG4 constant region comprises an amino acid sequence as given by SEQ ID NO:65; and (d) a second light chain, wherein said second light chain comprises a second variable domain ($V_L$) and a second constant domain ($C_L$).

As another particular embodiment, the present invention provides an IgG bispecific antibody comprising: (a) a first heavy chain, wherein said first heavy chain comprises a first variable domain ($V_H$) and a first human IgG4 constant region, wherein said first human IgG4 constant region comprises an amino acid sequence as given by SEQ ID NO:61; (b) a first light chain, wherein said first light chain comprises a first variable domain (q) and a first constant domain ($C_L$); (c) a second heavy chain, wherein said second heavy chain comprises a second variable domain ($V_H$) and a second human IgG4 constant region, wherein said second human IgG4 constant region comprises an amino acid sequence as given by SEQ NO:65; and (d) a second light chain, wherein said second light chain comprises a second variable domain ($V_L$) and a second constant domain ($C_L$).

The present invention also provides an IgG bispecific antibody comprising: (a) a first heavy chain, wherein said first heavy chain comprises a first variable domain ($V_H$) and a first human IgG4 constant region, wherein said first human IgG4 constant region comprises an amino acid sequence as given by SEQ ID NO:62; (b) a first light chain, wherein said first light chain comprises a first variable domain ($V_L$) and a first constant domain ($C_L$); (c) a second heavy chain, wherein said second heavy chain comprises a second variable domain ($V_H$) and a second human IgG4 constant region, wherein said second human IgG4 constant region comprises an amino acid sequence as given by SEQ ID NO:66; and (d) a second light chain, wherein said second light chain comprises a second variable domain ($V_L$) and a second constant domain ($C_L$).

As another particular embodiment, the present invention provides an IgG bispecific antibody comprising: (a) a first heavy chain, wherein said first heavy chain comprises a first variable domain ($V_H$) and a first human IgG4 constant region, wherein said first human IgG4 constant region comprises an amino acid sequence as given by SEQ ID NO:63; (b) a first light chain, wherein said first light chain comprises a first variable domain ($V_L$) and a first constant domain ($C_L$); (c) a second heavy chain, wherein said second heavy chain comprises a second variable domain ($V_H$) and a second human IgG4 constant region, wherein said second human IgG4 constant region comprises an amino acid sequence as given by SEQ ID NO:67; and (d) a second light chain, wherein said second light chain comprises a second variable domain ($V_L$) and a second constant domain ($C_L$).

As another particular embodiment, the present invention provides an IgG bispecific antibody comprising: (a) a first heavy chain, wherein said first heavy chain comprises a first variable domain ($V_H$) and a first human IgG4 constant region, wherein said first human IgG4 constant region comprises an amino acid sequence as given by SEQ ID NO:64; (b) a first light chain, wherein said first light chain comprises a first variable domain ($V_L$) and a first constant domain ($C_L$); (c) a second heavy chain, wherein said second heavy chain comprises a second variable domain ($V_H$) and a second human IgG4 constant region, wherein said second human IgG4 constant region comprises an amino acid sequence as given by SEQ ID NO:67; and (d) a second light chain, wherein said second light chain comprises a second variable domain ($V_L$) and a second constant domain ($C_L$).

Yet another particular embodiment provides an IgG bispecific antibody comprising: (a) a first heavy chain, wherein said first heavy chain comprises a first variable domain ($V_H$) and a first human IgG4 constant region, wherein said first human IgG4 constant region comprises an amino acid sequence as given by SEQ ID NO:63; (b) a first light chain, wherein said first light chain comprises a first variable domain ($V_L$) and a first constant domain ($C_L$); (c) a second heavy chain, wherein said second heavy chain comprises a second variable domain ($V_H$) and a second human IgG4 constant region, wherein said second human IgG4 constant region comprises an amino acid sequence as given by SEQ ID NO:69; and (d) a second light chain, wherein said second light chain comprises a second variable domain ($V_L$) and a second constant domain ($C_L$).

The present invention also provides an IgG bispecific antibody comprising: (a) a first heavy chain, wherein said first heavy chain comprises a first variable domain ($V_H$) and a first human IgG4 constant region, wherein said first human IgG4 constant region comprises an amino acid sequence as given by SEQ ID NO:63; (b) a first light chain, wherein said first light chain comprises a first variable domain ($V_L$) and a first constant domain ($C_L$); (c) a second heavy chain, wherein said second heavy chain comprises a second variable domain ($V_H$) and a second human IgG4 constant region, wherein said second human IgG4 constant region comprises an amino acid sequence as given by SEQ ID NO:68; and (d) a second light chain, wherein said second light chain comprises a second variable domain ($V_L$) and a second constant domain ($C_L$).

Another embodiment provides an IgG bispecific antibody comprising: (a) a first heavy chain, wherein said first heavy chain comprises a first variable domain ($V_H$) and a first human IgG4 constant region, wherein said first human IgG4 constant region comprises an amino acid sequence as given by SEQ ID NO:64; (b) a first light chain, wherein said first light chain comprises a first variable domain ($V_L$) and a first constant domain ($C_L$); (c) a second heavy chain, wherein said second heavy chain comprises a second variable domain ($V_H$) and a second human IgG4 constant region, wherein said second human IgG4 constant region comprises an amino acid sequence as given by SEQ ID NO:68; and (d) a second light chain, wherein said second light chain comprises a second variable domain ($V_L$) and a second constant domain ($C_L$).

Further, the present invention also provides an IgG bispecific antibody comprising: (a) a first heavy chain, wherein said first heavy chain comprises a first variable domain ($V_H$) and a first human IgG4 constant region, wherein said first human IgG4 constant region comprises an amino acid sequence as given by SEQ NO:64; (b) a first light chain, wherein said first light chain comprises a first variable domain ($V_L$) and a first constant domain ($C_L$); (c) a second heavy chain, wherein said second heavy chain comprises a second variable domain ($V_H$) and a second human IgG4 constant region, wherein said second human IgG4 constant region comprises an amino acid sequence as given by SEQ ID NO:69; and (d) a second light chain, wherein said second light chain comprises a second variable domain and a second constant domain ($C_L$).

As an even more particular embodiment, the present invention combines $C_H3$ domain designs in the IgG1, IgG2 or IgG4 constant regions with Fab designs as described in Lewis et al. (2014) and WO2014/150973. In particular, the present invention provides an IgG bispecific antibody according to any one of the afore-mentioned IgG bispecific antibodies, wherein: (a) one of said first or second heavy chains further comprises a variable domain ($V_H$) comprising a lysine substituted at residue 39 (or a lysine at residue 39) and a glutamic acid substituted at the residue (or a glutamic acid at the residue) which is four amino acids upstream of the first residue of HFR3 according to Kabat Numbering system, and a human IgG1 or human IgG4 $C_H1$ domain comprising an alanine substituted at residue 172 (or an alanine at residue 172) and a glycine substituted at residue 174 (or a glycine at residue 174); (b) one of said first or second light chains comprises a kappa variable domain ($V_L$), comprising an arginine substituted at residue 1 (or an arginine at residue 1) and an aspartic acid substituted at residue 38 (or an aspartic acid at residue 38), and a constant domain ($C_L$) comprising a tyrosine substituted at residue 135 (or a tyrosine at residue 135) and a tryptophan substituted at residue 176 (or a tryptophan at residue 176); (c) the other of said first or second heavy chains further comprises a variable domain ($V_H$) comprising a tyrosine substituted at residue 39 (or a tyrosine at residue 39) and a WT human IgG1 or human IgG4 $C_H1$ domain; and (d) the other of said first or second light chains comprises a variable domain (VL) comprising an arginine substituted at residue 38 (or an arginine at residue 38) and a WT constant domain ($C_L$), wherein the $V_H$ domain comprising a lysine substituted at residue 39 (or a lysine at residue 39) and a glutamic acid substituted at the residue (or a glutamic acid at the residue) which is four amino acids upstream of the first residue of HFR3 according to Kabat and the human IgG1 or human IgG4 $C_H1$ domain comprising an alanine substituted at residue 172 (or an alanine at residue 172) and a glycine substituted at residue 174 (or a glycine at residue 174) together with the ($V_L$) comprising an arginine substituted at residue 1 (or an arginine at residue 1) and an aspartic acid substituted at residue 38 (or an aspartic acid at residue 38) and the $C_L$ domain comprising a tyrosine substituted at residue 135 (or a tyrosine at residue 135) and a tryptophan substituted at residue 176 (or a tryptophan at residue 176) form a first Fab which directs binding to a first target; and the $V_H$ domain comprising a tyrosine substituted at residue 39 (or a tyrosine at residue 39) and the WT human IgG1 or human IgG4 $C_H1$ domain together with the (q) comprising an arginine substituted at residue 38 (or an arginine at residue 38) and the WT $C_L$ domain form a second Fab which directs binding to a second target which is different from the first target.

Even more particular, the present invention combines the afore-mentioned $C_H3$ domain designs with Fab designs to provide an IgG bispecific antibody, wherein: (a) one of said first or second heavy chains further comprises a variable domain ($V_H$) comprising a lysine substituted at residue 39 (or a lysine at residue 39) and a glutamic acid substituted at the residue (or a glutamic acid at the residue) which is four amino acids upstream of the first residue of HFR3 according to Kabat Numbering system, and a human IgG1 or human IgG4 $C_H1$ domain comprising an alanine substituted at residue 172 (or an alanine at residue 172) and a glycine substituted at residue 174 (or a glycine at residue 174); (b) one of said first or second light chains comprises a kappa variable domain ($V_L$) comprising an arginine substituted at residue 1 (or an arginine at residue 1) and an aspartic acid substituted at residue 38 (or an aspartic acid at residue 38), and a constant domain ($C_L$), comprising a tyrosine substituted at residue 135 (or a tyrosine at residue 135) and a tryptophan substituted at residue 176 (or a tryptophan at residue 176); (c) the other of said first or second heavy chains further comprises a variable domain ($V_H$) comprising a tyrosine substituted at residue 39 (or a tyrosine at residue 39) and an arginine substituted at residue 105 (or an arginine at residue 105) and a human IgG1 or human IgG4 $C_H1$ domain comprising a cysteine substituted at residue 127 (or a cysteine at residue 127), an aspartic acid substituted at residue 228 (or an aspartic acid at residue 228), and a glycine substituted at residue 230 (or a glycine at residue 230); and (d) the other of said first or second light chains comprises a variable domain (VL) comprising an arginine substituted at residue 38 (or an arginine at residue 38) and an aspartic acid substituted at residue 42 (or an aspartic acid at residue 42), and a constant domain ($C_L$) comprising a lysine substituted at residue 122 (or a lysine at residue 122), wherein the $V_H$ domain comprising a lysine substituted at residue 39 (or a lysine at residue 39) and a glutamic acid substituted at the residue (or a glutamic acid at the residue) which is four amino acids upstream of the first residue of HFR3 according to Kabat and the human IgG1 or human IgG4 $C_H1$ domain comprising an alanine substituted at residue 172 (or an alanine at residue 172) and a glycine substituted at residue 174 (or a glycine at residue 174) together with the ($V_L$) comprising an arginine substituted at residue 1 (or an arginine at residue 1) and an aspartic acid substituted at residue 38 (or an aspartic acid at residue 38) and the $C_L$ domain comprising a tyrosine substituted at residue 135 (or a tyrosine at residue 135) and a tryptophan substituted at residue 176 (or a tryptophan at residue 176) form a first Fab which directs binding to a first target; and the $V_H$ domain comprising a tyrosine substituted at residue 39 (or a tyrosine at residue 39) and an arginine substituted at residue 105 (or an arginine at residue 105) and the human IgG1 or human IgG4 $C_H1$ domain comprising a cysteine substituted at residue 127 (or a cysteine at residue 127), an aspartic acid substituted at residue 228 (or an aspartic acid at residue 228), and a glycine substituted at residue 230 (or a glycine at residue 230) together with the ($V_L$) comprising an arginine substituted at residue 38 (or an arginine at residue 38) and an aspartic acid substituted at residue 42 (or an aspartic acid at residue 42) and the $C_L$ domain comprising a lysine substituted at residue 122 (or a lysine at residue 122) form a second Fab which directs binding to a second target which is different from the first target.

The present invention also provides processes for preparing the IgG bispecific antibodies of the present invention. In particular, the present invention provides a process for preparing an IgG bispecific antibody, comprising: (1) co-expressing in a host cell: (a) a first nucleic acid sequence encoding a first heavy chain, wherein said first heavy chain comprises a first variable domain ($V_H$) and a first human IgG1 or human IgG4 constant region, wherein said first human IgG1 or human IgG4 constant region comprises an alanine substituted at residue 407 (or an alanine at residue 407) of the $C_H3$ domain; (b) a second nucleic acid sequence encoding a first light chain, wherein said first light chain comprises a first variable domain ($V_L$) and a first constant domain ($C_L$); (c) a third nucleic acid sequence encoding a second heavy chain, wherein said second heavy chain comprises a second variable domain ($V_H$) and a second human IgG1 or human IgG4 constant region, wherein said second human IgG1 or human IgG4 constant region comprises a valine or methionine substituted at residue 366 (or a valine or methionine at residue 366) and a valine substituted at residue 409 (or a valine at residue 409) of the CH3 domain; and (d) a fourth nucleic acid sequence encoding a second light chain, wherein said second light chain comprises a second variable domain (VD and a second constant domain ($C_L$), wherein one of said first or second heavy chain variable domains and one of said first or second light chain variable domains each comprise three complementarity determining regions (CDRs) which direct binding to a first antigen, and the other of said first or second heavy chain variable domains and first or second light chain variable domains each comprise three complementarily determining regions (CDRs) which direct binding to a second antigen that differs from said first antigen; (2) cultivating said host cell under conditions such that said first and second heavy chains and said first and second light chains are produced; and (3) recovering from said host cell an IgG bispecific antibody comprising a first and second antigen binding fragment (Fab) wherein said first Fab comprises one of said first or second $V_H$ domains and one of said first or second $V_L$ domains, each of which comprise three CDRs which direct binding to a first antigen, and said second Fab comprises the other of said first or second $V_H$ domains and the other of said first or second $V_L$ domains, each of which comprise three CDRs which direct binding to a second antigen that differs from the first antigen.

In a particular embodiment to the process for preparing an IgG bispecific antibody of the present invention (a) the first nucleic acid sequence encodes a first heavy chain, wherein said first heavy chain comprises a first variable domain ($V_H$) and a first human IgG1 or human IgG4 constant region, wherein said first human IgG1 or human IgG4 constant region comprises an alanine substituted at residue 407 (or an alanine at residue 407) of the $C_H3$ domain; (b) the second nucleic acid encodes a first light chain, wherein said first light chain comprises a first variable domain ($V_L$) and a first constant domain ($C_L$); (c) the third nucleic acid encodes a second heavy chain, wherein said second heavy chain comprises a second variable domain ($V_H$) and a second human IgG1 or human IgG4 constant region, wherein said second human IgG1 or human IgG4 constant region comprises a valine substituted at residue 366 (or a valine at residue 366) and a valine substituted at residue 409 (or a valine at residue 409) of the $C_H3$ domain; and (d) the fourth nucleic acid sequence encodes a second light chain, wherein said second light chain comprises a second variable domain ($V_L$) and a second constant domain ($C_L$).

In another particular embodiment to the process for preparing an IgG bispecific antibody of the present invention (a) the first nucleic acid sequence encodes a first heavy chain, wherein said first heavy chain comprises a first variable domain ($V_H$) and a first human IgG1 or human IgG4 constant region, wherein said first human IgG1 or human IgG4 constant region comprises an alanine substituted at residue 407 (or an alanine at residue 407) and a methionine substituted at residue 399 (or a methionine at residue 399) of the $C_H3$ domain; (b) the second nucleic acid sequence encodes a first light chain, wherein said first light chain comprises a first variable domain ($V_L$) and a first constant domain ($C_L$); (c) the third nucleic acid sequence encodes a second heavy chain, wherein said second heavy chain comprises a second variable domain (KM and a second human IgG1 or human IgG4 constant region, wherein said second human IgG1 or human IgG4 constant region comprises a valine substituted at residue 366 (or a valine at residue 366) and a valine substituted at residue 409 (or a valine at residue 409) of the $C_H3$ domain; and (d) the fourth nucleic acid sequence encodes a second light chain, wherein said second light chain comprises a second variable domain ($V_L$) and a second constant domain ($C_L$).

In another particular embodiment to the process for preparing an IgG bispecific antibody of the present invention (a) the first nucleic acid sequence encodes a first heavy chain, wherein said first heavy chain comprises a first variable domain ($V_H$) and a first human IgG1 or human IgG4 constant region, wherein said first human IgG1 or human IgG4 constant region comprises an alanine substituted at residue 407 (or an alanine at residue 407), a methionine substituted at residue 399 (or a methionine at residue 399) and an aspartic acid substituted at residue 360 (or an aspartic acid at residue 360) of the $C_H3$ domain; (b) the second nucleic acid sequence encodes a first light chain, wherein said first light chain comprises a first variable domain ($V_L$) and a first constant domain ($C_L$); (c) the third nucleic acid sequence encodes a second heavy chain, wherein said second heavy chain comprises a second variable domain ($V_H$) and a second human IgG1 or human IgG4 constant region, wherein said second human IgG1 or human IgG4 constant region comprises a valine substituted at residue 366 (or a valine at residue 366), a valine substituted at residue 409 (or a value at residue 409), and an arginine substituted at residues 345 and 347 (or an arginine at residues 345 and 347) of the $C_H3$ domain; and (d) the fourth nucleic acid sequence encodes a second light chain, wherein said second light chain comprises a second variable domain ($V_L$) and a second constant domain ($C_L$).

In another particular embodiment to the process for preparing an IgG bispecific antibody of the present invention (a) the first nucleic acid sequence encodes a first heavy chain, wherein said first heavy chain comprises a first variable domain ($V_H$) and a first human IgG1 or human IgG4 constant region, wherein said first human IgG1 or human IgG4 constant region comprises an aspartic acid substituted at residue 357 (or an aspartic acid at residue 357), a glutamine substituted at residue 364 (or a glutamine at residue 364) and an alanine substituted at residue 407 (or an alanine at residue 407) of the $C_H3$ domain; (b) the second nucleic acid sequence encodes a first light chain, wherein said first light chain comprises a first variable domain ($V_L$) and a first constant domain ($C_L$); (c) the third nucleic acid sequence encodes a second heavy chain, wherein said second heavy chain comprises a second variable domain ($V_H$) and a second human IgG1 or human IgG4 constant region, wherein said second human IgG1 or human IgG4 constant region comprises a serine substituted at residue 349 (or a serine at residue 349), a valine substituted at residue 366 (or a valine at residue 366), a tyrosine substituted at residue 370 (or a tyrosine at residue 370) and a valine substituted at residue 409 (or a valine at residue 409) of the $C_H3$ domain; and (d) the fourth nucleic acid sequence encodes a second light chain, wherein said second light chain comprises a second variable domain ($V_L$) and a second constant domain ($C_L$).

In another particular embodiment to the process for preparing an IgG bispecific antibody of the present invention (a) the first nucleic acid sequences encodes a first heavy chain, wherein said first heavy chain comprises a first variable domain ($V_H$) and a first human IgG1 or human IgG4 constant region, wherein said first human IgG1 or human IgG4 constant region comprises an aspartic acid substituted at residue 357 (or an aspartic acid at residue 357), a glutamine substituted at residue 364 (or a glutamine at residue 364) and an alanine substituted at residue 407 (or an alanine at residue 407) of the $C_H3$ domain; (b) the second nucleic acid sequences encodes a first light chain, wherein said first light chain comprises a first variable domain ($V_L$) and a first constant domain ($C_L$); (c) the third nucleic acid sequences encodes a second heavy chain, wherein said second heavy chain comprises a second variable domain and a second human IgG1 or human IgG4 constant region, wherein said second human IgG1 or human IgG4 constant region comprises a serine substituted at residue 349 (or a serine at residue 349), a methionine substituted at residue 366 (or a methionine at residue 366), a tyrosine substituted at residue 370 (or a tyrosine at residue 370) and a valine substituted at residue 409 (or a valine at residue 409) of the $C_H3$ domain; and (d) the fourth nucleic acid sequences encodes a second light chain, wherein said second light chain comprises a second variable domain ($V_L$) and a second constant domain ($C_L$).

In another particular embodiment to the process for preparing an IgG bispecific antibody of the present invention (a) the first nucleic acid sequence encodes a first heavy chain, wherein said first heavy chain comprises a first variable domain ($V_H$) and a first human IgG1 or human IgG4 constant region, wherein said first human IgG1 or human IgG4 constant region comprises an aspartic acid substituted at residue 357 (or an aspartic acid at residue 357), an arginine substituted at residue 364 (or an arginine at residue 364) and an alanine substituted at residue 407 (or an alanine at residue 407) of the $C_H3$ domain; (h) the second nucleic acid sequence encodes a first light chain, wherein said first light chain comprises a first variable domain ($V_L$) and a first constant domain ($C_L$); (c) the third nucleic acid sequence encodes a second heavy chain, wherein said second heavy chain comprises a second variable domain ($V_H$) and a second human IgG1 or human IgG4 constant region, wherein said second human IgG1 or human IgG4 constant region comprises a serine substituted at residue 349 (or a serine at residue 349), a valine substituted at residue 366 (or a valine at residue 366), a tyrosine substituted at residue 370 (or a tyrosine at residue 370) and a valine substituted at residue 409 (or a valine at residue 409) of the $C_H3$ domain; and (d) the fourth nucleic acid sequence encodes a second light chain, wherein said second light chain comprises a second variable domain ($V_L$) and a second constant domain ($C_L$).

In yet another particular embodiment to the process for preparing an IgG bispecific antibody of the present invention (a) the first nucleic acid sequence encodes a first heavy chain, wherein said first heavy chain comprises a first variable domain ($V_H$) and a first human IgG1 or human IgG4 constant region, wherein said first human IgG1 or human IgG4 constant region comprises a glycine substituted at residue 356 (or a glycine at residue 356), an aspartic acid substituted at residue 357 (or an aspartic acid at residue 357), a glutamine substituted at residue 364 (or a glutamine at residue 364) and an alanine substituted at residue 407 (or an alanine at residue 407) of the $C_H3$ domain; (b) the second nucleic acid sequence encodes a first light chain, wherein said first light chain comprises a first variable domain ($V_L$) and a first constant domain ($C_L$); (c) the third nucleic acid sequence encodes a second heavy chain, wherein said second heavy chain comprises a second variable domain ($V_H$) and a second human IgG1 or human IgG4 constant region, wherein said second human IgG1 or human IgG4 constant region comprises a serine substituted at residue 349 (or a serine at residue 349), a valine substituted at residue 366 (or a valine at residue 366), a tyrosine substituted at residue 370 (or a tyrosine at residue 370) and a valine substituted at residue 409 (or a valine at residue 409) of the $C_H3$ domain; and (d) the fourth nucleic acid sequence encodes a second light chain, wherein said second light chain comprises a second variable domain ($V_L$) and a second constant domain ($C_L$).

In yet another particular embodiment to the process for preparing an IgG bispecific antibody of the present invention (a) the first nucleic acid sequence encodes a first heavy chain, wherein said first heavy chain comprises a first variable domain ($V_H$) and a first human IgG1 or human IgG4 constant region, wherein said first human IgG1 or human IgG4 constant region comprises a glycine substituted at residue 356 (or a glycine at residue 356), an aspartic acid substituted at residue 357 (or an aspartic acid at residue 357), a glutamine substituted at residue 364 (or a glutamine at residue 364) and an alanine substituted at residue 407 (or an alanine at residue 407) of the $C_H3$ domain; (b) the second nucleic acid sequence encodes a first light chain, wherein said first light chain comprises a first variable domain ($V_L$) and a first constant domain ($C_L$); (c) the third nucleic acid sequence encodes a second heavy chain, wherein said second heavy chain comprises a second variable domain ($V_H$) and a second human IgG1 or human IgG4 constant region, wherein said second human IgG1 or human IgG4 constant region comprises a serine substituted at residue 349 (or a serine at residue 349), a methionine substituted at residue 366 (or a methionine at residue 366), a tyrosine substituted at residue 370 (or a tyrosine at residue 370) and a valine substituted at residue 409 (or a valine at residue 409) of the $C_H3$ domain; and (d) the fourth nucleic acid sequence encodes a second light chain, wherein said second light chain comprises a second variable domain ($V_L$) and a second constant domain ($C_L$).

In yet another particular embodiment to the process for preparing an IgG bispecific antibody of the present invention (a) the first nucleic acid sequence encodes a first heavy chain, wherein said first heavy chain comprises a first variable domain ($V_H$) and a first human IgG1 or human IgG4 constant region, wherein said first human IgG1 or human IgG4 constant region comprises an aspartic acid substituted at residue 357 (or an aspartic acid at residue 357), an arginine substituted at residue 364 (or an arginine at residue 364) and an alanine substituted at residue 407 (or an alanine at residue 407) of the $C_H3$ domain; (b) the second nucleic acid sequence encodes a first light chain, wherein said first light chain comprises a first variable domain ($V_L$) and a first constant domain ($C_L$); (c) the third nucleic acid sequence encodes a second heavy chain, wherein said second heavy chain comprises a second variable domain ($V_H$) and a second human IgG1 or human IgG4 constant region, wherein said second human IgG1 or human IgG4 constant region comprises a serine substituted at residue 349 (or a serine at residue 349), a methionine substituted at residue 366 (or a methionine at residue 366), a tyrosine substituted at residue 370 (or a tyrosine at residue 370) and a valine substituted at residue 409 (or a valine at residue 409) of the $C_H3$ domain; and (d) the fourth nucleic acid sequence encodes a second light chain, wherein said second light chain comprises a second variable domain ($V_L$) and a second constant domain ($C_L$).

As particular embodiments to the processes of the present invention, processes for preparing IgG bispecific antibodies are provided, wherein the nucleic acids encoding the first and second heavy chains each encode human IgG1 constant regions comprising $C_H2$-$C_H3$ segments of a particular amino acid sequence. Thus, in a particular embodiment to the process for preparing an IgG bispecific antibody of the present invention (a) the first nucleic acid sequence encodes a first heavy chain, wherein said first heavy chain comprises a first variable domain ($V_H$) and a first human IgG1 constant region, wherein said first human IgG1 constant region comprises an amino acid sequence as given by SEQ ID NO:7; (b) the second nucleic acid encodes a first light chain, wherein said first light chain comprises a first variable domain ($V_L$) and a first constant domain ($C_L$); (c) the third nucleic acid encodes a second heavy chain, wherein said second heavy chain comprises a second variable domain ($V_H$) and a second human IgG1 constant region, wherein said second human IgG1 constant region comprises an amino acid sequence as given by SEQ ID NO:42; and (d) the fourth nucleic acid sequence encodes a second light chain, wherein said second light chain comprises a second variable domain ($V_L$) and a second constant domain ($C_L$).

In another particular embodiment to the process for preparing an IgG bispecific antibody of the present invention (a) the first nucleic acid sequence encodes a first heavy chain, wherein said first heavy chain comprises a first variable domain ($V_H$) and a first human IgG1 constant region, wherein said first human IgG1 constant region comprises an amino acid sequence as given by SEQ ID NO:38; (b) the second nucleic acid encodes a first light chain, wherein said first light chain comprises a first variable domain ($V_L$) and a first constant domain ($C_L$); (c) the third nucleic acid encodes a second heavy chain, wherein said second heavy chain comprises a second variable domain ($V_H$) and a second human IgG1 constant region, wherein said second human IgG1 constant region comprises an amino acid sequence as given by SEQ ID NO:42; and (d) the fourth nucleic acid sequence encodes a second light chain, wherein said second light chain comprises a second variable domain ($V_L$) and a second constant domain ($C_L$).

In another particular embodiment to the process for preparing an IgG bispecific antibody of the present invention (a) the first nucleic acid sequence encodes a first heavy chain, wherein said first heavy chain comprises a first variable domain ($V_H$) and a first human IgG1 constant region, wherein said first human IgG1 constant region comprises an amino acid sequence as given by SEQ ID NO:39; (b) the second nucleic acid encodes a first light chain, wherein said first light chain comprises a first variable domain ($V_L$) and a first constant domain ($C_L$); (c) the third nucleic acid encodes a second heavy chain, wherein said second heavy chain comprises a second variable domain ($V_H$) and a second human IgG1 constant region, wherein said second human IgG1 constant region comprises an amino acid sequence as given by SEQ ID NO:43; and (d) the fourth nucleic acid sequence encodes a second light chain, wherein said second light chain comprises a second variable domain ($V_L$) and a second constant domain ($C_L$).

In yet another particular embodiment to the process for preparing an IgG bispecific antibody of the present invention (a) the first nucleic acid sequence encodes a first heavy chain, wherein said first heavy chain comprises a first variable domain ($V_H$) and a first human IgG1 constant region, wherein said first human IgG1 constant region comprises an amino acid sequence as given by SEQ ID NO:40; (b) the second nucleic acid encodes a first light chain, wherein said first light chain comprises a first variable domain ($V_L$) and a first constant domain ($C_L$); (c) the third nucleic acid encodes a second heavy chain, wherein said second heavy chain comprises a second variable domain ($V_H$) and a second human IgG1 constant region, wherein said second human IgG1 constant region comprises an amino acid sequence as given by SEQ ID NO:44; and (d) the fourth nucleic acid sequence encodes a second light chain, wherein said second light chain comprises a second variable domain ($V_L$) and a second constant domain ($C_L$).

In yet another particular embodiment to the process for preparing an IgG bispecific antibody of the present invention (a) the first nucleic acid sequence encodes a first heavy chain, wherein said first heavy chain comprises a first variable domain ($V_H$) and a first human IgG1 constant region, wherein said first human IgG1 constant region comprises an amino acid sequence as given by SEQ NO:41; (b) the second nucleic acid encodes a first light chain, wherein said first light chain comprises a first variable domain ($V_L$) and a first constant domain ($C_L$); (c) the third nucleic acid encodes a second heavy chain, wherein said second heavy chain comprises a second variable domain ($V_H$) and a second human IgG1 constant region, wherein said second human IgG1 constant region comprises an amino acid sequence as given by SEQ ID NO:44; and (d) the fourth nucleic acid sequence encodes a second light chain, wherein said second light chain comprises a second variable domain ($V_L$) and a second constant domain ($C_L$).

In still another particular embodiment to the process for preparing an IgG bispecific antibody of the present invention (a) the first nucleic acid sequence encodes a first heavy chain, wherein said first heavy chain comprises a first variable domain ($V_H$) and a first human IgG1 constant region, wherein said first human IgG1 constant region comprises an amino acid sequence as given by SEQ ID NO:40; (b) the second nucleic acid encodes a first light chain, wherein said first light chain comprises a first variable domain ($V_L$) and a first constant domain ($C_L$); (c) the third nucleic acid encodes a second heavy chain, wherein said second heavy chain comprises a second variable domain ($V_H$) and a second human IgG1 constant region, wherein said second human IgG1 constant region comprises an amino acid sequence as given by SEQ ID NO:46; and (d) the fourth nucleic acid sequence encodes a second light chain, wherein said second light chain comprises a second variable domain ($V_L$) and a second constant domain ($C_L$).

In another particular embodiment to the process for preparing an IgG bispecific antibody of the present invention (a) the first nucleic acid sequence encodes a first heavy chain, wherein said first heavy chain comprises a first variable domain ($V_H$) and a first human IgG1 constant region, wherein said first human IgG1 constant region comprises an amino acid sequence as given by SEQ ID NO:40; (b) the second nucleic acid encodes a first light chain, wherein said first light chain comprises a first variable domain ($V_L$) and a first constant domain ($C_L$); (c) the third nucleic acid encodes a second heavy chain, wherein said second heavy chain comprises a second variable domain ($V_H$) and a second human IgG1 constant region, wherein said second human IgG1 constant region comprises an amino acid sequence as given by SEQ ID NO:45; and (d) the fourth nucleic acid sequence encodes a second light chain, wherein said second light chain comprises a second variable domain ($V_L$) and a second constant domain ($C_L$).

In yet another particular embodiment to the process for preparing an IgG bispecific antibody of the present invention (a) the first nucleic acid sequence encodes a first heavy chain, wherein said first heavy chain comprises a first variable domain ($V_H$) and a first human IgG1 constant region, wherein said first human IgG1 constant region comprises an amino acid sequence as given by SEQ ID NO:41; (b) the second nucleic acid encodes a first light chain, wherein said first light chain comprises a first variable domain ($V_L$) and a first constant domain ($C_L$); (c) the third nucleic acid encodes a second heavy chain, wherein said second heavy chain comprises a second variable domain ($V_H$) and a second human IgG1 constant region, wherein said second human IgG1 constant region comprises an amino acid sequence as given by SEQ ID NO:45; and (d) the fourth nucleic acid sequence encodes a second light chain, wherein said second light chain comprises a second variable domain ($V_L$) and a second constant domain ($C_L$).

In a further particular embodiment to the process for preparing an IgG-bispecific antibody of the present invention (a) the first nucleic acid sequence encodes a first heavy chain, wherein said first heavy chain comprises a first variable domain ($V_H$) and a first human IgG1 constant region, wherein said first human IgG1 constant region comprises an amino acid sequence as given by SEQ ID NO:41; (b) the second nucleic acid encodes a first light chain, wherein said first light chain comprises a first variable domain (q) and a first constant domain ($C_L$); (c) the third nucleic acid encodes a second heavy chain, wherein said second heavy chain comprises a second variable domain ($V_H$) and a second human IgG1 constant region, wherein said second human IgG1 constant comprises an amino acid sequence as given by SEQ ID NO:46; and (d) the fourth nucleic acid sequence encodes a second light chain, wherein said second light chain comprises a second variable domain ($V_L$) and a second constant domain ($C_L$).

In another particular embodiment to the process for preparing an IgG bispecific antibody of the present invention (a) the first nucleic acid sequence encodes a first heavy chain, wherein said first heavy chain comprises a first variable domain ($V_H$) and a first human IgG4 constant region, wherein said first human IgG4 constant region comprises an amino acid sequence as given by SEQ NO:60; (b) the second nucleic acid encodes a first light chain, wherein said first light chain comprises a first variable domain ($V_L$) and a first constant domain ($C_L$); (c) the third nucleic acid encodes a second heavy chain, wherein said second heavy chain comprises a second variable domain ($V_H$) and a second human IgG4 constant region, wherein said second human IgG4 constant region comprises an amino acid sequence as given by SEQ ID NO:65; and (d) the fourth nucleic acid sequence encodes a second light chain, wherein said second light chain comprises a second variable domain ($V_L$) and a second constant domain ($C_L$).

In another particular embodiment to the process for preparing an IgG bispecific antibody of the present invention (a) the first nucleic acid sequence encodes a first heavy chain, wherein said first heavy chain comprises a first variable domain ($V_H$) and a first human IgG4 constant region, wherein said first human IgG4 constant region comprises an amino acid sequence as given by SEQ ID NO:61; (b) the second nucleic acid encodes a first light chain, wherein said first light chain comprises a first variable domain ($V_L$) and a first constant domain ($C_L$); (c) the third nucleic acid encodes a second heavy chain, wherein said second heavy chain comprises a second variable domain ($V_H$) and a second human IgG4 constant region, wherein said second human IgG4 constant region comprises an amino acid sequence as given by SEQ ID NO:65; and (d) the fourth nucleic acid sequence encodes a second light chain, wherein said second light chain comprises a second variable domain ($V_L$) and a second constant domain ($C_L$).

In another particular embodiment to the process for preparing an IgG bispecific antibody of the present invention (a) the first nucleic acid sequence encodes a first heavy chain, wherein said first heavy chain comprises a first variable domain ($V_H$) and a first human IgG4 constant region, wherein said first human IgG4 constant region comprises an amino acid sequence as given by SEQ ID NO:62; (b) the second nucleic acid encodes a first light chain, wherein said first light chain comprises a first variable domain ($V_L$) and a first constant domain ($C_L$); (c) the third nucleic acid encodes a second heavy chain, wherein said second heavy chain comprises a second variable domain ($V_H$) and a second human IgG4 constant region, wherein said second human IgG4 constant region comprises an amino acid sequence as given by SEQ ID NO:66; and (d) the fourth nucleic acid sequence encodes a second light chain, wherein said second light chain comprises a second variable domain ($V_L$) and a second constant domain ($C_L$).

In yet another particular embodiment to the process for preparing an IgG bispecific antibody of the present invention (a) the first nucleic acid sequence encodes a first heavy chain, wherein said first heavy chain comprises a first variable domain ($V_H$) and a first human IgG4 constant region, wherein said first human IgG4 constant region comprises an amino acid sequence as given by SEQ ID NO:63; (b) the second nucleic acid encodes a first light chain, wherein said first light chain comprises a first variable domain (q) and a first constant domain ($C_L$); (c) the third nucleic acid encodes a second heavy chain, wherein said second heavy chain comprises a second variable domain ($V_H$) and a second human IgG4 constant region, wherein said second human IgG4 constant region comprises an amino acid sequence as given by SEQ ID NO:67; and (d) the fourth nucleic acid sequence encodes a second light chain, wherein said second light chain comprises a second variable domain ($V_L$) and a second constant domain ($C_L$).

In yet another particular embodiment to the process for preparing an IgG bispecific antibody of the present invention (a) the first nucleic acid sequence encodes a first heavy chain, wherein said first heavy chain comprises a first variable domain ($V_H$) and a first human IgG4 constant region, wherein said first human IgG4 constant region comprises an amino acid sequence as given by SEQ ID NO:64; (b) the second nucleic acid encodes a first light chain, wherein said first light chain comprises a first variable domain ($V_L$) and a first constant domain ($C_L$); (c) the third nucleic acid encodes a second heavy chain, wherein said second heavy chain comprises a second variable domain ($V_H$) and a second human IgG4 constant region, wherein said second human IgG4 constant region comprises an amino acid sequence as given by SEQ ID NO:67; and (d) the fourth nucleic acid sequence encodes a second light chain, wherein said second light chain comprises a second variable domain ($V_L$) and a second constant domain ($C_L$).

In still another particular embodiment to the process for preparing an IgG bispecific antibody of the present invention (a) the first nucleic acid sequence encodes a first heavy chain, wherein said first heavy chain comprises a first variable domain ($V_H$) and a first human IgG4 constant region, wherein said first human IgG4 constant region comprises an amino acid sequence as given by SEQ ID NO:63; (b) the second nucleic acid encodes a first light chain, wherein said first light chain comprises a first variable domain ($V_L$) and a first constant domain ($C_L$); (c) the third nucleic acid encodes a second heavy chain, wherein said second heavy chain comprises a second variable domain ($V_H$) and a second human IgG4 constant region, wherein said second human IgG4 constant region comprises an amino acid sequence as given by SEQ ID NO:69; and (d) the fourth nucleic acid sequence encodes a second light chain, wherein said second light chain comprises a second variable domain ($V_L$) and a second constant domain ($C_L$).

In another particular embodiment to the process for preparing an IgG bispecific antibody of the present invention (a) the first nucleic acid sequence encodes a first heavy chain, wherein said first heavy chain comprises a first variable domain ($V_H$) and a first human IgG4 constant region, wherein said first human IgG4 constant region comprises an amino acid sequence as given by SEQ ID NO:63; (b) the second nucleic acid encodes a first light chain, wherein said first light chain comprises a first variable domain ($V_L$) and a first constant domain ($C_L$); (c) the third nucleic acid encodes a second heavy chain, wherein said second heavy chain comprises a second variable domain ($V_H$) and a second human IgG4 constant region, wherein said second human IgG4 constant region comprises an amino acid sequence as given by SEQ ID NO:68; and (d) the fourth nucleic acid sequence encodes a second light chain, wherein said second light chain comprises a second variable domain ($V_L$) and a second constant domain ($C_L$).

In yet another particular embodiment to the process for preparing an IgG bispecific antibody of the present invention (a) the first nucleic acid sequence encodes a first heavy chain, wherein said first heavy chain comprises a first variable domain ($V_H$) and a first human IgG4 constant region, wherein said first human IgG4 constant region comprises an amino acid sequence as given by SEQ ID NO:64; (b) the second nucleic acid encodes a first light chain, wherein said first light chain comprises a first variable domain ($V_L$) and a first constant domain ($C_L$); (c) the third nucleic acid encodes a second heavy chain, wherein said second heavy chain comprises a second variable domain ($V_H$) and a second human IgG4 constant region, wherein said second human IgG4 constant region comprises an amino acid sequence as given by SEQ ID NO:68; and (d) the fourth nucleic acid sequence encodes a second light chain, wherein said second light chain comprises a second variable domain ($V_L$) and a second constant domain ($C_L$).

In a further particular embodiment to the process for preparing an IgG bispecific antibody of the present invention (a) the first nucleic acid sequence encodes a first heavy chain, wherein said first heavy chain comprises a first variable domain ($V_H$) and a first human IgG4 constant region, wherein said first human IgG4 constant region comprises an amino acid sequence as given by SEQ ID NO:64; (b) the second nucleic acid encodes a first light chain, wherein said first light chain comprises a first variable domain ($V_L$) and a first constant domain ($C_L$); (c) the third nucleic acid encodes a second heavy chain, wherein said second heavy chain comprises a second variable domain ($V_H$) and a second human IgG4 constant region, wherein said second human IgG4 constant region comprises an amino acid sequence as given by SEQ ID NO:69; and (d) the fourth nucleic acid sequence encodes a second light chain, wherein said second light chain comprises a second variable domain ($V_L$) and a second constant domain ($C_L$).

As an even more particular embodiment to the processes for preparing an IgG bispecific antibody of the present invention, the present invention further combines $C_H3$ domain designs in the IgG1, IgG2 or IgG4 constant regions with Fab designs as described in Lewis et al. (2014) (and WO2014/150973) in the process. In particular, the present invention provides a process for preparing an IgG bispecific antibody according to any one of the afore-mentioned processes, wherein: (a) one of said first or third nucleic acid sequences encodes a heavy chain further comprising a variable domain ($V_H$) comprising a lysine substituted at residue 39 (or a lysine at residue 39) and a glutamic acid substituted at the residue (or a glutamic acid at the residue) which is four amino acids upstream of the first residue of HFR3 according to Kabat Numbering system, and a human IgG1 or human IgG4 $C_H1$ domain comprising an alanine substituted at residue 172 (or an alanine at residue 172) and a glycine substituted at residue 174; (b) one of said second or fourth nucleic acid sequences encodes a light chain comprising a kappa variable domain ($V_L$) comprising an arginine substituted at residue 1 (or an arginine at residue 1)

and an aspartic acid substituted at residue 38 (or an aspartic acid at residue 38), and a constant domain ($C_L$) comprising a tyrosine substituted at residue 135 (or a tyrosine at residue 135) and a tryptophan substituted at residue 176 (or a tryptophan at residue 176); (c) the other of said first or third nucleic acid sequences encodes a heavy chain further comprising a variable domain ($V_H$) comprising a tyrosine substituted at residue 39 (or a tyrosine at residue 39) and a WT human IgG1 or human IgG4 $C_H1$ domain; and (d) the other of said second or fourth nucleic acid sequences encodes a light chain comprising a variable domain ($V_L$) comprising an arginine substituted at residue 38 (or an arginine at residue 38) and a WT constant domain ($C_L$), wherein the IgG bispecific antibody recovered comprises: a first Fab comprising (i) the variable domain ($V_H$) comprising a lysine substituted at residue 39 (or a lysine at residue 39) and a glutamic acid substituted at the residue (or a glutamic acid at the residue) which is four amino acids upstream of the first residue of HFR3 according to Kabat Numbering system, and the human IgG1 or human IgG4 $C_H1$ domain comprising an alanine substituted at residue 172 (or an alanine at residue 172) and a glycine substituted at residue 174 (or a glycine at residue 174), together with (ii) the light chain comprising a kappa variable domain ($V_L$) comprising an arginine substituted at residue 1 (or an arginine at residue 1) and an aspartic acid substituted at residue 38 (or an aspartic acid at residue 38), and a constant domain ($C_L$) comprising a tyrosine substituted at residue 135 (or a tyrosine at residue 135) and a tryptophan substituted at residue 176 (or a tryptophan at residue 176); and a second Fab comprising (i) the variable domain ($V_H$) comprising a tyrosine substituted at residue 39 (or a tyrosine at residue 39) and a WT human IgG1 or human IgG4 $C_H1$ domain, together with (ii) the variable domain ($V_L$) comprising an arginine substituted at residue 38 (or an arginine at residue 38) and a WT constant domain ($C_L$).

Even more particular to the processes for preparing an IgG bispecific antibody of the present invention, the present invention combines the afore-mentioned $C_H3$ domain designs with additional Fab designs in the process. Thus, the present invention provides a process for preparing an IgG bispecific antibody according to any one of the afore-mentioned processes, wherein: (a) one of said first or third nucleic acid sequences encodes a heavy chain further comprising a variable domain ($V_H$) comprising a lysine substituted at residue 39 (or a lysine at residue 39) and a glutamic acid substituted at the residue (or a glutamic acid at the residue) which is four amino acids upstream of the first residue of HFR3 according to Kabat Numbering system, and a human IgG1 or human IgG4 $C_H1$ domain comprising an alanine substituted at residue 172 (or an alanine at residue 172) and a glycine substituted at residue 174 (or a glycine at residue 174); (b) one of said second or fourth nucleic acid sequences encodes a light chain comprising a kappa variable domain ($V_L$) comprising an arginine substituted at residue 1 (or an arginine at residue 1) and an aspartic acid substituted at residue 38 (or an aspartica acid at residue 38), and a constant domain ($C_L$) comprising a tyrosine substituted at residue 135 (or a tyrosine at residue 135) and a tryptophan substituted at residue 176 (or a tryptophan at residue 176); (c) the other of said first or third nucleic acid sequences encodes a heavy chain further comprising a variable domain ($V_H$) comprising a tyrosine substituted at residue 39 (or tyrosine at residue 39) and an arginine substituted at residue 105 (or an arginine at residue 105) and a human IgG1 or human IgG4 $C_H1$ domain comprising a cysteine substituted at residue 127 (or a cysteine at residue 127), an aspartic acid substituted at residue 228 (or an aspartic acid at residue 228), and a glycine substituted at residue 230 (or a glycine at residue 230); and (d) the other of second or fourth nucleic acid sequences encodes a light chain comprising a variable domain (VL) comprising an arginine substituted at residue 38 (or an arginine at residue 38) and an aspartic acid substituted at residue 42 (or an aspartic acid at residue 42), and a constant domain ($C_L$) comprising a lysine substituted at residue 122 (or a lysine at residue 122), wherein the IgG bispecific antibody recovered comprises: a first Fab comprising (i) the variable domain ($V_H$) comprising a lysine substituted at residue 39 (or a lysine at residue 39) and a glutamic acid substituted at the residue (or a glutamic acid at the residue) which is four amino acids upstream of the first residue of HFR3 according to Kabat Numbering system, and the human IgG1 or human IgG4 $C_H1$ domain comprising an alanine substituted at residue 172 (or an alanine at residue 172) and a glycine substituted at residue 174 (or a glycine at residue 174), together with (ii) the light chain comprising a kappa variable domain ($V_L$) comprising an arginine substituted at residue 1 (or an arginine at residue 1) and an aspartic acid substituted at residue 38 (or an aspartic acid at residue 38), and a constant domain ($C_L$) comprising a tyrosine substituted at residue 135 (or a tyrosine at residue 135) and a tryptophan substituted at residue 176 (or a tryptophan at residue 176); and a second Fab comprising (i) the variable domain ($V_H$) comprising a tyrosine substituted at residue 39 (or a tyrosine at residue 39) and an arginine substituted at residue 105 (or an arginine at residue 105) and a human IgG1 or human IgG4 $C_H1$ domain comprising a cysteine substituted at residue 127 (or a cysteine at residue 127), an aspartic acid substituted at residue 228 (or an aspartic acid at residue and a glycine substituted at residue 230 (or a glycine at residue 230), together with (ii) the variable domain ($V_L$) comprising an arginine substituted at residue 38 (or an arginine at residue 38) and an aspartic acid substituted at residue 42 (or an aspartic acid at residue 42), and a constant domain ($C_L$) comprising a lysine substituted at residue 122 (or a lysine at residue 122).

The present invention further provides an IgG bispecific antibody produced accord to any one of the processes of the present invention.

In addition to the preparation of Fully IgG BsAbs, the methods described herein may also be employed in the preparation of other multi- or mono-valent antigen binding compounds. FIG. 1, included herein, provides a schematic diagram of a Fully IgG BsAb, as well as other antigen binding compounds that one of skill in the art could prepare using the $C_H3$ domain designs, or the $C_H3$ domain designs plus Fab designs, as described herein.

The present invention further provides nucleic acid sequences encoding the first and second heavy chains and the first and second light chains of any of the IgG BsAbs of the present invention. In addition, the present invention also provides vectors comprising nucleic acid sequences encoding the first heavy chain, the first light chain, the second heavy chain and/or the second light chain of any of the IgG BsAbs of the present invention. Further still, the present invention provides host cells comprising nucleic acid sequences encoding the first heavy chain, the first light chain, the second heavy chain and the second light chain of any of the IgG BsAbs of the present invention.

BRIEF DESCRIPTION OF FIGURES

FIG. 1A-1F provides a schematic diagram of antigen binding compounds that may be prepared using the CH3 domain designs, methods or procedures of the present invention, including Fully IgG BsAbs (A), One-arm antibodies (B), a Tandem Fab-Fc molecules (C), IgG-scFv-Fc molecules (D), and IgG-scFv molecules (E and F). Detailed Legend:

FIG. 1A. Fully IgG BsAb comprising two Fabs (1 and 2) to separate targets and an Fc.

FIG. 1B. One-arm antibody comprising one Fab and one Fc.

FIG. 1C. Tandem Fab-Fc comprising two Fabs (1 and 2) to separate targets linked head-to-tail, and one Fc.

FIG. 1D. IgG-scFv-Fc comprising one Fab (to a first target) and an scFv (to a second target) and one Fc.

FIG. 1E. IgG-scFv comprising two Fabs (1 and 2) to separate targets, a scFv to a third target, and an Fc.

FIG. 1F. IgG-scFv comprising two Fabs (1 and 2) to separate targets, two scFvs (1 and 2) to separate targets, and an Fc.

"Fc(A)" and "Fc(B)" represent distinct CH2-CH3 segments containing CH3 designs and which form the Fc heterodimer.

The general structure of an "IgG antibody" is very well-known. A wild type (WT) antibody of the IgG type is hetero-tetramer of four polypeptide chains (two identical "heavy" chains and two identical "light" chains) that are cross-linked via intra- and inter-chain disulfide bonds. Each heavy chain (HC) is comprised of an N-terminal heavy chain variable region ("$V_H$") and a heavy chain constant region. The heavy chain constant region is comprised of three domains ($C_H1$, $C_H2$, and $C_H3$) as well as a hinge region ("hinge") between the $C_H1$ and $C_H2$ domains. Each light chain (LC) is comprised of an N-terminal light chain variable region ("$V_L$") and a light chain constant region ("$C_L$"). The $V_L$ and $C_L$ regions may be of the kappa ("κ") or lambda ("λ") isotypes. Each heavy chain associates with one light chain via an interface between the heavy chain $V_H$-$C_H1$ segment and the light chain $V_L$-$C_L$ segment. The association of each $V_H$-$C_H1$/$V_L$-$C_L$ forms two identical antigen binding fragments (Fabs) which direct antibody binding to the same target or epitope. Each heavy chain associates with the other heavy chain via an interface between the hinge-$C_H2$-$C_H3$ segments of each heavy chain, with the association between the $C_H2$-$C_H3$ segments forming the Fc region of the antibody. Together, each Fab and the Fc form the characteristic "Y-shaped" architecture of IgG antibodies, with each Fab representing the "arms" of the "Y." IgG antibodies can be further divided into subtypes, e.g., IgG1, IgG2, IgG3, and IgG4 which differ by the length of the hinge regions, the number and location of inter- and intra-chain disulfide bonds and the amino acid sequences of the respective HC constant regions.

The variable regions of each heavy chain-light chain pair associate to form binding sites. The heavy chain variable region ($V_H$) and the light chain variable region ($V_L$) can be subdivided into regions of hypervariability, termed complementarity determining regions ("CDRs"), interspersed with regions that are more conserved, termed framework regions ("FR"). Each $V_H$ and $V_L$ is composed of three CDRs and four FRs, arranged from amino-terminus to carboxy-terminus in the following order: FR1, CDR1, FR2, CDR2, FR3, CDR3, FR4. CDRs of the heavy chain may be referred to as "CDRH1, CDRH2, and CDRH3" and the 3 CDRs of the light chain may be referred to as "CDRL1, CDRL2 and CDRL3." The FRs of the heavy chain may be referred to as HFR1, HFR2, HFR3 and HFR4 whereas the FRs of the light chain may be referred to as LFR1, LFR2, LFR3 and LFR4. The CDRs contain most of the residues which form specific interactions with the antigen.

As used herein, the terms "IgG bispecific antibody", "IgG BsAb", "fully IgG bispecific antibody" or "fully IgG BsAb" refer to an antibody of the typical IgG architecture comprising two distinct Fabs, each of which direct binding to a separate antigen (e.g., different target proteins or different epitopes on the same target protein), and composed of two distinct IgG heavy chains and two distinct light chains. The $V_H$-$C_H1$ segment of one heavy chain associates with the $V_L$-$C_L$ segment of one light chain to form a "first" Fab, wherein the $V_H$ and $V_L$ domains each comprise 3 CDRs which direct binding to a first antigen. The $V_H$-$C_H1$ segment of the other heavy chain associates with the $V_L$-$C_L$ segment of the other light chain to term a "second" Fab, wherein the $V_H$ and $V_L$ domains each comprise 3 CDRs which direct binding to a second antigen that is different than the first. More particularly, the terms "IgG bispecific antibody", "IgG BsAb", "fully IgG bispecific antibody" or "fully IgG BsAb" refer to antibodies wherein the HC constant regions are composed of $C_H1$, $C_H2$, and $C_H3$ domains of the IgG1, IgG2 or IgG4 subtype, and particularly the human IgG1, human IgG2 or human IgG4. Even more particular, the terms refer to antibodies wherein the HC constant regions are composed of $C_H1$, $C_H2$, and $C_H3$ domains of the IgG1 or IgG4 subtype, and most particularly the human IgG1 or human IgG4 subtype. In addition, as used herein, the terms "IgG bispecific antibody", "IgG BsAb", "fully IgG bispecific antibody" and "fully IgG BsAb" refer to an antibody wherein the constant regions of each HC of the antibody are of the same subtype (for example, each HC of the antibody has $C_H1$, $C_H2$, and $C_H3$ domains of the human IgG1 subtype, or each HC of the antibody has $C_H1$, $C_H2$, and $C_H3$ domains of the human IgG2 subtype, or each HC of the antibody has $C_H1$, $C_H2$, and $C_H3$ domains of the human IgG4 subtype.)

The processes and compounds of the present invention comprise designed amino acid modifications at particular residues within the constant and variable regions of heavy chain and light chain polypeptides. As one of ordinary skill in the art will appreciate, various numbering conventions may be employed for designating particular amino acid residues within IgG constant and variable region sequences. Commonly used numbering conventions include the "Kabat Numbering" and "EU Index Numbering" systems. "Kabat Numbering" or "Kabat Numbering system", as used herein, refers to the numbering system devised and set forth by the authors in Kabat et al., *Sequences of Proteins of Immunological Interest*, 5th Ed, Public Health Service, National institutes of Health, Bethesda, Md. (1991) for designating amino acid residues in both variable and constant domains of antibody heavy chains and light chains. "EU Index Numbering" or "EU Index Numbering system", as used herein, refers to the numbering convention for designating amino acid residues in antibody heavy chain constant domains, and is also set forth in Kabat et al. (1991). Other conventions that include corrections or alternate numbering systems for variable domains include Chothia (Chothia C, Lesk A M (1987), *J Mol Biol* 196: 901-917; Chothia, et al. (1989), *Nature* 342; 877-883), IMGT (Lefranc, et al. (2003), *Dev Comp Immunol* 27: 55-77), and AHo (Honegger A, Pluckthun A (2001) *J Mol Biol* 309: 657-670). These references provide amino acid sequence numbering schemes for immunoglobulin variable regions that define the location of variable region amino acid residues of antibody sequences. Unless otherwise expressly stated herein, all references to immunoglobulin heavy chain variable region (i.e., $V_H$), constant region $C_H1$ and hinge amino acid residues (i.e. numbers) appearing in the Examples and Claims are based on the Kabat Numbering system, as are all references to the light chain $V_L$ and $C_L$ residues. All references to immunoglobulin heavy chain constant regions $C_H2$ and $C_H3$ are based on the EU Index Numbering system. With knowledge of the residue number according to Kabat Numbering or EU Index Numbering, one of ordinary skill can apply the teachings of the art to identify amino acid sequence modifications within the present invention, according to any commonly used numbering convention. Note, while the Examples and Claims of the present invention employ Kabat Numbering or EU Index Numbering to identify particular amino acid residues, it is understood that the SEQ ID NOs appearing in the Sequence Listing accompanying the present application, as generated by Patent In Version 3.5, provide sequential numbering of amino acids within a given polypeptide and, thus, do not conform to the corresponding amino acid residue numbers as provided by Kabat Numbering or EU Index Numbering.

However, as one of skill in the art will also appreciate, CDR sequence length may vary between individual IgG molecules and, further, the numbering of individual residues within a CDR may vary depending on the numbering convention applied. Thus, to reduce ambiguity in the designation of amino acid residues within CDRs, the disclosure of the present invention first employs Kabat Numbering to identify the N-terminal (first) amino acid of the HFR3. The amino acid residue to be modified is then designated as being four (4) amino acid residues upstream (i.e. in the N-terminal direction) from the first amino acid in the reference HFR3. For example, a Fab design used in combination with the $C_H3$ domain designs of the present invention comprises the replacement of a WT amino acid in HCDR2 with a glutamic acid (E) (i.e., Fab Design AB2133(a) comprising R62E mutation). This replacement is made at the residue located four amino acids upstream of the first amino acid of HFR3, according to Kabat Numbering. In the Kabat Numbering system, amino acid residue X66 is the most N-terminal (first) amino acid residue of variable region heavy chain framework three (HFR3). One of ordinary skill can employ such a strategy to identify the first amino acid residue (most N-terminal) of heavy chain framework three (HFR3) from any human IgG1 or IgG4 variable region. Once this landmark is identified, one can then locate the amino acid four residues upstream (N-terminal) to this location and replace that amino acid residue (using standard insertion/deletion methods) with a glutamic acid (E) to achieve the design modification of the invention. Given any variable IgG1 or IgG4 immunoglobulin heavy chain amino acid query sequence of interest to use in the processes of the invention, one of ordinary skill in the art of antibody engineering would be able to locate the N-terminal HFR3 residue in said query sequence and then count four amino acid residues upstream therefrom to arrive at the location in HCDR2 that should be modified to glutamic acid (E).

As used herein, the phrase " . . . a/an [amino acid name] substituted at residue . . . ", in reference to a heavy chain or light chain polypeptide, refers to substitution of the parental amino acid with the indicated amino acid. For example, a heavy chain comprising "a lysine substituted at residue 39" refers to a heavy chain wherein the parental amino acid sequence has been mutated to contain a lysine at residue number 39 in place of the parental amino acid. Such mutations may also be represented by denoting a particular amino acid residue number, preceded by the parental amino acid and followed by the replacement amino acid. For example, "Q39K" refers to a replacement of a glutamine at residue 39 with a lysine. Similarly, "39K" refers to replacement of a parental amino acid with a lysine. One of skill in the art will appreciate, however, that as a result of the HC-HC interface design modifications of the present invention, fully IgG BsAbs (and processes for their preparation) are provided wherein the component HC amino acid sequences, or component HC and LC amino acid sequences, comprise the resulting or "replacement" amino acid at the designated residue. Thus, tier example, a heavy chain which "comprises a lysine substituted at residue 39" may alternatively be denoted as a heavy chain "comprising a lysine at residue 39."

An IgG BsAb of the present invention may be derived from a single copy or clone (e.g. a monoclonal IgG BsAb antibody.) Preferably, an IgG BsAb of the present invention exists in a homogeneous or substantially homogeneous population. In an embodiment, the IgG BsAb, or a nucleic acid encoding a component polypeptide sequence of the IgG BsAb, is provided in "isolated" form. As used herein, the term "isolated" refers to a protein, polypeptide or nucleic acid which is free or substantially free from other macromolecular species found in a cellular environment.

An IgG BsAb of the present invention can be produced using techniques well known in the art, such as recombinant expression in mammalian or yeast cells. In particular, the methods and procedures of the Examples herein may be readily employed. In addition, the IgG BsAbs of the present invention may be further engineered to comprise framework regions derived from fully human frameworks. A variety of different human framework sequences may be used in carrying out embodiments of the present invention. Preferably, the framework regions employed in the processes of the present invention, as well as IgG BsAbs of the present invention are of human origin or are substantially human (at least 95%, 97% or 99% of human origin.) The sequences of framework regions of human origin are known in the art and may be obtained from *The Immunoglobulin Factsbook*, by Marie-Paule Lefranc, Gerard Lefranc, Academic Press 2001, ISBN 012441351.

Expression vectors capable of directing expression of genes to which they are operably linked are well known in the art. Expression vectors contain appropriate control sequences such as promoter sequences and replication initiation sites. They may also encode suitable selection markers as well as signal peptides that facilitate secretion of the desired polypeptide product(s) from a host cell. The signal peptide can be an immunoglobulin signal peptide or a heterologous signal peptide. Nucleic acids encoding desired polypeptides, for example the components of the IgG BsAbs prepared according to the processes of the present invention, may be expressed independently using different promoters to which they are operably linked in a single vector or, alternatively, the nucleic acids encoding the desired products may be expressed independently using different promoters to which they are operably linked in separate vectors. In addition, nucleic acids encoding a particular HC/LC pair of the IgG BsAbs of the present invention may expressed from a first vector, while the other HC/LC pair is expressed from a second vector. Single expression vectors encoding both HC and both LC components of the IgG BsAbs of the present invention may be prepared using standard methods. For example, a pE vector encoding a particular HC/LC pair may be engineered to contain a NaeI site 5 prime of a unique SalI site, outside of the HC/LC expression cassette. The vector may then be modified to contain an AscI site 5 prime of the SalI site using standard techniques. For example, the NaeI to SalI region may be PCR amplified using a 3' primer containing the AscI site adjacent to the SalI site, and the resulting fragment cloned into the recipient pE vector. The expression cassette encoding a second HC/LC pair, may then be isolated from a second (donor) vector by digesting the vector at suitable restriction sites. For example, the donor vector may be engineered with MluI and SalI sites to permit isolation of the second expression cassette. This cassette may then be ligated into the recipient vector previously digested at the AscI and SalI sites (as AscI and MluI restriction sites have the same overlapping ends.)

As used herein, a "host cell" refers to a cell that is stably or transiently transfected, transformed, transduced or infected with nucleotide sequences encoding a desired polypeptide product or products. Creation and isolation of host cell lines producing an IgG BsAb of the present invention can be accomplished using standard techniques known in the art.

Mammalian cells are preferred host cells for expression of the IgG BsAb compounds according to the present invention. Particular mammalian cells include HEK293, NS0, DG-44, and CHO cells. Preferably, assembled proteins are secreted into the medium in which the host cells are cultured, from which the proteins can be recovered and isolated. Medium into which a protein has been secreted may be purified by conventional techniques. For example, the medium may be applied to and eluted from a Protein A or G column using conventional methods. Soluble aggregate and multimers may be effectively removed by common techniques, including size exclusion, hydrophobic interaction, ion exchange, hydroxyapatite or mixed modal chromatography. Recovered products may be immediately frozen, for example at −70° C., or may be lyophilized. As one of skill in the art will appreciate, when expressed in certain biological systems, e.g. mammalian cell lines, antibodies are glycosylated in the Fc region unless mutations are introduced in the Fc to reduce glycosylation. In addition, antibodies may be glycosylated at other positions as well.

The following Examples further illustrate the invention and provide typical methods and procedures for carrying out various particular embodiments of the present invention. However, it is understood that the Examples are set forth the by way of illustration and not limitation, and that various modifications may be made by one of ordinary skill in the art.

Example 1

Computational and Rational Design of CH3/CH3 Interface Modifications

Residues for initial modification at the symmetric $C_H3$/$C_H3$ dimer interface (i.e., Chain A $C_H3$ domain and Chain B $C_H3$ domain) were selected using a combination of computational and rational design strategies. First, using a crystal structure of the human IgG1 $C_H2$-$C_H3$ domains (PDB 1L6X), trimmed of carbohydrate moieties that connect the $C_H2$ domains, the Rosetta software suite and related modeling applications were employed to computationally identify potential modifications that favor heterodimer (i.e., Chain A/Chain B) formation over homodimer (i.e., Chain A/Chain A or Chain B/ChainB) formation. (See, Kaufmann et al. (2010), *Biochemistry* 49; 2987-2998; Leaver-Fay et al. (2011), *Methods Enzymol.* 487; 545-574; Kuhlman et al. (2003), *Science* 302(5649); 1364-1368; and Leaver-Fay et al. (2011), *PLos ONE* 6(7): e20937; Lewis et al. (2014) *Nature Biotech.*, 32(2)). More than sixty discrete initial designs, falling into varying design paradigms, different amino acid substitutions and/or different amino acid residue positions) were identified, synthesized and tested for heterodimer formation and thermostability (as measured by UPLC, FRET and DSC, as described below.) Select Chain A/Chain B mutation pairs were further optimized rationally and/or assessed for compatibility for combination, including inverted combinations where mutations in one chain of a discrete design pair (e.g. Chain B) are added to the mutations in the opposite chain (e.g. Chain A) of a separate discrete design pair. Optimized and/or combination designs were then assessed computationally and those exhibiting promising heterodimer formation potential, and destabilized homodimer potential, were also synthesized and tested for heterodimer formation (as measured by UPLC and FRET) and thermostability (as measured by DSC.)

A. Computational Modeling

Briefly, Rosetta's multistate design module explores sequence space and for each sequence calculates an energy for each of several "states" based on a weighted sum of energy potentials treating phenomena such as van der Waals forces and hydrogen bonding forces, and then aggregates these energies to compute a fitness for that sequence. The states represent different combinations and conformations of protein chain species, e.g. different conformations of the Chain A/Chain B heterodimer, or different conformations of the Chain A/Chain A or Chain B/Chain B homodimer. The summations of the energy potentials are measured in units known as the Rosetta Energy Unit (REU). These values are interpreted as free energies, but do not directly translate into typical units of energy. Binding energies are computed as the difference between the energy of the bound complex and the energies of its separated components. Using a fitness function which favors the binding and stability of Chain A $C_H3$/Chain B $C_H3$ heterodimers and disfavors the binding of $C_H3$/$C_H3$ homodimers (Chain A/Chain A or Chain B/Chain B), initial sequences for modification are identified.

The identified mutations are subjected to computational docking of the heterodimer and homodimer complexes using RosettaDock via RosettaScripts (see, Chaudhury et al. (2011), *PLoS ONE* 6(8): DOI: 10.1371journal-.pone.0022477 and Fleishman et al. (2011), *PLoS ONE* 6(6): DOI: 10.1371/journal.pone.0020161). This docking step allows the complexes to relax into more favorable conformations for their sequences and facilitates the comparison of binding energies for the homodimer and heterodimer complexes. Energies are calculated using a variation on Rosetta's standard score function, "Talaris2013" (O'Meara et al. (2015) *J. Chem. Theory Comput.* 11(2); 609-622), where the atomic-interaction distance was extended to 9 Å and the amino-acid specific reference energies had been refit using Rosetta's automated refitting procedure, OptE (Leaver-Fay et al. (2013) *Methods Enzymol.* 523; 109-143). Following docking, binding energies are calculated as the difference in energies between the complex and the sidechain-optimized, separated conformations as reported by Rosetta's InterfaceAnalyzer tool (see, Lewis, S. M. and Kuhlman, B. A. (2011), *PLoS One* 6(6): DOI: 10.1371/journal-.pone.0020872). The conformations resulting from the docking simulations of homodimers which display favorable binding energies are used as additional states in subsequent multistate design simulations to further guide the those simulations away from sequences which favor homodimer formation. The multistate-design-followed-by-redocking process is iterated until the binding energies calculated by multistate design match well with binding energies calculated following docking.

Select designs, including further optimized and/or combination designs, resulting from this iterative process and their calculated binding energies are provided in Table 1.

TABLE 1

Rosetta multi-state computational design results.

| Design Construct | Chain A HC C$_H$3 Domain Mutations[a] | Chain B HC C$_H$3 Domain Mutations[a] | A/B[e] binding energy | A/A[e] binding energy | B/B[e] binding energy |
|---|---|---|---|---|---|
| WT[b] | None | — | — | −12 | — |
| 7.4 | Y407A | T366V K409V | −16.3 | −12.5 | −11.2 |
| 7.8 | Y407A D399M | T366V K409V | −17.2 | −11.3 | −5.3 |
| 7.8.60[b] | K360D D399M Y407A | E345R Q347R T366V K409V | −51.5 | −42.7 | −45.0 |
| 11.2a[c] | Y349A K370Y | E357D S364Q | −18.1 | −19.6 | −2.2 |
| 20.8[d] | Y349S T366V K370Y K409V | E357D S364Q Y407A | −29.7 | −13.4 | −14.9 |

[a]Mutations are designated by first identifying the one letter abbreviation for the parental amino acid, the amino acid residue number and the one letter abbreviation for the replacement amino acid. For example, Y407A indicates that residue 407 is modified from a tyrosine (Y) to an alanine (A). Binding energies were calculated following a fixed-backbone, rigid-body docking protocol, starting from the PDB ID 1L6X crystal structure.
[b]Binding energies calculated after flexible-backbone relaxation protocol. The addition of backbone flexibility lowers apparent binding energies considerably.
[c]In the constructs prepared in Section B below, 349A is modified to 349S in HC A as the Y349S mutation was observed in the calculations to make an additional hydrogen bond to 357D in HC B. This modification to Design 11.2a is denoted as Design 11.2.
[d]Binding energies were calculated following a fixed-backbone, rigid-body docking protocol, starting from a crystal structure of design 11.2.
[e]The designations "A/B", "A/A" and "B/B" refer to the CH3 domain hetero- or homodimer chain pairs B. Design Construct Heterodimer Formation and Thermostability Assessment of Heterodimer Formation by Ultra-Performance Liquid Chromatography (UPLC) Analytical Sizing To assess the heterodimer formation potential of Chain A C$_H$3 domain/Chain B C$_H$3 domain design pairs, "one-arm" antibody constructs incorporating design modifications in the C$_H$3/C$_H$3 dimer interface are prepared and tested. Unless otherwise indicated, "Chain A" of each construct contains a full heavy chain sequence (with or without C$_H$3 domain design modifications) and "Chain B" of each construct contains an Fc only portion (C$_H$2-C$_H$3 segment plus HA tag) of the heavy chain (with or without CH3 domain design modifications.)

Molecular Biology: Variable heavy domain (V$_H$) and variable light domain (V$_L$) sequences of the anti-cMet clone 5D5 (see U.S. Pat. No. 7,892,550) are synthesized. The V$_H$ domain-encoding sequence is cloned into a plasmid (pcDNA3.1(+) (Life Technologies)) containing sequences encoding a mouse kappa chain leader sequence and a complete human IgG1 heavy chain using HindIII/EcoR1 restriction sites. The V$_L$ domain-encoding sequence is cloned into a pEHK mammalian expression vector (Lonza) containing a sequence encoding a mouse kappa chain leader sequence and a 3' kappa constant domain, using the BamHI and EcoRI restriction sites. An HA-tagged Fc construct, to provide the other member of the C$_H$3 dimer interface, is constructed by first PCR amplifying a human IgG1 Fc from a full heavy chain using a forward primer which introduced an HA tag plus a four residue linker at the N-terminus of the chain. The HA-tagged Fc-encoding construct is then cloned into a pcDNA3.1(+) plasmid containing a sequence encoding a mouse kappa chain leader sequence using the BamH1 and EcoR1 restriction sites. Nucleic acid sequence modifications encoding the C$_H$3 domain design pair mutations are introduced using methods known in the art such as Kunkel mutagenesis (See Kunkel (1985) Proc Natl Acad Sci; 82(2): 488-492), QUIKCHANGE® site-directed mutagenesis (Agilent), or direct GBLOCK® gene cloning (Integrated DNA Technologies®, IDT) using restriction site cloning using EcoRI and an internal SacII site within the C$_H$2 domain. Mutant C$_H$3 designs were introduced by Kunkel mutagenesis (See Kunkel (1985) Proc Natl Acad Sci; 82(2): 488-492), QUIKCHANGE® site-directed mutagenesis (Agilent), or direct cloning from FRET constructs containing C$_H$3 mutations, using restriction site cloning with EcoRI and an internal SacII site within the C$_H$2 domain. The parental protein sequences for the one-arm antibody constructs, prior to incorporation of the C$_H$3 domain design pair modifications (i.e., WT C$_H$3 domains), are provided in SEQ ID NOs: 1-3.

The three plasmids (0.25 µg anti-c-Met VH-human IgG1 HC (with or without C$_H$3 modifications), 0.25 µg HA-tagged human IgG1 Fc portion (with or without C$_H$3 modifications), and 1.5 µg anti-c-Met light chain) are transiently transfected into 2 mL of HEK293F cells. Transfected cells are grown at 37° C. in a 5% CO$_2$ incubator while shaking at 125 rpm for 5 days. Secreted protein is harvested by centrifugation at 2K rpm for 5 min. and recovery of the supernatant. Expressed protein is purified from the supernatant using PureProteome Protein G Magnetic Beads (EMD Millipore), a DynaMag Magnetic Particle Concentrator (Invitrogen), and Protein G wash and Elution Buffers (Biomiga), as per manufacturer instructions. Eluted samples are neutralized with 1M Tris pH9.0 (Sigma) and filtered with an Ultrafree-MC-GV centrifugal filter (Millipore), per manufacturer instructions.

UPLC Detection: 30 µl samples of expressed protein are added to Waters UPLC tubes, from which 10 µl is injected into a Waters Acquity UPLC with a BEH200 SEC column, equilibrated in PBS and run at 0.3 ml/min. A dilution series of purified MetMab is also run as a standard. Resulting A280 chromatogram peaks from the UPLC traces are deconvoluted and integrated using a custom set of GNU Octave scripts to quantify % heterodimerization by peak area. Tables 2 and 3 below provide heterodimer formation data, as determined by UPLC, for select designs, including further optimized or combination designs. The following provides experimental details of the treatment of the UPLC traces, including various characteristic peaks obtained, as well as procedures employed for curve fitting and data interpretation.

From run to run, the retention times for the various protein species may shift forward and backwards in time together so that if a Chain A HC/Chain B HC heterodimer were to elute at 4.15 m, then the Chain A/Chain A homodimer would elute at 3.8 m, but if the Chain A HC/Chain B HC heterodimer were to elute, for example, 0.35 minutes later at 4.5 m, then the Chain A HC/Chain A. HC homodimer would elute similarly later at 4.1.5 m. A sharp peak between 5.5 and 6.5 m, from a non-antibody species, is characteristic of the UPLC traces, with no recorded species appearing 0.25 m before the peak. A linear baseline absorption is subtracted from all of the UPLC traces. The linear baseline is fit from two points taken as the average absorption between 2.0 m and 2.083 m and the average absorption between 0.25 m and 0.25 m+0.083 m, before the characteristic non-antibody peak at about 6 m. Parameters for the Generalized Exponentially Modified Gaussian (GEMG) curve (Nikitas et al. (2001) J. Chromatog. A, 912: 13-29) are fit for each of the protein species' peaks observed in the traces using data where these peaks are cleanly observed.

The five parameters that describe the shape of the GEMG curves for each of the various species observed in the UPLC traces were fit using traces that unambiguously displayed those species, and then used as seed values for subsequent curve fittings. After the shapes of each of the species were fit, the remaining curves were fit automatically in Octave by scanning the data for peaks and attempting to place the Chain A HC/Chain B HC heterodimer peak in each one and shifting the other peaks with it, miming Octave's fminunc routine to minimize the restrained sum-of-square residuals (SSR), which includes a restraint score on the GEMG-parameter deviations, and then, following optimization, picking the Chain A HC/Chain B HC heterodimer peak assignment that yields the best SSR. For many curves, however, the best SSR does not represent a reasonable interpretation of the data, and so the peak-placement of the Chain A HC/Chain B HC heterodimer is manually determined. The volumes for the peaks are integrated numerically and the molar percentages are then determined by correcting for the absorbance of each species. Otherwise, higher molecular weight contaminants will appear more prominent and lower molecular weight contaminants less prominent than they actually are on a molar basis.

Assessment of Heterodimer Formation by Fluorescence Resonance Energy Transfer (FRET)

To further assess the heterodimer formation potential of Chain A $C_H3$ domain/Chain B $C_H3$ domain design pairs, further constructs incorporating design modifications in the $C_H3/C_H3$ dimer interface are prepared and tested, as described below.

Molecular Biology: The construction of vectors housing oligonucleotide sequences used to express proteins for FRET analysis is performed as follows. Annealed oligos (IDT) are is used to introduce a Myc tag into an in-house vector containing a nucleic acid encoding the mouse kappa leader sequence and a wild type human IgG1 Fc. Two complementary Myc oligos that leave protruding 5' or 3' overhangs for ligation into a vector cut with the appropriate enzymes are designed. The oligos are annealed and ligated into the in-house vector containing the human IgG1 Fc-encoding sequence digested with the appropriate restriction enzymes. After sequence verification, the vector is digested with appropriate enzymes to then introduce the human EGFR Domain 3 (hEGFR D3)- or mouse VEGFR1 Domain 3 (mVEGFR D3)-encoding sequences.

The hEGFR D3 construct was designed using the crystal structures of the extracellular domains of hEGFR bound to cetuximab (PDB ID 1YY9, Structural basis for inhibition of the epidermal growth factor receptor by cetuximab (Li et al. (2005) *Cancer Cell* 7: 301-311)) and the D3 domain, specifically, bound to matuzumab (PDB ID 3C09, Matuzumab binding to EGFR prevents the conformational rearrangement required for dimerization. (Holzel et al. (2008) *Cancer Cell* 13: 365-373)). The hEGFR D3 nucleic acid construct was designed with appropriate restriction sites to enable cloning and was synthesized (IDT®). The hEGFR D3 nucleic acid construct is restriction digested, separated on a 1% agarose gel and the DNA fragment is purified using a Gel Extraction Kit (Qiagen). The purified DNA fragment is ligated into the pcDNA 3.1 mammalian expression plasmid (Life Technologies) between the Myc tag and the human IgG1 Fc, respectively. The construct is then sequence verified for use in subsequent cloning of CH3 designs. A two amino acid, GS, linker is inserted between the EGFR or VEGFR1 D3 domains and the human IgG1-Fc.

The mVEGFR1 D3-encoding sequence is obtained from an in-house source and used as a PCR template. The mVEGFR1 D3 protein binds an in-house generated chimeric Mab (as determined by in-house testing). The mVEGFR1 D3-encoding DNA is amplified by PCR using oligonucleotide primers designed to add restriction sites to enable cloning into the vector (pcDNA containing the Myc tag and human IgG1 Fc encoding sequences). The PCR product is digested with the appropriate restriction enzymes and gel purified. The purified DNA PCR product is then ligated into the pcDNA 3.1 between the Myc tag- and the IgG1 Fc-encoding sequences, respectively. The construct is then sequence verified for use in subsequent cloning of $C_H3$ designs.

The sequence of the hEGFR D3-Fc protein containing the wild-type human IgG1 $C_H3$ domain is provided below in SEQ ID. NO. 4. The sequence of the mVEGFR1 D3-Fc protein containing the wild-type human IgG1 $C_H3$ domain is provided below in SEQ ID. NO. 5. Mutant $C_H3$ designs are introduced by direct GBLOCK® gene cloning (IDT®) using restriction sites BsrGI and EcoRI and/or QUIKCHANGE® site-directed mutagenesis (Agilent).

Each plasmid is scaled-up by transformation into TOP10 *E. coli*, mixed with 100 mL luria broth in a 250 mL baffled flask, and shaken O/N at 220 rpm. Large scale plasmid purifications are performed using the BenchPro 2100 (Life Technologies) or HiSpeed Plasmid Maxi Kit (Qiagen) according to the manufacturer's instructions. For protein production, plasmids harboring the Chain A and Chain B DNA sequences are transfected (1:1 plasmid) into HEK293F cells using Freestyle transfection reagents and protocols provided by the manufacturer (Life Technologies). Transfected cells are grown at 37° C. in a 5% CO2 incubator while shaking at 125 rpm for 5 days. Secreted protein is harvested by centrifugation at 10 K rpm for 5 min. Supernatants are passed through 2 µm filters (both large scale and small scale) for purification.

FRET Detection: The Fab detection reagents for use in the FRET assay are generated as follows. The matuzumab human IgG1 MAb (anti-hEGFR D3) was constructed in-house as described previously (Lewis et al., 2014) and a Fab generated from the matuzumab IgG1 MAb using papain digestion as described previously (Jordan et al. (2009) *Proteins* 77: 832-41). The anti-mVEGFR1 D3 Fab protein is generated in house from published sequences (WO2014/150314). Fluorescent isothiocyanato-activated Europium-W1024 (Perkin Elmer Life Sciences) labeling of the anti-mVEGFR1 D3 and Matuzumab Fabs is performed according to the manufacturer's instructions. Fluorescent Cy5 (Amersham Pharmacia Biotech) labeling of the anti-mVEGFR1 D3 and Matuzumab Fabs is performed according to the manufacturer's instructions.

To test the $C_H3$ designs in the FRET assay, Europium (Eu)-labeled mVEGFR1. D3 Fab, or Eu-labeled Matuzumab FAb (anti-hEGFR D3), is mixed with Cy5-labeled anti-mVEGFR1 D3, or Cy5-labeled Matuzumab Fab to final concentrations of 1.25 µg/ML Eu-reagent, 2.5 µg/mL Cy5-reagent in diluted HEK293F cell culture supernatants containing secreted protein resulting from co-expression of both EGFR-D3-Fc (Chain A) and VEGFR1-D3-Fc (Chain B). The cell culture supernatants are diluted 1:10 or 1:40 in PBS, 10 mg/mL BSA, 0.1% Tween-20 for 1 mL and 2 mL transient transfections, respectively, prior to the FRET measurements. These particular supernatant dilutions result in a roughly 0.5-1 µg/mL final Protein-Fc concentration optimal for measuring the homodimer/heterodimer ratios. Mixing of the Eu- and Cy5-labeled Matuzumab Fabs enables detection of EGFR-D3-Fc AA homodimer. Mixing Eu- and Cy5-labeled anti-VEGFR1-D3 Fabs enables detection of VEGFR1-D3-Fc BB homodimer. Mixing of Eu-labeled anti-VEGFR1-D3 Fab with Cy5-labeled anti-Cy5-labeled Matuzumab enables detection of EGFR-D3-Fc/VEGFR1-D3-Fc AB heterodimer. The simultaneous binding of Eu-labeled Fab and Cy5-labeled Fab to a single protein molecule (either homodimer-Fc or heterodimer-Fc depending on the Fab combinations) results in a time-resolved fluorescence resonance energy transfer (TR-FRET) from the Europium label to the Cy5 label. 96½ well microtiter plates (black from Costar) containing the diluted supernatants and labeled Fabs are incubated for approximately 30 minutes at room temperature. Fluorescence measurements are carried out on a Wallac Envision 2103 Multilabel Reader with a dual mirror (PerkinElmer Life Sciences) with the laser excitation of the Europium at wavelength at 340 nm and the mission filters Europium 615 and APC 665. Delay between excitation and emission was 20 μs.

Assessment of Heterodimer Thermostability by Differential Scanning Calorimetry (DSC)

Generation of Heterodimeric Fcs Suitable for DSC

To assess the thermostability of Chain A $C_H3$ domain/Chain B $C_H3$ domain design pairs, Fc constructs incorporating design modifications in the $C_H3/C_H3$ dimer interface are prepared and tested. To generate Fcs for thermostability analysis, including dimers incorporating $C_H3$ domain design pair mutations, an HA-tagged human IgG1 Fc portion (Chain B $C_H2$-$C_H3$ segment) and a human IgG1 Fc portion (Chain A $C_H2$-$C_H3$ segment) are constructed. The sequence of the HA tagged-human IgG1 Fc portion containing the WT $C_H3$ domain sequence is provided in SEQ ID NO:2. The sequence of the human IgG1 Fc portion (without an HA tag) containing the WT $C_H3$ domain sequence is provided by SEQ ID NO:6.

The $C_H3$ design constructs for use in DSC analysis are made in one of two ways, shuttling from another construct containing a nucleic acid encoding the $C_H3$ design of interest, or site directed mutagenesis. When shuttling between existing constructs, restriction cloning of the $C_H3$ encoding fragment containing the desired mutations is employed. The nucleic acid encoding the $C_H3$ containing the desired mutations is inserted into the vector of interest by digesting both the donor vector and the recipient vector into which the design mutations will be inserted. Both the insert and recipient vector DNA's are purified using gel electrophoresis and the purified insert and receptor vector DNA fragments are then ligated. All ligation constructs are transformed into E. coli strain TOP 10 competent cells (Life Technologies). When site-directed mutagenesis is employed, the basic procedure utilizes a supercoiled double-stranded DNA vector containing the wild-type nucleotide sequence of interest and two synthetic oligonucleotide primers (IDT®) containing the desired mutation. The oligonucleotide primers, each complementary to opposite strands of the vector, are extended during thermal cycling by the DNA polymerase (HotStar HiFidelity Kit, Qiagen Cat.202602). Incorporation of the oligonucleotide primers generates a mutated plasmid. Following temperature cycling, the product is treated with Dpn I enzyme. (New England BioLabs, Cat # R0176) The Dpn I enzyme cleaves only methylated parental DNA. The enzyme digested mutated plasmid is then transformed into E. coli strain TOP 10 competent cells (Life Technologies).

Sequenced plasmids are scaled-up for transfection as described above for the FRET constructs. Plasmids are transfected into 293F using the same protocol as described for the FRET constructs above. Secreted protein is harvested by centrifugation at 10 K rpm for 5 min. Supernatants are passed through 2 μm filters for purification. Purification is performed using protein A chromatography as described by Lewis, et al. (2014), Nat. Biotechnol., 32; 191-198.

Following procedures as described above, $C_H3$ designs are incorporated into the Fc portions containing the WT $C_H3$ domain sequences (SEQ ID NO:2 (Chain B) and SEQ ID NO:6 (Chain A)). Differential scanning calorimetry (DSC) measurements are carried out as generally described in Clark, L. A. et al., 2014 J. Struct. Biol. 185:223-227 with a scan rate of 1.5 deg. C./min. All DSC thermograms are fit using analysis software provided by the manufacturer (GE Healthcare).

Table 2 provides heterodimer formation results (as measured by UPLC and FRET) as well as thermostability data (as determined by DSC) for select designs.

TABLE 2

Heterodimeric potential of computational designs and their thermal stability

| design | CH3 Mutations* | | Total fit | | % heterodimer (FRET signal)[d] | $T_m$ of CH3 (DSC) |
|---|---|---|---|---|---|---|
| | Chain A | Chain B | % heterodimer (UPLC)[a, b] | area [c] UPLC | | |
| WT | | | 51.3 ± 0.7 (12) | 99.5 ± 0.2 | 56.6 | 83 |
| 7.4 | Y407A | T366V K409V | 86 | 98 | 97.5 | 75 |
| 7.8 | Y407A D399M | T366V K409V | 93 | 99 | 85.8 | 71 |
| 11.2 | Y349S K370Y | E357D S364Q | 74 | 99 | 93.6 | 70.67 |

*Mutations are designated by first identifying the one letter abbreviation for the parental amino acid, the amino acid residue number and the one letter abbreviation for the replacement amino acid. For example, Y407A indicates that residue 407 of is modified from a tyrosine (Y) to an alanine (A).

[a] Values represent single UPLC experiments unless numbers appear in parenthesis. Where numbers appear in parenthesis, the values represent the arithmetic mean +/− standard error and the number within the parens represents the number of UPLC experimental repeats.

[b] UPLC peaks were fit using an automated curve fitting protocol, with molar fractions taken as peak volumes normalized by expected extinction coefficients. Because the two chains might not express at equal levels, monomeric impurities are not included when computing the percentage heterodimer.

[c] Total fit area indicates how much of the chromatographic trace can be fit by GEMG curves and suggests how much remains as unidentifiable contaminant species.

[d] This assay should not be considered quantitative. The labeled Fabs and the Fcs are at about equal concentrations, so not all Fcs will be bound to Fabs. When detecting the AA homodimer concentration, some of the anti-EGFR Fabs will be bound to the AB heterodimer, and some AA homodimers will bind to two $Eu^{3+}$-labled Fabs or to two Cy5-labled Fabs and will thus not FRET, or they will bind to only a single Fab and not FRET. The percentages reported are calculated as relative FRET intensities; e.g. % AB = FRET(AB)/(FRET(AA) + FRET(AB) + FRET(BB)).

Table 3 provides additional heterodimer formation results and thermostability data for select initial designs (e.g., Design 7.8) as well as further optimized variants of Design 7.8 and the combination Design 20.8.

TABLE 3

Heterodimeric assembly and thermal stability of computational designs 20.8, 7.8, and optimized variants

| design | CH3 Mutations* Chain A | Chain B | % heterodimer (UFLC) [a, b] | Total fit area [c] | % heterodimer (FRET signal) [d] | Tm of CH3 (DSC) [c] |
|---|---|---|---|---|---|---|
| WT | | | 51.3 ± 0.7 (n = 12) | 99.5 ± 0.2 | 58 | |
| 20.8 | Y349S K370Y T366V K409V | E357D S364Q Y407A | 84.9 ± 1.4 (n = 6) | 99.0 ± .3 | 86 | 69.9, 70.3, 69.5, 70.4 |
| 20.8b | E357D S364Q Y407A | Y349S K370Y T366V K409V | 92.5 ± 0.1 (n = 2) | 100.0 ± .2 | 95 | ND |
| 20.8.26 | Y349S K370Y T366M K409V | E357D S364Q Y407A | 86 | 99 | 96 | |
| 20.8.26b | E357D S364Q Y407A | Y349S K370Y T366M K409V | 93 | 100 | ND | ND |
| 20.8.31 | Y349S T366V K370Y K409V | E357D S364R Y407A | 86.5 ± 3.6 (n = 3) | 99.6 ± .3 | 95 | 68.9, 69.6 |
| 20.8.31b | E357D S364R Y407A | Y349S T366V K370Y K409V | 85 | 100 | ND | ND |
| 20.8.33 | Y349S T366V K370Y K409V | E356G E357D S364Q Y407A | 93 | 99 | 98 | ND |
| 20.8.33b | E356G E357D S364Q Y407A | Y349S T366V K370Y K409V | 92 | 100 | ND | ND |
| 20.8.34 | Y349S K370Y T366M K409V | E356G E357D S364Q Y407A | 83.8 ± 3.5 (n = 3) | 99.9 ± .4 | 95.5 | 68.9 |
| 20.8.34b | E356G E357D S364Q Y407A | Y349S K370Y T366M K409V | 94 | 100 | ND | ND |
| 20.8.37 | Y349S K370Y T366M K409V | E357D S364R Y407A | 83.5 ± 1.7 (n = 2) | 100.0 ± .2 | ND | 68.9 |
| 20.8.37b | E357D S364R Y407A | Y349S K370Y T366M K409V | 85 | 100 | ND | ND |
| 7.8 | Y407A D399M | T366V K409V | 89.9 ± 1.9 (n = 6) | 99.3 ± .3 | 85.8 | 71 |
| 7.8b | T366V K409V | Y407A D399M | 88.6 ± 1.0 (n = 6) | 99.4 ± .2 | 92.2 | ND |
| 7.8.60 | K360D D399M Y407A | E345R Q347R T366V K409V | 93 | 99 | ND | 70.4 |

TABLE 3-continued

Heterodimeric assembly and thermal stability of computational designs 20.8, 7.8, and optimized variants

| design | CH3 Mutations* Chain A | Chain B | % heterodimer (UFLC) [a, b] | Total fit area [c] | % heterodimer (FRET signal) [d] | Tm of CH3 (DSC) [e] |
|---|---|---|---|---|---|---|
| 7.8.60b | E345R Q347R T366V K409V | K360D D399M Y407A | 93.3 ± 1.3 (n = 3) | 99.7 ± .1 | ND | ND |

*Mutations are designated by first identifying the one letter abbreviation for the parental amino acid, the amino acid residue number and the one letter abbreviation for the replacement amino acid. For example, Y407A indicates that residue 407 of is modified from a tyrosine (Y) to an alanine (A).
[a] Values represent single UPLC experiments unless numbers appear in parenthesis. Where numbers appear in parenthesis, the values represent the arithmetic mean +/− standard error and the number within the parens represents the number of UPLC experimental repeats.
[b] UPLC peaks were fit using an automated curve fitting protocol, with molar fractions taken as peak volumes normalized by expected extinction coefficients. Because the two chains might not express at equal levels, monomeric impurities are not included when computing the percentage heterodimer.
[c] Total fit area indicates how much of the chromatographic trace can be fit by GEMG curves and suggests how much remains as unidentifiable contaminant species.
[d] This assay should not be considered quantitative. The labeled Fabs and the Fcs are at about equal concentrations, so not all Fcs will be bound to Fabs. When detecting the AA homodimer concentration, some of the anti-EGFR Fabs will be bound to the AB heterodimer, and some AA homodimers will bind to two $Eu^{3+}$-labled Fabs or to two Cy5-labled Fabs and will thus not FRET, or they will bind to only a single Fab and not FRET. The percentages reported are calculated as relative FRET intensities; e.g. % AB = FRET(AB)/(FRET(AA) + FRET(AB) + FRET(BB)).
[e] Multiple values in the DSC column represent values from duplicate experiments.

The data is Tables 2 and 3 demonstrate that exemplified CH3 designs yield significant enhancement of Chain A/Chain B heterodimerization relative to dimer constructs which contain only wild-type CH3 domains. Select heterodimer-favoring designs are incorporated into complete IgG heavy chains and the assembly of particular IgG bispecific antibodies is assessed as described in Example 2, below.

Example 2

Complete IgG Bispecific Antibodies (IgG1 HC Backbones) Comprising $C_H3/C_H3$ Interface Modifications Four published antibodies (with published sequences) were chosen to generate three IgG BsAbs. The first MAb pair to be expressed as an IgG BsAb consists of pertuzumab (anti-HER-2) (see, Nahta, Hung & Esteva (2004), *Cancer Res.* 64; 2343-2346; and Franklin et al. (2004), *Cancer Cell.* 5(4); 317-28) and BHA10 (anti-LTβR) (see, Michaelson et al. (2009), *mAbs* 1; 128-141; and Jordan et al. (2009), *Proteins* 77(4); 832-41.) The second MAb pair to be expressed as an IgG BsAb consists of a combination of MetMAb (anti-cMET) (see, Jin et al. (2008), *Cancer Res.* 68; 4360-4368; and U.S. Pat. No. 7,892,550) and matuzumab (anti-EGFR) (see, Bier et al. (1998), *Cancer Immunol. Immunother.* 46; 167-173; and Schmiedel et al. (2008) *Cancer Cell.* 13(4); 365-73. doi: 10.1016/j.ccr.2008.02.019.) Lastly, pertuzumab was paired with matuzumab to form a third set of IgG BsAbs. All BsAbs were tested for assembly using select $C_H3$ designs, as described in Example 1, or WT $C_H3$ domain sequences. The $C_H3$ designs are incorporated into the $C_H3$ domains of each parental Mab pair, with each Mab $C_H3$ domain receiving one set of mutations of a particular design pair (i.e, either the A Chain or B Chain mutations), and the other Mab $C_H3$ domain receiving the other set of mutations of the design pair. In addition, each HC and LC prepared and tested included previously described mutations in the Fab region to promote proper HC-LC pairing as well. Matuzumab and BHA10 HCs and LCs contain Design H4WT (+DR_CS), while the pertuzumab and MetMAb HCs and LCs contain Design AB2133 (a), each as described in WO2014/150973 (see also, Lewis et al. (2014), *Nature Biotech.* 32; 191-198 (Designs VRD2, VRD1 and CRD2).

Methods

The plasmids for the IgG BsAbs are obtained in-house (see Lewis et. al (2014) *Nat Biotechnol.* 32; 191-198). The construction of BsAbs with each set of $C_H3$ designs are done in one of the two following ways.

Oligonucleotide primers with 15 base pair extensions (5') that are complementary to the N-termini of the $V_H$ region ($V_H$ forward) and the C-terminus of the $C_H2$ region ($C_H2$ reverse) of the HC are used in a PCR reaction to generate recombinase-compatible inserts of the entire HC except the $C_H3$ domain. A second set of oligonucleotides are used to generate additionally inserts encoding the design-containing $C_H3$ domains. The templates for these additional primers are from the FRET, UPLC or DSC constructs described in Example 1. The 5' primers for the $C_H3$ domain are complementary to the junction between $C_H2$ and $C_H3$ (called $C_H2$ forward) and the 3' primers are complementary to the C-terminus of the $C_H3$ region ($C_H3$ reverse). Both the 5' and 3' primers contain 15 base pair extensions to allow recombinase-based cloning. The PCR products are gel purified. The BsAb vector(s) are digested with 2 different restriction enzymes, removing the $C_H1$, $C_H2$ and $C_H3$ domains. Recombinase-based cloning is performed using the In-Fusion protocol (Clontech Laboratories, Inc.) to generate the each clone for testing. The LC-containing plasmids are constant throughout the experiments.

Alternately, overlapping PCR is used to generate inserts containing the entire IgG constant domains (Casimiro et al. (1997), *Structure* 5; 1407-1412). The resulting single inserts contain 15 base pair 5' and 3' overlaps to allow recombinase-based cloning as described above.

For each of these methods listed above, the new HC-containing vector is then transformed into Dam+*E. coli* (Invitrogen One Shot Top10 Chemically Competent *E. coli*) and plated on LB+Carbenicillin plates 37° C. overnight, Colonies were picked and mutations were verified by sequence analysis. To generate IgG BsAb protein, four plasmids, each containing either a HC or a LC from two separate MAbs, are co-transfected into 2 mL cultures of HEK293F cells using transfection reagent from Life Technologies. The plasmids are transfected at 1.3 μg of each LC and 0.67 μg of each HC into 2 mL cultures. After 5 days of shaking incubation in a $CO_2$ incubator at 37° C., the cell culture supernatants are collected and filtered through 0.2 μm filters. The supernatants are purified, prepared, and analyzed by high pressure liquid chromatography/mass spectrometry (LCMS) as described in Lewis et al., 2014 Nature Biotechnol. 32: 191-198. One deviation was that the proteins are enzymatically deglycosylated after purification and neutralization to approximately pH 8.0 using 1 M Tris, pH 8.5-9.0. Each protein was deglycosylated by the addition of 1 μL N-Glycanase (Prozyme) for 3-14 hrs at 37° C. prior to being submitted for LCMS.

Results

Select $C_H3$ heterodimer designs from Example 1 are constructed in the HCs listed in Table 4. The designs for testing include 7.8, 7.8.60, 20.8, 20.8.26, 20.8.34, and 20.8.37. The HCs and LCs from each antibody pair (4 chains total) are transfected into 293F, cultured for 5 days, purified using protein G capture, and analyzed by LCMS as described in the methods.

TABLE 4

Sequence ID numbers of HC and LC constructs prepared to evaluate heterodimerization potential of $C_H3$ Designs in IgG BsAb Format

| First Parental MAb Constructs ($C_H3$ Design or WT indicated)[a,c] | SEQ ID NO: | Second Parental MAb Constructs ($C_H3$ Design or WT indicated)[b,c] | SEQ ID NO: |
|---|---|---|---|
| pertuzumab HC__WT | 9* | BHA10 HC__WT | 21 |
| pertuzumab HC__7.8__A | 10* | BHA10 HC__7.8__B | 22 |
| pertuzumab HC__7.8.60__A | 11* | BHA10 HC__7.8.60__B | 23 |
| pertuzumab HC__20.8__A | 12* | BHA10 HC__20.8__B | 24 |
| pertuzumab HC__20.8.26__A | 13* | BHA10 HC__20.8.26__B | 24 |
| pertuzumab HC__20.8.34__A | 13* | BHA10 HC__20.8.34__B | 25 |
| pertuzumab HC__20.8.37__A | 13* | BHA10 HC__20.8.37__B | 26 |
| pertuzumab LC | 14 | BHA10 LC | 27 |
| MetMAb HC__WT | 15* | matuzumab HC__WT | 28 |
| MetMAb HC__7.8__B | 16* | matuzumab HC__7.8__A | 29 |

TABLE 4-continued

Sequence ID numbers of HC and LC constructs prepared to evaluate heterodimerization potential of $C_H3$ Designs in IgG BsAb Format

| First Parental MAb Constructs ($C_H3$ Design or WT indicated)[a,c] | SEQ ID NO: | Second Parental MAb Constructs ($C_H3$ Design or WT indicated)[b,c] | SEQ ID NO: |
|---|---|---|---|
| MetMAb HC__7.8.60__B | 17* | matuzumab HC__7.8.60__A | 31 |
| MetMAb HC__20.8__A | 18* | matuzumab HC__20.8__B | 33 |
| MetMAb HC__20.8.26__A | 19* | matuzumab HC__20.8.26__B | 33 |
| MetMAb HC__20.8.34__A | 19* | matuzumab HC__20.8.34__B | 34 |
| MetMAb HC__20.8.37__A | 19* | matuzumab HC__20.8.37__B | 35 |
| MetMAb LC | 20 | matuzumab LC | 36 |
| pertuzumab HC__WT | 9* | matuzumab HC__WT | 28 |
| pertuzumab HC__7.8__A | 10* | matuzumab HC__7.8__B | 30 |
| pertuzumab HC__7.8.60__A | 11* | matuzumab HC__7.8.60__B | 32 |

[a]The pertuzumab and MetMab HC and LC constructs also comprise the Fab Design AB2133(a) mutations as described in WO2014/150973 (HC: $V_H$__Q39K, R62E; $C_H1$__H172A, F174G/LC: $V_L$__D1R, Q38D; $C_L$__L135Y, S176W),
[b]The BHA10 and matuzumab HC and LC constructs also comprise the Fab Design H4WT(+DR__CS) mutations as described in WO2014/150973 (HC: $V_H$__Q39Y, Q105R; $C_H1$__S127C, K228D, C230G/LC: $V_L$__Q38R, K42D; $C_L$__D122K),
[c]The designation "A" following a $C_H3$ domain design number indicates that the HC contains one of the member set of $C_H3$ mutations of the given design number mutation pair, and the designation "B" indicates that the HC contains the corresponding member set of $C_H3$ mutations of the given design number.
*Sequence also comprises an N297Q mutation in the CH12 domain to reduce glycosylation heterogeneity to facilitate LCMS analysis The results of the LCMS data indicate that the exemplified $C_H3$ heterodimer designs from Example 1 which were incorporated into the IgG BsAb format resulted in improved correct IgG BsAb assembly (Table 5). Using the wild-type $C_H3$, the average percentage of heterodimer is found to be 49%—almost identical to the theoretical level expected if both HCs express equally well and there is no bias for heterodimer formation. When the designs are added to the $C_H3$ domain, similar percentages of heterodimer are observed by LCMS of the IgG BsAbs as the percentages found in Example 1 by UPLC and FRET using the MetMAb and FRET constructs.

TABLE 5

Specific Assembly of IgG BsAbs or Mis-matched Species Incorporating WT CH3 Domains or Select CH3 Designs Pertuzumab × BHA10 IgG BsAbs (with or without CH3 Designs)

| Pertuzumab parental Mab CH3 Design or WT [a, c] (HCA* + LC1) | BHA10 parental Mab CH3 Design or WT [b, c] (HCB + LC) | % AB (LC1/LC2) (correct IgG BsAb assembly) | % AA Homodimer (incorrect assembly) | % BB Homodimer (incorrect assembly) | % AB (2x LC1) (incorrect assembly) | % AB (2x LC2) (incorrect assembly) |
|---|---|---|---|---|---|---|
| WT__A (SEQ ID 9 + 14) | WT__B (SEQ ID 21 + 27) | 52.6 | 18.5 | 28.9 | 0 | 0 |
| 7.8__A (SEQ ID 10 + 14) | 7.8__B (SEQ ID 22 + 27) | 69.3 | 0 | 15.1 | 15.6 | 0 |
| 7.8.60__A (SEQ ID 11 + 14) | 7.8.60__B (SEQ ID 23 + 27) | 95.2 | 0.7 | 1.6 | 0 | 2.5 |
| 20.8__A (SEQ ID 12 + 14) | 20.8__B (SEQ ID 24 + 27) | 96.5 | 3.5 | 0 | 0 | 0 |
| 20.8.26__A (SEQ ID 13 + 14) | 20.8.26__B (SEQ ID 24 + 27) | 96.9 | 3.1 | 0 | 0 | 0 |
| 20.8.34__A (SEQ ID 13 + 14) | 20.8.34__B (SEQ ID 25 + 27) | 90.3 | 0 | 0 | 9.7 | 0 |
| 20.8.37__A (SEQ ID 13 + 14) | 20.8.37__B (SEQ ID 26 + 27) | 89.6 | 2.9 | 0 | 7.5 | 0 |

TABLE 5-continued

Specific Assembly of IgG BsAbs or Mis-matched Species Incorporating WT CH3 Domains or Select CH3 Designs

MetMAb × Matuzumab IgG BsAbs (with or without CH3 Designs)

| MetMAb parental MAb CH3 Design or WT [a, c] (HCA* + LC1) | Matuzumab parental MAb CH3 Design or WT [b, c] (HCB + LC) | % AB (LC1/LC2) (correct IgG BsAb assembly) | % AA Homodimer (incorrect assembly) | % BB Homodimer (incorrect assembly) | % AB (2x LC1) (incorrect assembly) | % AB (2x LC2) (incorrect assembly) |
|---|---|---|---|---|---|---|
| WT_A (SEQ ID 15 + 20) | WT_B (SEQ ID 28 + 36) | 42 | 0 | 58 | 0 | 0 |
| 7.8_B (SEQ ID 16 + 20) | 7.8_A* (SEQ ID 29 + 36) | 100 | 0 | 0 | 0 | 0 |
| 7.8.60_B (SEQ ID 17 + 20) | 7.8.60_A* (SEQ ID 31 + 36) | 90.8 | 0 | 0 | 9.2 | 0 |
| 20.8_A (SEQ ID 18 + 20) | 20.8_B (SEQ ID 33 + 36) | 75.6 | 0 | 0 | 0 | 24.4 |
| 20.8.26_A (SEQ ID 19 + 20) | 20.8.26_B (SEQ ID 33 + 36) | 58.6 | 8.1 | 0 | 0 | 33.3 |
| 20.8.34_A (SEQ ID 19 + 20) | 20.8.34_B (SEQ ID 34 + 36) | 95.8 | 0 | 0 | 0 | 4.2 |
| 20.8.37_A (SEQ ID 19 + 20) | 20.8.37_B (SEQ ID 35 + 36) | 79.1 | 0 | 0 | 0 | 20.9 |

Pertuzumab × Matuzumab IgG BsAbs (with or without CH3 Designs)

| Pertuzumab parental MAb CH3 Design or WT [a, c] (HCA* + LC1) | Matuzumab parental MAb CH3 Design or WT [b, c] (HCB + LC) | % AB (LC1/LC2) (correct IgG BsAb assembly) | % AA Homodimer (incorrect assembly) | % BB Homodimer (incorrect assembly) | % AB (2x LC1) (incorrect assembly) | % AB (2x LC2) (incorrect assembly) |
|---|---|---|---|---|---|---|
| WT_A (SEQ ID 9 + 14) | WT_B (SEQ ID 28 + 36) | 53.1 | 26.9 | 20 | 0 | 0 |
| 7.8_A (SEQ ID 10 + 14) | 7.8_B (SEQ ID 30 + 36) | 95.4 | 0.5 | 2.9 | 0 | 1.2 |
| 7.8.60_A (SEQ ID 11 + 14) | 7.8.60_B (SEQ ID 32 + 36) | 98.1 | 0.6 | 1.3 | 0 | 0 |
| 20.8_A (SEQ ID 12 + 14) | 20.8_B (SEQ ID 33 + 36) | 96 | 2.1 | 2 | 0 | 0 |
| 20.8.26_A (SEQ ID 13 + 14) | 20.8.26_B (SEQ ID 33 + 36) | 95.2 | 1.8 | 2.9 | 0 | 0 |
| 20.8.34_A (SEQ ID 13 + 14) | 20.8.34_B (SEQ ID 34 + 36) | 96.9 | 1.5 | 1.6 | 0 | 0 |
| 20.8.37_A (SEQ ID 13 + 14) | 20.8.37_B (SEQ ID 35 + 36) | 97.6 | 2.0 | 0.5 | 0 | 0 |

[a] The pertuzumab and MetMab HC and LC constructs also comprise the Fab Design AB2133(a) mutations as described in WO2014/150973 (HC: $V_H\_Q39K$, R62E; $C_H1\_H172A$, F174G/LC: $V_L\_D1R$, Q38D; $C_L\_L135Y$, S176W),
[b] The BHA10 and matuzumab HC and LC constructs also comprise the Fab Design H4WT(+DR_CS) mutations as described in WO2014/150973 (HC: $V_H\_Q39Y$, Q105R; $C_H1\_S127C$, K228D, C230G/LC: $V_L\_Q38R$, K42D; $C_L\_D122K$),
[c] The designation "A" following a CH3 domain design number indicates that the HC contains one of the member set of CH3 mutations of the given design number mutation pair, and the designation "B" indicates that the HC contains the corresponding member set of CH3 mutations of the given design number.
*Heavy chain SEQ ID NOs 9-13 and 15-19 also comprises an N297Q mutation in the CH2 domain to reduce glycosylation heterogeneity to facilitate LCMS analysis Conclusions The data in Table 5 clearly demonstrates that designs 7.8, 7.8.60, 20.8, 20.8.26, 20.8.34 and 20.8.37 improve the assembly of the desired heterotetrameric IgG BsAbs (i.e., HCA/LC1+HCB/LC2) over what was observed with the WT $C_H3$ s. The strong correlation between the % heterodimer induced by each design described in Example and the % heterodimer induced within the IgG BsAbs in Example 2 suggests that all of the exemplified designs from Example 1 that improved heterodimer formation based on the UPLC and FRET assays will improve the percentage of heterodimer within the IgG BsAbs format.

Example 3

Complete IgG Bispecific Antibodies (IgG4 HC Backbones) Comprising $C_H3/C_H3$ Interface Modifications Using the same parental Mab pairs as described in Example 2, complete IgG Bispecific Antibodies comprising select $C_H3$ designs and fully IgG4 constant domains in each heavy chain are constructed. As in Example 2, the $C_H3$ designs are incorporated into the $C_H3$ domains of each parental Mab pair, with each Mab $C_H3$ domain receiving one set of mutations of a particular design pair (i.e, either the A Chain or B Chain mutations), and the other Mab $C_H3$ domain receiving the other set of mutations of the design pair. Each HC and LC prepared also included the previously described mutations in the Fab region to promote proper HC-LC pairing as well. Matuzumab and BHA10 HCs and LCs contain Design H4WT (+DR_CS), while the pertuzumab and MetMAb HCs and LCs contain Design AB2133 (a), each as described in WO2014/150973 (see also, Lewis et al. (2014), *Nature Biotech.* 32; 191-198 (Designs VRD2, VRD1 and CRD2). Further, to make the resulting IgG BsAb proteins more homogeneous and amenable to eventual LCMS analyses, serine 241 (Kabat Numbering) was mutated to proline (S241P) to reduce natural IgG4 half-antibody formation (see, Aalberse, R. C. and Schuurman, J. Immunology, 105, 9-19 (2002)). Additionally, asparagine 297 was mutated to glutamine (N297Q) to eliminate N-linked glycosylation. Lastly, the IgG4 lower hinge regions contain a double alanine mutation at positions 234 and 235 that have been previously described.

Molecular Biology

DNA encoding complete IgG4 constant domain regions, containing both the Fab ($C_H1$) specificity designs and $C_H3$ hetero-dimerization designs, are constructed in separate pieces or "blocks" as follows. A DNA block coding for the human IgG4 $C_H1$ region is prepared which contains a 5' region overlapping with an NheI restriction site located behind the variable domain-encoding regions in the expression cassette. A second DNA block coding for the human IgG4 $C_H2$-$C_H3$ region, containing a BSU361 restriction site at the beginning of the $C_H2$ encoding region, a PshAI site at the 3' end of the $C_H2$ encoding region, and a 3' region overlapping within the EcoRI site of a template IgG1 expression cassette is also prepared. Two $C_H2$-$C_H3$ DNA blocks are prepared for each heavy chain of each parental Mab, one containing the hetero-dimerization design 7.8.60 mutations (either the "A" or "B" side mutations) and the other containing the design 20.8.34 mutations (either the "A" or "B" side mutations) The pertuzumab and metMAb constructs are designed to contain the "AB2133a" encoding Fab ($C_H1$) design mutations and the 'A' side mutations for either 7.8.60 or 20.8.34, whereas the matuzumab and BHA10 constructs are designed to contain the "H4WT(+DR_CS)" encoding Fab ($C_H1$) designs and the 'B' side mutations for either 7.8.60 or 20.8.34. Overlapping PCR is performed with the $C_H1$ and the $C_H2$-$C_H3$ DNA blocks to generate inserts containing the entire human IgG4 constant domains (Casimiro et al, (1997), *Structure* 5; 1407-1412). The complete IgG4 constant domain constructs are then amplified prior to cloning into mammalian expression vectors.

Mammalian expression plasmids encoding human IgG1 heavy chains for each of pertuzumab, metMab, matuzumab, and BHA10, as previously described (Lewis et. Al, Nat. Biotechnol, 32(2); 191-198 (2014)), are cut at restriction sites (NheI and EcoRI) at the 5' and 3' ends of the heavy chain constant domain coding region to allow excision of the IgG1 constant domain-encoding sequences. The linearized vectors are then purified using a DNA gel extraction kit (Qiagen, Cat. No. 28706) according to the manufacturer's protocol. The human IgG4 constant domain encoding constructs are then cloned into the previously cut expression plasmid using Gibson Assembly® Master Mix (New England Biolabs). All constructs utilized a murine kappa leader signal sequence that is cleaved upon secretion. Ligated constructs are transformed into chemically competent Top 10 *E. Coli* cells (Life Technologies) for scale up. Colonies are selected using an ampicillin selection marker, cultured, and final plasmids are prepared (Qiagen Mini Prep Kit). Correct sequences are confirmed by in-house DNA sequencing.

Complete IgG BsAbs are expressed in HEK293F cells as described in Example 2 above and as provided in Lewis et al., cited above. The heavy chain and light chain components of the complete IgG bispecific antibodies, constructed in IgG4 heavy chain backbones, and their corresponding sequences, are provide in Table 6 below.

TABLE 6

Sequence ID numbers of HC and LC constructs prepared to evaluate heterodimerization potential of $C_H3$ Designs in IgG BsAb Format (IgG4 HC backbone)

| First Parental MAb Constructs ($C_H3$ Design or WT indicated)[a, c] | SEQ ID NO: | Second Parental MAb Constructs ($C_H3$ Design or WT indicated)[b, c] | SEQ ID NO: |
|---|---|---|---|
| pertuzumab HC_7.8.60_A | 47* | BHA10 HC_7.8.60_B | 56* |
| pertuzumab HC_20.8.34_A | 48* | BHA10 HC_20.8.34_B | 57* |
| pertuzumab LC | 49 | BHA10 LC | 58 |
| MetMAb HC_7.8.60_A | 50* | matuzumab HC_7.8.60_B | 53* |
| MetMAb HC_20.8.34_A | 51* | matuzumab HC_20.8.34_B | 54* |
| MetMAb LC | 52 | matuzumab LC | 55 |

[a] The pertuzumab and MetMab HC and LC constructs also comprise the Fab Design AB2133(a) mutations as described in WO2014/150973 (HC: $V_H$_39K, 62E; $C_H1$_172A, 174G/LC: $V_L$_1R, 38D; $C_L$_135Y, 176W),
[b] The BHA10 and matuzumab HC and LC constructs also comprise the Fab Design H4WT(+DR_CS) mutations as described in WO2014/150973 (HC: $V_H$_39Y, 105R; $C_H1$_127C, 228D, 230G/LC: $V_L$_38R, 42D; $C_L$_122K),
[c] The designation "A" following a $C_H3$ domain design number indicates that the HC contains one of the member set of $C_H3$ mutations of the given design number mutation pair, and the designation "B" indicates that the HC contains the corresponding member set of $C_H3$ mutations of the given design number.
*Sequence also comprises 297Q mutation (EU Index Numbering), a 241P mutation (Kabat Numbering) and a 234A, 235A double mutation (EU Index Numbering).

UPLC Purification and Mass Spectromeric Analysis of IgG Bispecific Antibodies

After a five day culture, small scale purifications of prepared IgG BsAbs (in human IgG4 heavy chain backbones) from 450 μL mammalian cell culture supernatants are performed using a multidimensional Dionex UPLC system. A protein G column (POROS® G 20 μm Column, 2.1×30 mm, 0.1 mL part #. 2-1002-00) is equilibrated with 1×PBS prior to sample load. 450 μL of each cell culture supernatant (filtered using 0.2 μM syringe filters, Millipore) are injected onto the protein G column. After washing with 1×PBS, the BsAbs are eluted with 100 mM sodium phosphate, pH 2.2 (2 minutes at 1 ml/min). Titers are determined using the ultraviolet peak area at 280 nm upon elution, with calculations based upon a standard curve created with an in-house mAb. Protein G eluted peak samples are collected into vials in an autosampler held at ambient temperature.

Mass spectrometry is used to quantify bispecific antibody assembly from the purified samples. Experiments are performed using Q-ToF (Waters Technologies) mass spectrometer (MS) with a Xevo source. Samples are introduced into the MS using an Acquity UPLC system (Waters Technologies) connected in-line with a Reversed Phase column (ThermoScientific, Proswift™, RP-4H, 1×50 mm i.d.) at a flow rate of 200 uL/min. To eliminate salts and non-volatile buffers not compatible with MS, gradient elution was performed using 0.1% formic acid in H$_2$O (Solvent A) and 0.1% formic acid in acetonitrile (Solvent B). Mass spectrometry is accomplished in positive ion mode with 2.6 kV capillary voltage at a 150° C. source temperature. Data processing and interpretation of LC-MIS runs is done in BiopharmLynx (a MassLynx Software application manager) using spectral summation over the chromatographic elution profile of the antibody.

The peak areas of the deconvoluted mass spectra are used to calculate the percent of each species, with the expectation that each of the IgG4 BsAb proteins with a mass near 145 kDa (whether assembled correctly or misassembled) are ionized with a similar efficiency. Results are provided in Table 7, below.

Conclusions

The data in Table 7 demonstrates that designs 7.8.60 and 20.8.34, when applied to the human IgG4 constant domains, and paired with the Fab designs, induce predominantly correct assembly (>90%) of the desired heterotetrameric IgG BsAbs (i.e., HCA/LC1+HCB/LC2) over the misassembled protein products. No LC mispairing (existence of two of the same LCs on a HC heterodimer) was observed for any of the IgG BsAbs in the human IgG4 heavy chain backbones. Small levels of homodimeric HC products were observed (either AA homodimer or BB homodimer), however, the clear main peak for each of the six BsAbs prepared was the desired IgG BsAb.

TABLE 7

Specific Assembly of IgG BsAbs (IgG4 HC backbone) or Mis-matched Species Incorporating Select CH3 Designs Pertuzumab × BHA10 IgG BsAbs (with select CH3 Designs)

| Pertuzumab parental MAb CH3 Design or WT[a,c] (HCA* + LC1) | BHA10 parental MAb CH3 Design or WT[b,c] (HCB* + LC2) | % AB (LC1/LC2) (correct IgG BsAb assembly) | % AA Homodimer (incorrect assembly) | % BB Homodimer (incorrect assembly) | % AB (2x LC1) (incorrect assembly) | % AB (2x LC2) (incorrect assembly) |
|---|---|---|---|---|---|---|
| 7.8.60_A (SEQ ID 47 + 49) | 7.8.60_B (SEQ ID 56 + 58) | 95.8 ± 3.7 | 0.0 ± 0.0 | 4.2 ± 3.7 | 0.0 ± 0.0 | 0.0 ± 0.0 |
| 20.8.34_A (SEQ ID 48 + 49) | 20.8.34_B (SEQ ID 57 + 58) | 94.8 ± 0.6 | 5.2 ± 0.6 | 0.0 ± 0.0 | 0.0 ± 0.0 | 0.0 ± 0.0 |

MetMAb × Matuzumab IgG BsAbs (with select CH3 Designs)

| MetMAb parental MAb CH3 Design or WT[a,c] (HCA* + LC1) | Matuzumab parental MAb CH3 Design or WT[b,c] (HCB* + LC2) | % AB (LC1/LC2) (correct IgG BsAb assembly) | % AA Homodimer (incorrect assembly) | % BB Homodimer (incorrect assembly) | % AB (2x LC1) (incorrect assembly) | % AB (2x LC2) (incorrect assembly) |
|---|---|---|---|---|---|---|
| 7.8.60_A (SEQ ID 50 + 52) | 7.8.60_B (SEQ ID 53 + 55) | 100 | 0.0 ± 0.0 | 0.0 ± 0.0 | 0.0 ± 0.0 | 0.0 ± 0.0 |
| 20.8.34_A (SEQ ID 51 + 52) | 20.8.34_B (SEQ ID 54 + 55) | 100 | 0.0 ± 0.0 | 0.0 ± 0.0 | 0.0 ± 0.0 | 0.0 ± 0.0 |

Pertuzumab × Matuzumab IgG BsAbs (with select CH3 Designs)

| Pertuzumab parental MAb CH3 Design or WT[a,c] (HCA* + LC1) | Matuzumab parental MAb CH3 Design or WT[b,c] (HCB* + LC2) | % AB (LC1/LC2) (correct IgG BsAb assembly) | % AA Homodimer (incorrect assembly) | % BB Homodimer (incorrect assembly) | % AB (2x LC1) (incorrect assembly) | % AB (2x LC2) (incorrect assembly) |
|---|---|---|---|---|---|---|
| 7.8.60_A (SEQ ID 47 + 49) | 7.8.60_B (SEQ ID 53 + 55) | 90.9 ± 1.7 | 9.1 ± 1.7 | 0.0 ± 0.0 | 0.0 ± 0.0 | 0.0 ± 0.0 |
| 20.8.34_A (SEQ ID 48 + 49) | 20.8.34_B (SEQ ID 54 + 55) | 94.1 ± 3.7 | 2.3 ± 2.2 | 3.6 ± 1.5 | 0.0 ± 0.0 | 0.0 ± 0.0 |

[a]The pertuzumab and MetMab HC and LC constructs also comprise the Fab Design AB2133(a) mutations as described in WO2014/150973 (HC: V$_H$_39K, 62E; C$_H$1_172A, 174G/LC: V$_L$_1R, 38D; C$_L$_135Y, 176W),
[b]The BHA10 and matuzumab HC and LC constructs also comprise the Fab Design H4WT(+DR_CS) mutations as described in WO2014/150973 (HC: V$_H$_39Y, 105R; C$_H$1_127C, 228D, 230G/LC: V$_L$_38R, 42D; C$_L$_122K),
[c]The designation "A" following a CH3 domain design number indicates that the HC contains one of the member set of CH3 mutations of the given design number mutation pair, and the designation "B" indicates that the HC contains the corresponding member set of CH3 mutations of the given design number.
*Heavy chain SEQ ID NOs 47, 48, 50, 51, 53, 54, 56 and 57 also comprise a 297Q mutation (EU index Numbering), a 241P mutation (Kabat Numbering) and a 234A 235A double mutation (EU index Numbering)

Sequences

SEQ ID. NO: 1 (5D5 heavy chain (WT CH3))
EVQLVESGGGLVQPGGSLRLSCAASGYTFTSYWLHWVRQAPGKGLEWVGMIDP
SNSDTRFNPNFKDRFTISADTSKNTAYLQMNSLRAEDTAVYYCATYRSYVTPLD
YWGQGTLVTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKRV
EPKSCDKTHTCPPCPAPELLGGPSWLFPPKPKDTLMISRTPEVTCVVVDVSHEDP
EVKFNWYVDGVEVHNAKTKPREEQYNSTYRVVSVLTVLHQDWLNGKEYKCKV
SNKALPAPIEKTISKAKGQPREPQVYTLPPSREEMTKNQVSLTCLVKGFYPSDIAV
EWESNGQPENNYKTTPPVLDSDGSFFLYSKLTVDKSRWQQGNVFSCSVMHEALH
NHYTQKSLSLSPGK SEQ ID. NO: 2 (Human IgG1 Fc (HA-tagged, WT CH3))
YPYDVPDYASGSGSDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWL
NGKEYKCKVSNKALPAPIEKTISKAKGQPREPQVYTLPPSREEMTKNQVSLTCLV
KGFYPSDIAVEWESNGQPENNYKTTPPVLDSDGSFFLYSKLTVDKSRWQQGNVF
SCSVMHEALHNHYTQKSLSLSPGK SEQ ID. NO: 3 (5D5 light chain)
DIQMTQSPSSLSASVGDRVTITCKSSQSLLYTSSQKNYLAWYQQKPGKAPKLLIY
WASTRESGVPSRFSGSGSGTDFTLTISSLQPEDFATYYCQQYYAYPWTFGQGTKV
EIKRTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC SEQ ID. NO: 4 (Myc-EGFR D3-Human IgG1 Fc (WT CH3))
EQKLISEEDDLSGSEERKVCNGIGIGEFKDSLSINATNIKHFKNCTSISGDLHILPVAF
RGDSFTHTPPLDPQELDILKTVKEITGFLLIQAWPENRTDLHAFENLEIIRGRTKQH
GQFSLAVVSLNITSLGLRSLKEISDGDVIISGNKNLCYANTINWKKLFGTSGQKTKI
ISNRGENSCKATGQVCHALCSPEGCWGPEPRDCVSCRNVSRGRECVDKGSDKTH
TCPPCPAPELLGGPSVFLFPPKPKDTLMISRTPEVTCVVVDVSHEDPEVKFNWYV
DGVEVHNAKTKPREEQYNSTSTYRVVSVLTVLHQDWLNGKEYKCKVSNKALPAPI
EKTISKAKGQPREPQVYTLPPSREEMTKNQVSLTCLVKGFYPSDIAVEWESNGQP
ENNYKTTPPVLDSDGSFFLYSKLTVDKSRWQQGNVFSCSVMHEALHNHYTQKSL
SLSPGK SEQ ID. NO: 5. (Myc-mVEGFR1 D3-Human IgG1 Fc (WT CH3))
EQKLISEEDLSGSQTNTILDVQIRPPSPVRLLHGQTLVLNCTATTELNTRVQMSWN
YPGKATKRASIRQRIDRSHSHNNVFHSVLKINNVESRDKGLYTCRVKSGSSFQSF
NTSVHGSDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKC
KVSNKALPAPIEKTISKAKGQPREPQVYTLPPSREEMTKNQVSLTCLVKGFYPSDI
AVEWESNGQPENNYKTTPPVLDSDGSFFLYSKLTVDKSRWQQGNVFSCSVMHE
ALHNHYTQKSLSLSPGK SEQ ID. NO: 6. (WT Human IgG1 Fc with lower hinge)
DKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKAL
PAPIEKTISKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEALHNHYT
QKSLSLSPGK SEQ ID NO: 7. Human IgG1 Fc_(7.4_A CH3)
APELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKA
KGQPREPQVYTLPPSREEMTKNQVSLTCLVKGFYPSDIAVEWESNGQPENNYKT
TPPVLDSDGSFFLASKLTVDKSRWQQGNVFSCSVMHEALHNHYTQKSLSLSPGK SEQ ID NO: 8. Human IgG1 Fc_(7.4_B + 366M CH3)
APELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKA
KGQPREPQVYTLPPSREEMTKNQVSLMCLVKGFYPSDIAVEWESNGQPENNYKT
TPPVLDSDGSFFLYSVLWDKSRWQQGNVFSCSVMHEALHNHYTQKSLSLSPGK SEQ ID. NO: 9. (Pertuzunmb HC_(AB2133a Fab + WT CH3 with N297Q))
EVQLVESGGGLVQPGGSLRLSCAASGFTFDYTMDWVRKAPGKGLEWVADVNP
NSGGSIYNQEFKGRFTLSVDRSKNTLYLQMNSLRAEDTAVYYCARNLGPSFYFD
YWGQGTLVTVSSASTKGPSVFPLAPSSKSTSGGTAALGCLVKDYFPEPVTVSWNS
GALTSGVATGPAVLQSSGLYSLSSVVTVPSSSLGTQTYICNVNHKPSNTKVDKKV
EPKSCDKTHTCPPCPAPELLGGPSVFLFPPKPKDTLMISRTPEVTCVVVDVSHEDP
EVKFNWYVDGVEVHNAKTKPREEQYQSTYRVVSVLTVLHQDWLNGKEYKCKV
SNKALPAPIEKTISKAKGQPREPQVYTLPPSREEMTKNQVSLTCLVKGFYPSDIAV
EWESNGQPENNYKTTPPVLDSDGSFFLYSKLTVDKSRWQQGNVFSCSVMHEALH
NHYTQKSLSLSPGK SEQ ID NO. 10. (Pertuzumab HC_(AB2133a Fab + 7.8_A CH3 with N297Q))
EVQLVESGGGLVQPGGSLRLSCAASGFTFDYTMDWVRKAPGKGLEWVADVNP
NSGGSIYNQEFKGRFTLSVDRSKNTLYLQMNSLRAEDTAVYYCARNLGPSFYFD
YWGQGTLVTVSSASTKGPSVFPLAPSSKSTSGGTAALGCLVKDYFPEPVTVSWNS
GALTSGVATGPAVLQSSGLYSLSSVVTVPSSSLGTQTYICNVNHKPSNTKVDKKV

| Sequences |
| --- |
| EPKSCDKTHTCPPCPAPELLGGPSVFLFPPKPKDTLMISRTPEVTCVVVDVSHEDP<br>EVKFNWYVDGVEVHNAKTKPREEQYQSTYRVVSVLTVLHQDWLNGKEYKCKV<br>SNKALPAPIEKTISKAKGQPREPQVYTLPPSREEMTKNQVSLTCLVKGFYPSDIAV<br>EWESNGQPENNYKTTPPVLMSDGSFFLASKLTVDKSRWQQGNVFSCSVMHEAL<br>HNHYTQKSLSLSPGK<br><br>SEQ ID. NO: 11. (Perturtumab HC_(AB2133a Fab + 7.8.60_A CH3 with N297Q))<br>EVQLVESGGGLVQPGGSLRLSCAASGFTFTDYTMDWVRKAPGKGLEWVADVNP<br>NSGGSIYNQEFKGRFTLSVDRSKNTLYLQMNSLRAEDTAVYYCARNLGPSFYFD<br>YWGQGTLVTVSSASTKGPSVFPLAPSSKSTSGGTAALGCLVKDYFPEPVTVSWNS<br>GALTSGVATGPAVLQSSGLYSLSSVVTVPSSSLGTQTYICNVNHKPSNTKVDKKV<br>EPKSCDKTHTCPPCPAPELLGGPSVFLFPPKPKDTLMISRTPEVTCVVVDVSHEDP<br>EVKFNWYVDGVEVHNAKTKPREEQYSTYRVVSVLTVLHQDWLNGKEYKCKV<br>SNKALPAPIEKTISKAKGQPREPQVYTLPPSREEMTDNQVSLTCLKGFYPSDIAV<br>EWESNGQPENNYKTTPPVLMSDGSFFLASKLTVDKSRWQQGNVFSCSVMHEAL<br>HNHYTQKSLSLSPGK<br><br>SEQ ID. NO: 12. (Pertuzumab HC (AB2133a Fab +_20.8_A Ch3 with N297Q))<br>EVQLVESGGGLVQPGGSLRLSCAASGFTFTDYTMDWVRKAPGKGLEWVADVNP<br>NSGGSIYNQEFKGRFTLSVDRSKNTLYLQMNSLRAEDTAVYYCARNLGPSFYFD<br>YWGQGTLVTVSSASTKGPSVFPLAPSSKSTSGGTAALGCLVKDYFPEPVTVSWNS<br>GALTSGVATGPAVLQSSGLYSLSSVVTVPSSSLGTQTYICNVNHKPSNTKVDKKV<br>EPKSCDKTHTCPPCPAPELLGGPSVFLFPPKPKDTLMISRTPEVTGVVVDVSHEDP<br>EVKFNWYVDGVEVHNAKTKPREEQYQSTYRVVSVLTVLHQDWLNGKEYKCKV<br>SNKALPAPIEKTISKAKGQPREPQVSTLPPSREEMTKNQVSLVCLVYGFYPSDIAV<br>EWESNGQPENNYKTTPPVLDSDGSFFLYSVLTVDKSRWQQGNVFSCSVMHEALH<br>NHYTQKSLSLSPGK<br><br>SEQ ID. NO: 13. (Pertuzumab HC_(AB2133a Fab + 20.8.26_A, 20.8.34_A or<br>20.8.37_A CH3 with N297Q) )<br>EVQLVESGGGLVQPGGSLRLSCAASGFTFTDYTMDWVRKAPGKGLEWVADVNP<br>NSGGSIYNQEFKGRFTLSVDRSKNTLYLQMNSLRAEDTAVYYCARNLGPSFYFD<br>YWGQGTLVTVSSASTKGPSVFPLAPSSKSTSGGTAALGCLVKDYFPEPVTVSWNS<br>GALTSGVATGPAVLQSSGLYSLSSVVTVPSSSLGTQTYICNVNHKPSNTKVDKKV<br>EPKSCDKTHTCPPCPAPELLGGPSVFLFPPKPKDTLMISRTPEVTCVVVDVSHEDP<br>EVKFNWYVDGVEVHNAKTKPREEQYQSTYRVVSVLTVLHQDWLNGKEYKCKV<br>SNKALPAPIEKTISKAKGQPREPQVSTLPPSREEMTKNQVSLMCLVYGFYPSDIAV<br>EWESNGQPENNYKTTPPVLDSDGSFFLYSVLTVDKSRWQQGNVFSCSVMHEALH<br>NHYTQKSLSLSPGK<br><br>SEQ ID. NO: 14. (Pertuzumab LC (AB2133a Fab))<br>RIQMTQSPSSLSASVGDRVTITCKASQDVSIGVAWYQDKPGKAPKLLIYSASYRY<br>TGVPSRFSGSGSGTDFTLTISSLQPEDFATYYCQQYYIYPYTFGQGTKVEIKGQPK<br>AAPSVTLFPPSSEELQANKATLVCYISDFYPGAVTVAWKADSSPVKAGVETTTPS<br>KQSNNKYAAWSYLSLTPEQWKSHRSYSCQVTHEGSTVEKTVAPTEC<br><br>SEQ ID. NO: 15. (Met HC_(AB2133a Fab + WT CH3 with N297Q))<br>EVQLVESGGGLVQPGGSLRLSCAASGYTFTSYWLHWVRKAPGKGLEWVGMIDP<br>SNSDTRFNPEFKDRFTISADTSKNTAYLQMNSLRAEDTAVYYCATYRSYVTPLDY<br>WGQGTLVTVSSASTKGPSVFPLAPSSKSTSGGTAALGCLVKDYFPEPVTVSWNSG<br>ALTSGVATGPAVLQSSGLYSLSSVVTVPSSSLGTQTYICNVNHKPSNTKVDKKVE<br>PKSCDKTHTCPPCPAPELLGGPSVFLFPPKPKDTLMISRTPEVTCVVVDVSHEDPE<br>VKFNWYVDGVEVHNAKTKPREEQYQSTYRVVSVLTVLHQDWLNGKEYKCKVS<br>NKALPAPIEKTISKAKGQPREPQVYTLPPSREEMTKNQVSLTCLVKGFYPSDIAVE<br>WESNGQPENNYKTTPPVLDSDGSFFLYSKLTVDKSRWQQGNVFSCSVMHEALH<br>NHYTQKSLSLSPGK<br><br>SEQ ID. NO: 16. (Met HC_(AB2133a Fab + 7.8_B CH3 with N297Q))<br>EVQLVESGGGLVQPGGSLRLSCAASGYTFTSYWLHWVRKAPGKGLEWVGMIDP<br>SNSDTRFNPEFKDRFTISADTSKNTAYLQMNSLRAEDTAVYYCATYRSYVTPLDY<br>WGQGTLVTVSSASTKGPSVFPLAPSSKSTSGGTAALGCLVKDYFPEPVTVSWNSG<br>ALTSGVATGPAVLQSSGLYSLSSVVTVPSSSLGTQTYICNVNHKPSNTKVDKKVE<br>PKSCDKTHTCPPCPAPELLGGPSVFLFPPKPKDTLMISRTPEVTCVVVDVSHEDPE<br>VKFNWYVDGVEVHNAKTKPREEQYQSTYRVVSVLTVLHQDWLNGKEYKCKVS<br>NKALPAPIEKTISKAKGQPREPQVYTLPPSREEMTKNQVSLVCLVKGFYPSDIAVE<br>WESNGQPENNYKTTPPVLDSDGSFFLYSVLTVDKSRWQQGNVFSCSVMHEALH<br>NHYTQKSLSLSPGK<br><br>SEQ ID. NO: 17. (Met HC_(AB2133a Fab + 7.8.60_B CH3 with N297Q))<br>EVQLVESGGGLVQPGGSLRLSCAASGYTFTSYWLHWVRKAPGKGLEWVGMIDP<br>SNSDTRFNPEFKDRFTISADTSKNTAYLQMNSLRAEDTAVYYCATYRSYVTPLDY<br>WGQGTLVTVSSASTKGPSVFPLAPSSKSTSGGTAALGCLVKDYFPEPVTVSWNSG<br>ALTSGVATGPAVLQSSGLYSLSSVVTVPSSSLGTQTYICNVNHKPSNTKVDKKVE<br>PKSCDKTHTCPPCPAPELLGGPSVFLFPPKPKDTLMISRTPEVTCVVVDVSHEDPE<br>VKFNWYVDGVEVHNAKTKPREEQYQSTYRVVSVLTVLHQDWLNGKEYKCKVS |

NKALPAPIEKTISKAKGQPRRPVYTLPPSREEMTKNQVSLVCLVKGFYPSDIAVE
WESNGQPENNYKTTPPVLDSDGSFFLYSVLTVDKSRWQQGNVFSCSVMHEALH
NHYTQKSLSLSPGK

SEQ ID. NO: 18. (Met HC (AB2133a Fab + 20.8_A CH3 with N297Q))
EVQLVESGGGLVQPGGSLRLSCAASGYTFTSYWLHWVRKAPGKGLEWVGMIDP
SNSDTRFNPEFKDRFTISADTSKNTAYLQMNSLRAEDTAVYYCATYRSYVTPLDY
WGQGTLVTVSSASTKGPSVFPLAPSSKSTSGGTAALGCLVKDYFPEPVTVSWNSG
ALTSGVATGPAVLQSSGLYSLSSVVTVPSSSLGTQTYICNVNHKPSNTKVDKKVE
PKSCDKTHTCPPCPAPELLGGPSVFLFPPKPKDTLMISRTPEVTCVVVDVSHEDPE
VKFNWYVDGVEVHNAKTKPREEQYQSTYRVVSVLTVLHQDWLNGKEYKCKVS
NKALPAPIEKTISKAKGQPREPQVSTLPPSREEMTKNQVSLVCLVYGFYPSDIAVE
WESNGQPENNYKTTPPVLDSDGSFFLYSVLTVDKSRWQQGNVFSCSVMHEALH
NHYTQKSLSLSPGK SEQ ID. NO: 19. (Met HC (AB2133a Fab + 20.8.26_A, 20.8.34_A or
20.8.37_A CH3 with N297Q))
EVQLVESGGGLVQPGGSLRLSCAASGYTFTSYWLHWVRKAPGKGLEWVGMIDP
SNSDTRFNPEFKDRFTISADTSKNTAYLQMNSLRAEDTAVYYCATYRSYVTPLDY
WGQGTLVTVSSASTKGPSVFPLAPSSKSTSGGTAALGCLVKDYFPEPVTVSWNSG
ALTSGVATGPAVLQSSGLYSLSSVVTVPSSSLGTQTYICNVNHKPSNIKVDKICVE
PKSCDKTHTCPPCPAPELLGGPSVFLFPPKPKDTLMISRTPEVTCVVVDVSHEDPE
VKFNWYVDGVEVHNAKTKPREEQYQSTYRVVSVLTVLHQDWLNGKEYKCKVS
NKALPAPIEKTISKAKGQPREPQVSTLPPSREEMTKNQVSLMCLVYGFYPSDIAVE
WESNGQPENNYKTTPPVLDSDGSFFLYSVLTVDKSRWQQGNVFSCSVMHEALH
NHYTQKSLSLSPGK SEQ ID. NO: 20. (Met LC (AB2133 Fab))
RIQMTQSPSSLSASVGDRVTITCKSSQSLLYTSSQKNYLAWYQDKPGKAPKLLIY
WASTRESGVPSRFSGSGSGTDFTLTISSLQPEDFATYYCQQYYAYPWTFGQGTKV
EIKGQPKAAPSVTLFPPSSEELQANKATLVCYISDFYPGAVTVAWKADSSPVKAG
VETTTPSKQSNNKYAAWSYLSLTPEQWKSHRSYSCQVTHEGSTVEKTVAPTEC SEQ ID. NO: 21. (BHA10 HC (H4WT + DR_CS Fab + WT CH3))
QVQLVQSGAEVKKPGSSVKVSCKASGYTFTTYYLHWVRYAPGQGLEWMGWIY
PGNVHAQYNEKFKGRVTITADKSTSTAYMELSSLRSEDTAVYYCARSWEGFPYW
GRGTTVTVSSASTKGPSVFPLAPCSKSTSGGTAALGCLVKDYFPEPVTVSWNSGA
LTSGVHTFPAVLQSSGLYSLSSVVTVPSSSLGTQTYICNVNHKPSNTKVDKKVEP
DSGDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSN
KALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNH
YTQKSLSLSPGK SEQ ID. NO:22. (BHA10 HC (H4WT +DR_CS Fab + 7.8_B CH3))
QVQLVQSGAEVKKPGSSVKVSCKASGYTFTTYYLHWVRYAPGQGLEWMGWIY
PGNVHAQYNEKFKGRVTITADKSTSTAYMELSSLRSEDTAVYYCARSWEGFPYW
GRGTTVTVSSASTKGPSVFPLAPCSKSTSGGTAALGCLVKDYFPEPVTVSWNSGA
LTSGVHTFPAVLQSSGLYSLSSVVTVPSSSLGTQTYICNVNHKPSNTKVDKKVEP
DSGDKTHTCPPCPAPELLGGPSVFLFPPKTKDTLMISRTPEVTGVVVDVSHEDPEV
KFNWYVDGVEVHNAKTKPREEQYNSTYRVVSVLTVLHQDWLNGKEYKCKVSN
KALPAPIEKTISKAKGQPREPQVYTLPPSREEMTKNQVSLVCLVKGFYPSDIAVE
WESNGQPENNYKTTPPVLDSDGSFFLYSVLTVDKSRWQQGNVFSCSVMHEALH
NHYTQKSLSLSPGK SEQ ID. NO: 23. (BHA10HC (H4WT + DR_CS Fab + 7.8.60_B CH3))
QVQLVQSGAEVKKPGSSVKVSCKASGYTFTTYYLHWVRYAPGQGLEWMGWIY
PGNVHAQYNEKFKGRVTITADKSTSTAYMELSSLRSEDTAVYYCARSWEGFPYW
GRGTTVTVSSASTKGPSVFPLAPCSKSTSGGTAALGCLVKDYFPEPVTVSWNSGA
LTSGVHTFPAVLQSSGLYSLSSVVTVPSSSLGTQTYICNVNHKPSNTKVDKKVEP
DSGDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSN
KALPAPIEKTISKAKGQPRRPVYTLPPSREENYTKNQVSLVCLVKGFYPSDIAVE
WESNGQPENNYKTTPPVLDSDGSFFLYSVLTVDKSRWQQGNVFSCSVMHEALH
NHYTQKSLSLSPGK SEQ ID. NO: 24. (BHA10 HC (H4WT + DRCS Fab + 20.8_B or 20.8.26_B CH3))
QVQLVQSGAEVKKPGSSVKVSCKASGYTFTTYYLHWVRYAPGQGLEWMGWIY
PGNVHAQYNEKFKGRVTITADKSTSTAYMELSSLRSEDTAVYYCARSWEGFPYW
GRGTTVTVSSASTKGPSVFPLAPCSKSTSGGTAALGCLVKDYFPEPVTVSWNSGA
LTSGVHTFPAVLQSSGLYSLSSVVTVPSSSLGTQTYICNVNHKPSNTKVDKKVEP
DSGDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWENGKEYKCKVSN
KALPAPIEKTISKAKGQPREPQVYTLPPSREDMTKNQVQLTCLVKGFYPSDIAVE
WESNGQPENNYKTTPPVLDSDGSFFLASKLTVDKSRWQQGNVFSCSVMHEALH
NHYTQKSLSLSPGK -continued

| Sequences |
|---|
| SEQ ID. NO: 25. (BHA10 HC (H4WT + DR_CS Fab + 20.8.34_B CH3))<br>QVQLVQSGAEVKKPGSSVKVSCKASGYTFTTYYLHWVRYAPGQGLEWMGWIY<br>PGNVHAQYNEKFKGRVTITADKSTSTAYMELSSLRSEDTAVYYCARSWEGFPYW<br>GRGTTVTVSSASTKGPSVFPLAPCSKSTSGGTAALGCLVKDYFPEPVTVSWNSGA<br>LTSGVHTFPAVLQSSGLYSLSSVVTVPSSSLGTQTYICNVNHKPSNTKVDKKVEP<br>DSGDKTHTCPPCPAPELLGGPSVFLFPPKPKDTLMISRTPEVTCVVVDVSHEDPEV<br>KFNWYVDGVEVHNAKTKPREEQYNSTYRVVSVLTVLHQDWLNGKEYKCKVSN<br>KALPAPIEKTISKAKGQPREPQVYTLPPSRGDMTKNQVQLTCLVKGFYPSDIAVE<br>WESNGQPENNYKTTPPVLDSDGSFFLASKLTVDKSRWQQGNVFSCSVMHEALH<br>NHYTQKSLSLSPGK |
| SEQ ID. NO: 26. (BHA10 HC (H4WT + DR_CS Fab + 20.8.37_B CH3))<br>QVQLVQSGAEVKKPGSSVKVSCKASGYTFTTYYLHWVRYAPGQGLEWMGWIY<br>PGNVHAQYNEKFKGRVTITADKSTSTAYMELSSLRSEDTAVYYCARSWEGFPYW<br>GRGTTVTVSSASTKGPSVFPLAPCSKSTSGGTAALGCLVKDYFPEPVTVSWNSGA<br>LTSGVHTFPAVLQSSGLYSLSSVVTVPSSSLGTQTYICNVNHKPSNTKVDKKVEP<br>DSGDKTHTCPPCPAPELLGGPSVFLFPPKPKDTLMISRTPEVTCVVVDVSHEDPEV<br>KFNWYVDGVEVHNAKTKPREEQYNSTYRVVSVLTVLHQDWLNGKEYKCKVSN<br>KALPAPIEKTISKAKGQPREPQVYTLPPSREDMTKNQVRLTCLVKGFYPSDIAVE<br>WESNGQPENNYKTTPPVLDSDGSFFLASKLTVDKSRWQQGNVFSCSVMHEALH<br>NHYTQKSLSLSPGK |
| SEQ ID. NO: 27. (BHA10 LC (H4WT + DR_CS Fab))<br>DIQMTQSPSSLSASVGDRVTITCKASQNVGINVAWYQRKPGDAPKSLISSASYRY<br>SGVPSRFSGSGSGTDFTLTISSLQPEDFATYFCQQYDTYPFTFGQGTKVEIKRTVA<br>APSVFIFPPSKEQLKSGTASVVCLLNNFYPREAKVQWKVDNALQSGNSQESVEEQ<br>DSKDSTYSLSSTLTLSKADYEKHKVYACEVTHQGLSSPVTKSFNRGEC |
| SEQ ID. NO: 28. (Matuzumab HC (H4WT + DR_CS Fab + WT CH3))<br>QVQLVQSGAEVKKPGASVKVSCKASGYTFTSHWMHWVRYAPGQGLEWIGEFN<br>PSNGRTNYNEKFKSKATMTVDTSTNTAYMELSSLRSEDTAVYYCASRDYDYDG<br>RYFDYWGRGTLVTVSSASTKGPSVFPLAPCSKSTSGGTAALGCLVKDYFPEPVTV<br>SWNSGALTSGVHTFPAVLQSSGLYSLSSVVTVPSSSLGTQTYICNVNHKPSNTKV<br>DKKVEPDSGDKTHTCPPCPAPELLGGPSVFLFPPKPKDTLMISRTPEVTCVVVDVS<br>HEDPEVKFNWYVDGVEVHNAKTKPREEQYNSTYRVVWSVLTVLHQDWLNGKEY<br>KCKVSNKALPAPIEKTISKAKGQPREPQVYTLPPSREEMTKNQVSLTCLVKGFYPS<br>DIAVEWESNGQPENNYKTTPPVLDSDGSFFLYSKLTVDKSRWQQGNVFSCSVMH<br>EALHNHYTQKSLSLSPGK |
| SEQ ID. NO: 29. (Matuzumab HC (H4WT + DR_CS Fab + 7.8_A CH3))<br>QVQLVQSGAEVKKKGASVKVSCKASGYTFTSHWMHWVRYAPGQGLEWIGEFN<br>PSNGRTNYNEKFKSKATMTVDTSTNTAYMELSSLRSEDTAVYYCASRDYDYDG<br>RYFDYWGRGTLVTVSSASTKGPSVFPLAPCSKSTSGGTAALGCLVKDYFPEPVTV<br>SWNSGALTSGVHTFPAVLQSSGLYSLSSVVTVPSSSLGTQTYICNVNHKPSNTKV<br>DKKVEPDSGDKTHTCPPCPAPELLGGPSVFLFPPKPKDTLMISRTPEVTCVVVDVS<br>HEDPEVKFNWYVDGVEVHNAKTKPREEQYNSTYRVVSVLTVLHQDWLNGKEY<br>KCKVSNKALPAPIEKTISKAKGQPREPQVYTLPPSREEMTKNQVSLTCLVKGFYPS<br>DIAVEWESNGQPENNYKTTPPVLMSDGSFFLASKLTVDKSRWQQGNVFSCSVM<br>HEALHNHYTQKSLSLSPGK |
| SEQ ID. NO: 30. (Matuzumab HC (H4WT + DR_CS Fab + 7.8_B CH3))<br>QVQLVQSGAEVKKPGASVKVSCKASGYTFTSHWMHWVRYAPGQGLEWIGEFN<br>PSNGRTNYNEKFKSKATMTVDTSTNTAYMELSSLRSEDTAVYYCASRDYDYDG<br>RYFDYWGRGTLVTVSSASITCGPSVFPLAPCSKSTSGGTAALGCLVKDYFPEPVTV<br>SWNSGALTSGVHTFPAVLQSSGLYSLSSVVTVPSSSLGTQTYICNVNHKPSNTKV<br>DKKVEPDSGDKTHTCPPCPAPELLGGPSVFLFPPKPKDTLMISRTPEVTCVVVDVS<br>HEDPEVKFNWYVDGVEVHNAKTKPREEQYNSTYRWSVLTVLHQDWLNGKEY<br>KCKVSNKALPAPIEKTISKAKGQPREPQVYTLPPSREEMTKNQVSLVCLVKGFYP<br>SDIAVEWESNGQPENNYKTTPPVLDSDGSFFLYSVLTVDKSRWQQGNVFSCSVM<br>HEALHNHYTQKSLSLSPGK |
| SEQ ID. NO: 31. (Matuzumab HC (H4WT + DR_CS Fab + 7.8.60_A CH3))<br>QVQLVQSGAEVKKPGASVKVSCKASGYTFTSHWMHWVRYAPGQGLEWIGEFN<br>PSNGRTNYNEKFKSKATMTVDTSTNTAYMELSSLRSEDTAVYYCASRDYDYDG<br>RYFDYWGRGTLVTVSSASTKGPSVFPLAPCSKSTSGGTAALGCLVKDYFPEPVTV<br>SWNSGALTSGVHTFPAVLQSSGLYSLSSVVTVPSSSLGTQTYICKVNHKPSNTKV<br>DKKVEPDSGDKTHTCPPCPAPELLGGPSVFLFPPKPKDTLMISRTPEVTCVVVDVS<br>HEDPEVKFNWYVDGVEVHNAKTKPREEQYNSTYRVVSVLTVLHQDWLNGKEY<br>KCKVSNKALPAPIEKTISKAKGQPREPQVYTLPPSREEMTDNQVSLTCLVKGFYPS<br>DIAVEWESNGQPENNYKTTPPVLMSDGSFFLASKLTVDKSRWQQGNVFSCSVM<br>HEALHNHYTQKSLSLSPGK |
| SEQ ID. NO: 32. (Matuzumab HC (H4WT + DR_CS Fab + 7.8.60_B CH3))<br>QVQLVQSGAEVKPGASVKVSCKASGYTFTSHWMHWVRYAPGQGLEWIGEFN<br>PSNGRTNYNEKFKSKATMTVDTSTNTAYMELSSLRRSEDTAVYYCASRDYDYDG<br>RYFDYWGRGTLVTVSSASTKGPSVFPLAPCSKSTSGGTAALGCLVKDYFPEPVTV<br>SWNSGALTSGVHTFPAVLQSSGLYSLSSVVTVPSSSEGTQTYICNVNHKPSNTKV |

-continued

Sequences

```
DKKVEPDSGDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEY
KCKVSNKALPAPIEKTISKAKGQPRRPRVYTLPPSREEMTKNQVSLVCLVKGFYP
SDIAVEWESNGQPENNYKTTPPVLDSDGSFFLYSVLTVDKSRWQQGNVFSCSVM
HEALHNHYTQKSLSLSPGK

SEQ ID. NO: 33. (Matuzumab HC (H4WT + DR_CS Fab + 20.8_B or
20.8.26_B CH3))
QVQLVQSGAEVKKPGASVKVSCKASGYTFTSHWMHWVRYAPGQGLEWIGEFN
PSNGRTNYNEKFKSKATMTVDTSTNTAYMELSSLRSEDTAVYYCASRDYDYDG
RYFDYWGRGTLVTVSSASTKGPSVFPLAPCSKSTSGGTAALGCLVKDYFPEPVTV
SWNSGALTSGVHTFPAVLQSSGLYSLSSVVTVPSSSLGTQTYICNVNHKPSNTKV
DKKVEPDSGDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEY
KCKVSNKALPAPIEKTISKAKGQPREPQVYTLPPSREDMTKNQVQLTCLVKGFYP
SDIAVEWESNGQPENNYKTTPPVLDSDGSFFLASKLTVDKSRWQQGNVFSCSVM
HEALHNHYTQKSLSLSPGK SEQ ID. NO: 34. (Matuzumab HC (H4WT + DR_CS Fab + 20.8.34_B CH3))
QVQLVQSGAEVKKPGASVKVSCKASGYTFTSHWMHWVRYAPGQGLEWIGEFN
PSNGRTNYNEKFKSKATMTVDTSTNTAYMELSSLRSEDTAVYYCASRDYDYDG
RYFDYWGRGTLVTVSSASTKGPSVFPLAPCSKSTSGGTAALGCLVKDYFPEPVTV
SWNSGALTSGVHTFPAVLQSSGLYSLSSVVTVPSSSLGTQTYICNVNHKPSNTKV
DKKVFPDSGDKTHTCPPCPAPELLGGPSVFLFPPKPKDTLMISRTPEVTCVVVDVS
HEDPEVKFNWYVDGVEVHNAKTKPREHQYNSTYRVVSVLTVLHQDWLNGKEY
KCKVSNKALPAPIEKTISKAKGQPREPQVYTLPPSRGDMTKNQVQLTCLVKGFYP
SDIAVEWESNGQPENNTKTTPPVLDSDGSFFLASKLTVDKSRWQQGNVFSCSVM
HEALHNHYTQKSLSLSPGK SEQ ID. NO: 35. (Matuzumab HC (H4WT + DR_CS Fab + 20.8.37_B CH3))
QVQLVQSGAEVKKPGASVKVSCKASGYTFTSHWMHWVRYAPGQGLEWIGEFN
PSNGRTNYNEKFKSKATMTVDTSTNTAYMELSSLRSEDTAVYYCASRDYDYDG
RYFDYWGRGTLVTVSSASTKGPSVFPLAPCSKSTSGGTAALGCLVKDYFPEPVTV
SWNSGALTSGVHTFPAVLQSSGLYSLSSVVTVPSSSLGTQTYICNVNHKPSNTKV
DKKVFPDSGDKTHTCPPCPAPELLGGPSVFLFPPKPKDTLMISRTPEVTCVVVDVS
HEDPEVKFNWYVDGVEVHNAKTKPREHQYNSTYRVVSVLTVLHQDWLNGKEY
KCKVSNKALPAPIEKTISKAKGQPREPQVYTLPPSREDMTKNQVRLTCLVKGFYP
SDIAVEWESNGQPENNTKTTPPVLDSDGSFFLASKLTVDKSRWQQGNVFSCSVM
HEALHNHYTQKSLSLSPGK SEQ ID. NO: 36. (Matuzumab LC (H4WT + DR_CS Fab))
DIQMTQSPSSLSASVGDRVTITCSASSSVTYMYWYQRKPGDAPKLLIYDTSNLAS
GVPSRFSGSGSGTDYTFTISSLQPEDIATYYCQQWSSHIFTGQGTKVEIKRTVAAP
SVFIFPPSKEQLKSGTASVVCLLNNFYPREAKVQWKVDNALQSGNSQESVTEQDS
KDSTYSLSSTLTLSKADYEKHKVYACEVTHQGLSSPVTKSFNRGEC Fc Domain (CH2-CH3) Sequences
SEQ ID NO: 37. Human IgG1 Fc_(WT)
APELLGGPSVFLFPPKPKDTLMISRTPEVTCVVVDVSHEDPEVKFNWYVDGVEVH
NAKTKPREEQYNSTYRWSVLTVLHQDWLNGKEYKCKVSNKALPAPIEKTISKA
KGQPREPQVYTLPPSREEMTKNQVSLTCLVKGFYPSDIAVEWESNGQPENNYKT
TPPVLDSDGSTFLYSKLTVDKSRWQQGNVFSCSVMHEALHNHYTQKSLSLSPGK SEQ ID NO: 38. Human IgG1 Fc_(7.8_A CH3)
APELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKA
KGQPREPQVYTLPPSREEMTKNQVSLTCLVKGFYPSDIAVEWESNGQPENNYKT
TPPVLMSDGSFFLASKLTVDKSRWQQGNVFSCSVMHEALHNHYTQKSLSLSPGK SEQ ID NO: 39. Human IgG1 Fc_(7.8.60_A CH3)
APELLGGPSVFLFPPKPKDTLMISRTPEVTCVVVDVSHEDPEVKFNWYNTDGVEVH
NAKTKPREEQYNSTYRWSVLTVLHQDWLNGKEYKCKVSNKALPAPIEKTISKA
KGQPREPQVYTLPPSREEMTDNQVSLTCLVKGFYPSDIAVEWESNGQPENNYKT
TPPVLMSDGSFFLASKLTVDKSRWQQGNVFSCSVMHEALHNHYTQKSLSLSPGK SEQ ID NO: 40. Human IgG1 Fc_(20.8_A, 20.8.31_A or 20.8.33_A CH3)
APELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKA
KGQPREPQVSTLPPSREEMTKNQVSLVCLVYGFYPSDIAVEWESNGQPENNYKTT
PPVLDSDGSFFLYSVLTVDKSRWQQGNVFSCSVMHEALHNHYTQKSLSISPGK SEQ ID NO: 41. Human IgG1 Fc_(20.8.26_A, 20.8.34_A or 20.8.37_A CH3)
APELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKA
KGQPREPQVSTLPPSREEMTKNQVSLMCLVYGFYPSDIAVEWESNGQPENNYKT
TPPVLDSDGSFFLYSVLTVDKSRWQQGNVFSCSVMHEALHNHYTQKSLSLSPGK
```

| Sequences |
|---|
| SEQ ID NO: 42. Human IgG1 Fc_(7.8_B or 7.4_B CH3)<br>APELLGGPSVFLFPPKPKDTLMISRTPEVTCVVVDVSHEDPEVKFNWYVDGVEVH<br>NAKTKPREEQYNSTYRWSVLTVLHQDWLNGKEYKCKVSNKALPAPIEKTISKA<br>KGQPREPQVYTLTSREEMTKNQVSLVCLCKGFYPSDIAVEWESNGQPENNYKT<br>TPPVLDSDGSFFLYSVLTVDKSRWQQGNVFSCSVMHEALHNHYTQKSLSLSPGK<br><br>SEQ ID NO: 43. Human IgG1 Fc_(7.8.60_B CH3)<br>APELLGGPSVFLFPPKPKDTLMISRTPEVTCVVVDVSHEDPEVKFNWYVDGVEVE<br>NAKTKPREEQYNSTYRVVSVLTVLHQDWLNGKEYKCKVSNKALPAPIEKTISKA<br>KGQPRRPRVYTLPPSREEMTKNQVSLVCLVKGFYPSDIAVEWESNGQPENNYKT<br>TPPVLDSDGSFFLYSVLTVDKSRWQQGNVFSCSVMHEALHNHYTQKSLSLSPGK<br><br>SEQ ID NO: 44. Human IgG1 Fc_(20.8_B or 20.8.26_B CH3)<br>APELLGGPSVFLFPPKPKDTLMISRTPEVTCVVVDVSHEDPEVKFNWYVDGVEVH<br>NAKTKPREEQYNSTYRVVSVLTVLHQDWLNGKEYKCKVSNKALPAPIEKTISKA<br>KGQPREPQVYTLPPSREDMTKNQVQLTCLVKGFYRSDIAVEWESNGQPENNYKT<br>TPPVLDSDGSFFLASKLTVDKSRWQQGNVFSCSVMHEALHNHYTQKSLSLSPGK<br><br>SEQ ID NO: 45. Human IgG1 Fc_(20.8.33_B or 20.8.34_B CH3)<br>APELLGGPSVFLFPPKPKDTLMISRTPEVTCVVVDVSHEDPEVKFNWYVDGVEVH<br>NAKTKPREEQYNSTYRVVSVLTVLHQDWLNGKEYKCKVSNKALPAPIEKTISKA<br>KGQPREPQVYTLPSRGDMTKNQVQLTCLVKGFYPSDIAVEWESNGQPENNYKT<br>TPPVLDSDGSFFLASKLTVDKSRWQQGNVFSCSVMHEALHNHYTQKSLSLSPGK<br><br>SEQ ID NO: 46. Human IgG1 Fc_(20.8.31_B or 20.8.37_B CH3)<br>APELLGGPSVFLFPPKPKDTLMISRTPEVTCVVVDVSHEDPEVKFNWYVDGVEVH<br>NAKTKPREEQYNSTYRVVSVLTVLHQDWLNGKEYKCKVSNKALPAPIEKTISKA<br>KGQPREPQVYTLPPSREDMTKNQVRLTCLVKGFYPSDIAVEWESNGQPENNYKT<br>TPPVLDSDGSFFLASKLTVDKSRWQQGNVFSCSVMHEALHNHYTQKSLSLSPGK<br><br>SEQ ID NO: 47. (Pertuzumab IgG4 HC (AB2133a Fab + 7.8.60_A CH3 with<br>241P (Kabat Numbering), 234A, 235A, 297Q mutations (EU Index Numbering))<br>EVQLVESGGGLVQPGGSLRLSCAASGFTFTDYTMDWVRKAPGKGLEWVADVNP<br>NSGGSIYNQEFKGRFTLSVDRSKNTLYLQMNSLRAEDTAVYYCARNLGPSFYFD<br>YWGQGTLVTVSSASTKGPSVFPLAPCSRSTSESTAALGCLVKDYFPEPVTVSWNS<br>GALTSGVATGPAVLQSSGLYSLSSVVTVPSSSLGTKTYTCNVDKKPSNTKVDKR<br>VESKYGPPCPPPCPAPEAAGGPSVFLFPPKPKDTLMISRTPEVTCVVVDVSQEDPEV<br>QFNWYVDGVEVHNAKTKPREEQFQSTYRVVSVLTVLHQDWLNGKEYKCKVSN<br>KGLPSSIEKTISKAKGQPREPQVYTLPPSQEEMTDNQVSLTCLVKGFYPSDIAVEW<br>ESNGQPENNYKTTPPVLMSDGSFFLASRLTVDKSRWQEGNVFSCSVMHEALHNH<br>YTQKSLSLSLG<br><br>SEQ ID NO: 48. (Pertuzumab IgG4 HC (AB2133a Fab + 20.8.34_A CH3 with<br>241P (Kabat Numbering), 234A, 235A, 297Q mutations (EU Index Numbering))<br>EVQLVESGGGLVQPGGSLRLSCAASGFTFTDYTMDWVRKAPGKGLEWVADVNP<br>NSGGSIYNQEFKGRFTLSYDRSKNTLYLQMNSLRAEDTAVYYCARNLGPSFYFD<br>YWGQGTLVTVSSASTKGPSVFPLAPCSRSTSESTAALGCLVKDYFPEPVTVSWNS<br>GALTSGVATGPAVLQSSGLYSLSSVVTVPSSSLGTKTYTCNVDHKPSNTKVDKR<br>VESKYGPPCPPPCPAPEAAGGPSVFLFPPKPKDTLMISRTPEVTFCVVVDVSQEDPEV<br>QFNWYVDGVEVHNAKTKPREEQFQSTYRVVSVLTVLHQDWLNGKEYKCKVSN<br>KGLPSSIEKTISKAKGQPREPQVSTLPPSQEEMTKNQVSLMCLVYGFYPSDIAVEW<br>ESNGQPENNYKTTPPVLDSDGSFFLYSVLTVDKSRWQEGNVFSCSVMHEALHNH<br>YTQKSLSLSLG<br><br>SEQ ID NO: 49. (Pertuzumab LC (2133a Fab))<br>RIQMTQSPSSLSASVGDRVTITCKASQDVSIGVAWYQDKPGKAPKLLIYSASYRY<br>TGVPSRFSGSGSGTDFTLTISSLQPEDFATYYCQQYYTYPYTFGQGTKVEIKGQPK<br>AAPSVTLFPPSSEELQANKATLVCYISDFYPGAVTVAWKADSSPVKAGVETTTPS<br>KQSNNKYAAWSYLSLTPEQWKSHRSYSCQVTHEGSTVEKTVAPTEC<br><br>SEQ ID NO: 50. (MetMAb IgG4 HC (AB2133a Fab + 7.8.60_A CH3 with<br>241P (Kabat Numbering), 234A, 235A, 297Q mutations (EU Index Numbering))<br>EVQLVESGGGLVQPGGSLRLSCAASGYTFTSYWLHWVRKAPGKGLEWVGMIDP<br>SNSDTRFNPEFKDRFTISADTSKNTAYLQMNSIRAEDTAVYYCATYRSYVTPLDY<br>WGQGTLVTVSSASTKGPSVFPLAPCSRSTSESTAALGCLVKDYFPEPVTVSWNSG<br>ALTSGVATGPAVLQSSGLYSLSSVVTVPSSSLGTKTYTCNVDHKPSNTKVDKRVE<br>SKYGPPCPPCPAPEAAGGPSVFLFPPKPKDTLMISRTPEVTCVVVDVSQEDPEVQF<br>NWYVDGVEVHNAKTKPREEQFQSTYRVVSVLTVLHQDWLNGKEYKCKVSNKG<br>LPSSIEKTISKAKGQPREPQVYTLPPSQEEMTDNQVSLTCLVKGFYPSDIAVEWES<br>NGQPENNYKTTPPVLMSDGSFFLASRLTVDKSRWQEGNVFSCSVMHEALHNHY<br>TQKSLSLSLG<br><br>SEQ ID NO: 51. (MetMAb IgG4 HC (AB2133a Fab + 20.8.34_A CH3 with<br>241P (Kabat Numbering), 234A, 235A, 297Q mutations (EU Index Numbering))<br>EVQLVESGGGLVQPGGSLRLSCAASGYTFTSYWLHWVRKAPGKGLEWVGMIDP<br>SNSDTRFNPEFKDRFTISADTSKNTAYLQMNSIRAEDTAVYYCATYRSYVTPLDY<br>WGQGTLVTVSSASTKGPSVFPLAPCSRSTSESTAALGCLVKDYFPEPVTVSWNSG |

```
ALTSGVATGPAVLQSSGLYSLSSVVTVPSSSLGTKTYTCNVDHKPSNTKVDKRVE
SKYGPPCPPCPAPEAAGGPSVFLFPPKPKDTLMISRTPEVTCVVVDVSQEDPEVQF
NWYVDGVEVHNAKTKPREEQFQSTYRVVSVLTVLHQDWLNGKEYKCKVSNKG
LPSSIEKTISKAKGQPREPQVSTLPPSQEEMTKNQVSLMCLVYGFYPSDIAVEWES
NGQPENNYKTTPPVLDSDGSFFLYSVLTVDKSRWQEGNVFSCSVMHEALHNHYT
QKSLSLSLG

SEQ ID NO: 52. (MetMAb LC (AB2133a Fab))
RIQMTQSPSSLSASVGDRVTITCKSSQSLLYTSSQKNYLAWYQDKPGKAPKLLIY
WASTRESGVPSRFSGSGSGTDFTLTISSLQPEDFATYYCQQYYAYPWTFGQGTKV
EIKGQPKAAPSVTLFPPSSEELQANKATLVCYISDFYPGAVTVAWKADSSPVKAG
VETTTPSKQSNNKYAAWSYLSLTPEQWKSHRSYSCQVTHEGSTVEKTVAPTEC

SEQ ID NO: 53. (Matuzumab IgG4 HC (H4WT (Fab + 7.8.60_B CH3 with
241P (Kabat Numbering), 234A, 235A, 297Q mutations (EU Index Numbering))
QVQLVQSGAEVKKPGASVKVSCKASGYTFTSHWMHWVRYAPGQGLEWIGEFN
PSNGRTNYNEKFKSKATMTVDTSTNTAYMELSSLRSEDTAVYYCASRDYDYDG
RYFDYWGRGTLVTVSSASTKGPSVFPLAPCSRSTSESTAALGCLVKDYFPEPVTV
SWNSGALTSGVHTFPAVLQSSGLYSLSSVVTVPSSSLGTKTYTCNVDHKPSNTKV
DKRVESDYGPPCPPCPAPEAAGGPSVFLFPPKPKDTLMISRTPEVTCVVVDVSQE
DPEVQFNWYVDGVEVHNAKTKPREEQFQSTYRVVSVLTVLHQDWLNGKEYKC
KVSNKGLPSSIEKTISKAKGQPRRPRVYTLPPSQEEMTKNQVSLVCLVKGFYPSDI
AVEWESNGQPENNYKTTPPVLDSDGSFFLYSVLTVDKSRWQEGNVFSCSVMHEA
LHNHYTQKSLSLSLG SEQ ID NO: 54. (Matuzumab IgG4 HC (H4WT(Fab + 20.8.34_B CH3 with
241P (Kabat Numbering), 234A, 235A, 297Q mutations (EU Index Numbering))
QVQLVQSGAEVKKPGASVKVSCKASGYTFTSHWMHWVRYAPGQGLEWIGEFN
PSNGRTNYNEKFKSKATMTVDTSTWAYMELSSLRSEDTAVYYCASRDYDYDG
RYFDYWGRGTLVTVSSASTKGPSVFPLAPCSRSTSESTAALGCLVKDYFPEPVTV
SWNSGALTSGVHTFPAVLQSSGLYSLSSVVTVPSSSLGTKTYTCNVDHKPSNTKV
DKRVESDYGPPCPPCPAPEAAGGPSVFLFPPKPKDTLMISRTPEVTCVVVDVSQE
DPEVQFNWYVDGVEVHNAKTKPREEQEQSTYRVVSVLTVLHQDWLNGKEYKC
KVSNKGLPSSIEKTISKAKGQPREPQVYTLPPSQGDMTKNQVQLTCLVKGFYPSD
IAVEWESNGQPENNYKTTPPVLDSDGSFFLASRLTVDKSRWQEGNVFSCSVMHE
ALHNHYTQKSLSLSLG SEQ ID NO: 55. (Matuzumab LC (H4WT(+DR_CS)Fab))
DIQMTQSPSSLSASVGDRVTITCSASSSVTYMWYQRKPGDAPKLLIYDTSNLAS
GVPSRFSGSGSGTDYTFTISSLQPEDIATYYCQQWSSHIFTGQGTKVEIKRTVAAP
SVFIFPPSKEQLKSGTASVVCLLNNFYPREAKVQWKVDNALQSGNSQESVTEQDS
KDSTYSLSSTLTLSKADYEKHKVYACEVTHQGLSSPVTKSFNRGEC SEQ ID NO: 56. (BHA10 IgG4 HC (H4WT(Fab + 7.8.60_B CH3 with 241P
(Kabat Numbering), 234A, 235A, 297Q mutations (EU Index Numbering))
QVQLVQSGAEVKKPGSSVKVSCKASGYTFTTYYLHWVRYAPGQGLEWMGWIY
PGNVHAQYNEKFKGRVTITADKSTSTAYMELSSLRSEDTAVYYCARSWEGFPYW
GRGTTVTVSSASTKGPSVFPLAPCSRSTSESTAALGCLVKDYFPEPVTVSWNSGA
LTSGVHTFPAVLQSSGLYSLSSVVTVPSSSLGTKTYTCNVDHKPSNTKVDKRVES
DYGPPCPPCPAPEAAGGPSVELFPPKPKDTLMISRTPEVTCVVVDVSQEDPEVQFN
WYVDGVEVHNAKTKPREEQFQSTYRVVSVLTVLHQDWLNGKEYKCKVSNKGL
PSSIEKTISKAKGQPRRPRVYTLPPSQEEMTKNQVSLVCLVKGFYPSDIAVEWESN
GQPENNYKTTPPVLDSDGSFFLYSVLTVDKSRWQEGNVFSCSVMHEALHNHYTQ
KSLSLSLG SEQ ID NO: 57. (BHA10 IgG4 HC (H4WT(+DR_CS)Fab + 20.8.34_B CH3 with 241P
(Kabat Numbering), 234A, 235A, 297Q mutations (EU Index Numbering))
QVQLVQSGAEVKKPGSSVKVSCKASGYTFTTYYLHWVRYAPGQGLEWMGWIY
PGNVHAQYNEKFKGRVTITADKSTSTAYMELSSLRSEDTAVYYCARSWEGFPYW
GRGTTVTVSSASTKGPSVFPLAPCSRSTSESTAALGCLVKDYFREPVTVSWNSGA
LTSGVHTFPAVLQSSGLYSLSSVVTVPSSSLGTKTYTCNVDHKPSNTKVDKRVES
DYGPPCPPCPAPEAAGGPSVFLFPPKPKDTLMISRTPEVTCVVVDVSQEDPEVQFN
WYVDGVEVHNAKTKPREEQFQSTYRVVSVLTVLHQDWLNGKEYKCKVSNKGL
PSSIEKTISKAKGQPREPQVYTLPPSQGDMTKNQVQLTCLVKGFYPSDIAVEWES
NGQPENNYKTTPPVLDSDGSFFLASRLTVDKSRWQEGNVFSCSVMHEALHNHYT
QKSLSLSLG SEQ ID NO: 58. (BHA10 LC (H4WT(+DR_CS)Fab))
DIQMTQSPSSLSASVGDRVTITCKASQNVGINVAWYQRKPGDAPKSLISSASYRY
SGVPSRFSGSGSGTDFTLTISSLQPEDFATYFCQQYDTYPFTFGQGTKVEIKRTVA
APSVFIFPPSKEQLKSGTASVVCLLNNFYPREAKVQWKVDNALQSGNSQESVTEQ
DSKDSTYSLSSTLTLSKADYEKHKVYACEVTHQGLSSPVTKSFNRGEC IgG4 Fc Domain (CH2-CH3) Sequences
SEQ ID NO: 59. Human IgG4 Fc_(WT)
APEFLGGPSVFLFPPKPKDTLMISRTPEVTCVVVDVSQEDPEVQFNWYVDGVEVH
NAKTKPREEQFNSTYRVVSVLTVLHQDWLNGKEYKCKVSNKGEPSSIEKTISKA
```

KGQPREPQVYTLPPSQEEMTKNQVSLTCLVKGFYPSDIAVEWESNGQPENNYKT
TPPVLDSDGSFFLYSRLTVDKSRWQEGNVFSCSVMHEALHNHYTQKSLSLSLGK

SEQ ID NO: 60. Human IgG4 Fc_(7.4_A CH3)
APEFLGGPSVFLFPPKPKDTLMISRTPEVTCVVVDVSQEDPEVQFNWYVDGVEVH
NAKTKPREEQFNSTYRVVSVLTVLHQDWLNGKEYKCKVSNKGLPSSIEKTISKA
KGQPREPQVYTLPPSQEEMTKNQVSLTCLVKGFYPSDIAVEWESNGQPENNYKT
TPPVLDSDGSFFLASRLTVDKSRWQEGNVFSCSVMHEALHNHYTQKSLSLSLGK SEQ ID NO: 61. Human IgG4 Fc_(7.8_A CH3)
APEFLGGPSVFLFPPKPKDTLMISRTPEVTCVVVDVSQEDPEVQFNWYVDGVEVH
NAKTKPREEQFNSTYRVVSVLTVLHQPWLNGKEYKCKVSNKGLPSSIEKTISKA
KGQPREPQVYTLPPSQEEMTKNQVSLTCLVKGFYPSDIAVEWESNGQPENNYKT
TPPVLMSDGSFFLASRLTVDKSRWQEGNVFSCSVMHEALHNHYTQKSLSLSLGK SEQ ID NO: 62. Human IgG4 Fc_(7.8.60_A CH3)
APEFLGGPSVFLFPPKPKDTLMISRTPEVTCVVVDVSQEDPEVQFNWYVDGVEVH
NAKTKPREEQENSTYRVVSVLTVLHQDWLNGKEYKCKVSNKGLPSSIEKTISKA
KGQPREPQVYTLPPSQEEMTDNQVSLTCLVKGFYPSDIAVEWESNGQPENNYKT
TPPVLMSDGSFFLASRLTVDKSRWQEGNVFSCSVMHEALHNHYTQKSLSLSEGK SEQ ID NO: 63. Human IgG4 Fc_(20.8_A, 20.8.31_A or 20.8.33_A CH3)
APEFLGGPSVFLFPPKPKDTLMISRTPEVTCVVVDVSQEDPEVQFNWYVDGVEVH
NAKTKPREEQFNSTYRVVSVLTVLHQDWLNGKEYKCKVSNKGLPSSIEKTISKA
KGQPREPQVSTLPPSQEEMTKNQVSLVCLVYGFYPSDIAVEWESNGQPENNYKT
TPPVLDSDGSFFLYSVLTVDKSRWQEGNVFSCSVMHEALHNHYTQKSLSLSWK SEQ ID NO: 64. Human IgG4 Fc_(20.8.26_A, 20.8.34_A or 20.8.37_A CH3)
APEFLGGPSVFLFPPKPKDTLMISRTPEVTCVVVDVSQEDPEVQFNWYVDGVEVH
NAKTKPREEQFNSTYRVVSVLTVLHQDWLNGKEYKCKVSNKGLPSSIEKTISKA
KGQPREPQVSTLPPSQEEMTKNQVSLMCLVYGFYPSDIAVEWESNGQPENNYKT
TPPVLDSDGSFFLYSVLTVDKSRWQEGNVFSCSVMHEALHNHYTQKSLSLSLGK SEQ ID NO: 65. Human IgG4 Fc_(7.8_B or 7.4_B CH3)
APEFLGGPSVFLFPPKPKDTLMISRTPEVTCVVVDVSQEDPEVQFNWYVDGVEVH
NAKTKPREEQFNSTYRVVSVLTVLHQDWLNGKEYKCKVSNKGLPSSIEKTISKA
KGQPREPQVYTLPPSQEEMTKNQVSLVCLVKGFYPSDIAVEWESNGQPENNYKT
TPPVLDSDGSFFLYSVLTVDKSRWQEGNVFSCSVMHEALHNHYTQKSLSLSLGK SEQ ID NO: 66. Human IgG4 Fc_(7.8.60_B CH3)
APEFLGGPSVFLFPPKPKDTLMISRTPEVTCVVVDVSQEDPEVQFNWYVDGVEVH
NAKTKPREEQFNSTYRVVSVLTVLHQDWLNGKEYKCKVSNKGLPSSIEKTISKA
KGQPRRPRVYTLPPSQEEMTKNQVSLVCLVKGFYPSDIAVEWESNGQPENNYKT
TPPVLDSDGSFFLYSVLTVDKSRWQEGNVFSCSVMHEALHNHYTQKSLSLSWK SEQ ID NO: 67. Human IgG4 Fc_(20.8_B or 20.8.26_B CH3)
APEFLGGPSVFLFPPKPKDTLMISRTPEVTCVVVDVSQEDPEVQFNWYVDGVEVH
NAKTKPREEQFNSTYRVVSVLTVLHQDWLNGKEYKCKVSNKGLPSSIEKTISKA
KGQPREPQVYTLPPSQEDMTKNQVQLTCLVKGFYPSDIAVEWESNGQPENNYKT
TPPVLDSDGSFFLASRLTVDKSRWQEGNVSCSVMHEALHNHYTQKSLSLSWK SEQ ID NO: 68. Human IgG4 Fc_(20.8.33_B or 20.8.34_B CH3)
APEFLGGPSVFLFPPKYKDTLIMISRTPEVTCVVVDVSQEDPEVQFNWYVDGVEVH
NAKTKPREEQFNSTYRVVSVLTVLHQDWLNGKEYKCKVSNKGLPSSIEKTISKA
KGQPREPQVYTLPPSQGDMTKNQVQLTCLVKGFYPSDIAVEWESNGQPENNYKT
TPPVLDSDGSFFLASRLTVDKSRWQEGNVFSCSVMHEALHNHYTQKSLSLSLGK SEQ ID NO: 69. Human IgG4 Fc_(20.8.3_B or 20.8.37_B CH3)
APEFLGGPSVFLFPPKPKDTLMISRTPEVTCVVVDVSQEDPEVQFNWYVDGVEVH
NAKTKPREEQFNSTYRVVSVLTVLHQDWLNGKEYKCKVSNKGLPSSIEKTISKA
KGQPREPQVYTLPPSQEDMTKNQVRLTCLVKGFYPSDIAVEWESNGQPENNYKT
TPPVLDSDGSFFLASRLTVDKSRWQEGNVFSCSVMHEALHNHYTQKSLKSLGK (Bold underlined residues represent mutations to parental Mab or WT sequence)

We claim:

1. A bispecific antibody comprising:
   a. a first heavy chain, wherein said first heavy chain comprises a first heavy chain variable domain ($V_H$) and a first human IgG heavy chain constant region, wherein said first human IgG heavy chain constant region is a human IgG1 or human IgG4 heavy chain constant region that comprises an alanine at residue 407, a methionine at residue 399, and an aspartic acid at residue 360 of the $C_H3$ domain;
   b. a first light chain, wherein said first light chain comprises a first light chain variable domain ($V_L$) and a first light chain constant domain ($C_L$);
   c. a second heavy chain, wherein said second heavy chain comprises a second $V_H$ and a second human IgG heavy chain constant region, wherein said second human IgG heavy chain constant region is a human IgG1 or human IgG4 heavy chain constant region that comprises an arginine at residues 345 and 347, a valine at residue 366 and a valine at residue 409 of the $C_H3$ domain; and
   d. a second light chain, wherein said second light chain comprises a second $V_L$ and a second $C_L$.

2. The bispecific antibody according to claim 1, wherein
   a. one of said first or second heavy chains further comprises a $V_H$ comprising a lysine at residue 39 and a glutamic acid at the residue which is four amino acids upstream of the first residue of HFR3 according to Kabat numbering system, and a human IgG1 or human IgG4 $C_H1$ domain comprising an alanine at residue 172 and a glycine at residue 174;
   b. one of said first or second light chains comprises a $V_L$ comprising an arginine at residue 1 and an aspartic acid at residue 38, and a $C_L$ comprising a tyrosine at residue 135 and a tryptophan at residue 176;
   c. the other of said first or second heavy chains further comprises a $V_H$ comprising a tyrosine at residue 39 and a WT human IgG1 or human IgG4 $C_H1$ domain; and
   d. the other of said first or second light chains comprises a $V_L$ comprising an arginine at residue 38 and a WT $C_L$, wherein
   the $V_H$ domain comprising a lysine at residue 39 and a glutamic acid at the residue which is four amino acids upstream of the first residue of HFR3 according to Kabat and the human IgG1 or human IgG4 $C_H1$ domain comprising an alanine at residue 172 and a glycine at residue 174 together with the $V_L$ comprising an arginine at residue 1 and an aspartic acid at residue 38 and the $C_L$ comprising a tyrosine at residue 135 and a tryptophan at residue 176 form a first Fab which directs binding to a first target; and the $V_H$ domain comprising a tyrosine at residue 39 and the WT human IgG1 or human IgG4 $C_H1$ domain together with the $V_L$ comprising an arginine at residue 38 and the WT $C_L$ domain form a second Fab which directs binding to a second target which is different from the first target.

3. The bispecific antibody of claim 1, wherein said first human IgG heavy chain constant region comprises SEQ ID NO: 39, and said second human IgG heavy chain constant region comprises SEQ ID NO: 43.

4. The bispecific antibody of claim 1, wherein said first human IgG heavy chain constant region comprises SEQ ID NO: 62, and said second human IgG heavy chain constant region comprises SEQ ID NO: 66.

5. The bispecific antibody according to claim 1, wherein
   a. one of said first or second heavy chains further comprises a VH comprising a lysine at residue 39 and a glutamic acid at the residue which is four amino acids upstream of the first residue of HFR3 according to Kabat Numbering system, and a human IgG1 or human IgG4 CH1 domain comprising an alanine at residue 172 and a glycine at residue 174;
   b. one of said first or second light chains comprises a VL comprising an arginine at residue 1 and an aspartic acid at residue 38, and a constant domain (CL) comprising a tyrosine at residue 135 and a tryptophan at residue 176;
c. the other of said first or second heavy chains further comprises a VH comprising a tyrosine at residue 39 and an arginine at residue 105 and a human IgG1 or human IgG4 CH1 domain comprising a cysteine at residue 127, an aspartic acid at residue 228, and a glycine at residue 230; and
d. the other of said first or second light chains comprises a variable domain (VL) comprising an arginine at residue 38 and an aspartic acid at residue 42, and a constant domain (CL) comprising a lysine at residue 122, wherein the VH domain comprising a lysine at residue 39 and a glutamic acid at the residue which is four amino acids upstream of the first residue of HFR3 according to Kabat and the human IgG1 or human IgG4 CH1 domain comprising an alanine at residue 172 and a glycine at residue 174 together with the VL comprising an arginine at residue 1 and an aspartic acid at residue 38 and the CL domain comprising a tyrosine at residue 135 and a tryptophan at residue 176 form a first Fab which directs binding to a first target; and the VH domain comprising a tyrosine at residue 39 and an arginine at residue 105 and the human IgG1 or human IgG4 CH1 domain comprising a cysteine at residue 127, an aspartic acid at residue 228, and a glycine at residue 230 together with the VL comprising an arginine at residue 38 and an aspartic acid at residue 42 and the CL domain comprising a lysine at residue 122 form a second Fab which directs binding to a second target which is different from the first target.

6. A bispecific antibody comprising:
a. a first heavy chain, wherein said first heavy chain comprises a first VH and a first human IgG heavy chain constant region, wherein said first human IgG heavy chain constant region is a human IgG1 or human IgG4 heavy chain constant region that comprises an alanine at residue 407, a glycine at residue 356, an aspartic acid at residue 357 and a glutamine at residue 364 of the $C_H3$ domain,
b. a first light chain, wherein said first light chain comprises a first VL and a first CL,
c. a second heavy chain, wherein said second heavy chain comprises a second VH and a second human IgG heavy chain constant region, wherein said second human IgG heavy chain constant region is a human IgG1 or human IgG4 heavy chain constant region that comprises a valine at residue 409, a methionine at residue 366, a serine at residue 349 and a tyrosine at residue 370 of the $C_H3$ domain, and
d. a second light chain, wherein said second light chain comprises a second VL and a second CL.

7. The bispecific antibody of claim 6, wherein said first human IgG heavy chain constant region comprises SEQ ID NO: 41, and said second human IgG heavy chain constant region comprises SEQ ID NO: 45.

8. The bispecific antibody of claim 6, wherein said first human IgG heavy chain constant region comprises SEQ ID NO: 64, and said second human IgG heavy chain constant region comprises SEQ ID NO: 68.

9. The bispecific antibody according to claim 6, wherein
a. one of said first or second heavy chains further comprises a VH comprising a lysine at residue 39 and a glutamic acid at the residue which is four amino acids upstream of the first residue of HFR3 according to Kabat numbering system, and a human IgG1 or human IgG4 CH1 domain comprising an alanine at residue 172 and a glycine at residue 174;
b. one of said first or second light chains comprises a VL comprising an arginine at residue 1 and an aspartic acid at residue 38, and a CL comprising a tyrosine at residue 135 and a tryptophan at residue 176;
c. the other of said first or second heavy chains further comprises a VH comprising a tyrosine at residue 39 and a WT human IgG1 or human IgG4 CH1 domain; and
d. the other of said first or second light chains comprises a VL comprising an arginine at residue 38 and a WT CL, wherein the VH domain comprising a lysine at residue 39 and a glutamic acid at the residue which is four amino acids upstream of the first residue of HFR3 according to Kabat and the human IgG1 or human IgG4 CH1 domain comprising an alanine at residue 172 and a glycine at residue 174 together with the VL comprising an arginine at residue 1 and an aspartic acid at residue 38 and the CL comprising a tyrosine at residue 135 and a tryptophan at residue 176 form a first Fab which directs binding to a first target; and the VH domain comprising a tyrosine at residue 39 and the WT human IgG1 or human IgG4 CH1 domain together with the VL comprising an arginine at residue 38 and the WT CL domain form a second Fab which directs binding to a second target which is different from the first target.

10. The bispecific antibody according to claim 6, wherein
a. one of said first or second heavy chains further comprises a VH comprising a lysine at residue 39 and a glutamic acid at the residue which is four amino acids upstream of the first residue of HFR3 according to Kabat Numbering system, and a human IgG1 or human IgG4 CH1 domain comprising an alanine at residue 172 and a glycine at residue 174;
b. one of said first or second light chains comprises a VL comprising an arginine at residue 1 and an aspartic acid at residue 38, and a constant domain (CL) comprising a tyrosine at residue 135 and a tryptophan at residue 176;
c. the other of said first or second heavy chains further comprises a VH comprising a tyrosine at residue 39 and an arginine at residue 105 and a human IgG1 or human IgG4 CH1 domain comprising a cysteine at residue 127, an aspartic acid at residue 228, and a glycine at residue 230; and
d. the other of said first or second light chains comprises a variable domain (VL) comprising an arginine at residue 38 and an aspartic acid at residue 42, and a constant domain (CL) comprising a lysine at residue 122, wherein the VH domain comprising a lysine at residue 39 and a glutamic acid at the residue which is four amino acids upstream of the first residue of HFR3 according to Kabat and the human IgG1 or human IgG4 CH1 domain comprising an alanine at residue 172 and a glycine at residue 174 together with the VL comprising an arginine at residue 1 and an aspartic acid at residue 38 and the CL domain comprising a tyrosine at residue 135 and a tryptophan at residue 176 form a first Fab which directs binding to a first target; and the VH domain comprising a tyrosine at residue 39 and an arginine at residue 105 and the human IgG1 or human IgG4 CH1 domain comprising a cysteine at residue 127, an aspartic acid at residue 228, and a glycine at residue 230 together with the VL comprising an arginine at residue 38 and an aspartic acid at residue 42 and the CL domain comprising a lysine at residue 122 form a second Fab which directs binding to a second target which is different from the first target.

* * * * *